US012653618B2

(12) United States Patent
Metcalfe et al.

(10) Patent No.: US 12,653,618 B2
(45) Date of Patent: Jun. 16, 2026

(54) FRAGMENT REGISTRATION AND ASSOCIATED METHODS FOR REPAIRING FRACTURED BONES

(71) Applicant: ARTHREX, INC., Naples, FL (US)

(72) Inventors: Nick Metcalfe, Bonita Springs, FL (US); Sergii Poltaretskyi, Ependes FR (CH)

(73) Assignee: ARTHREX, INC., Naples, FL (US)

( * ) Notice: Subject to any disclaimer, the term of this patent is extended or adjusted under 35 U.S.C. 154(b) by 330 days.

(21) Appl. No.: 18/353,541

(22) Filed: Jul. 17, 2023

(65) Prior Publication Data

US 2024/0058068 A1     Feb. 22, 2024

Related U.S. Application Data

(60) Provisional application No. 63/406,562, filed on Sep. 14, 2022, provisional application No. 63/399,190, filed on Aug. 18, 2022.

(51) Int. Cl.
| | |
|---|---|
| *A61B 34/10* | (2016.01) |
| *G16H 20/40* | (2018.01) |
| *G16H 30/20* | (2018.01) |
| *G16H 50/50* | (2018.01) |

(52) U.S. Cl.
CPC ............. *A61B 34/10* (2016.02); *G16H 20/40* (2018.01); *G16H 30/20* (2018.01); *G16H 50/50* (2018.01); *A61B 2034/104* (2016.02); *A61B 2034/105* (2016.02)

(58) Field of Classification Search
USPC ........................................ 382/128
See application file for complete search history.

(56) References Cited

U.S. PATENT DOCUMENTS

| | | |
|---|---|---|
| 9,101,394 B2 | 8/2015 | Arata et al. |
| 9,129,054 B2 | 9/2015 | Nawana et al. |
| 9,271,848 B2 | 3/2016 | Brooks |

(Continued)

FOREIGN PATENT DOCUMENTS

| | | |
|---|---|---|
| WO | 2018067966 A8 | 5/2018 |
| WO | 2018107042 A2 | 6/2018 |

(Continued)

OTHER PUBLICATIONS

Kozic, N. (2009). Statistical shape space analysis based on level sets for optimization of orthopaedic implant design. PhD Thesis. Graduate School for Cellular and Biomedical Sciences. University of Bern. Retrieved from: https://biblio.unibe.ch/download/eldiss/09kozic_n.pdf.

(Continued)

*Primary Examiner* — Mark D Remaly
(74) *Attorney, Agent, or Firm* — Carlson, Gaskey & Olds, P.C.

(57) ABSTRACT

Bone fractures may be associated with one or more fragments separated from a bone. The fractured bone may be captured with an imaging device. The disclosed systems may be configured to predict or otherwise determine a position of the fragments prior to occurrence of the bone fracture. The determined position may be utilized to position and secure the fragments during a surgical procedure. Methods for determining the pre-fracture position of bone fragments are also disclosed.

23 Claims, 54 Drawing Sheets

(56) References Cited

U.S. PATENT DOCUMENTS

| | | | |
|---|---|---|---|
| 9,320,604 | B2 | 4/2016 | Miles et al. |
| 9,665,686 | B2 | 5/2017 | Van Vorhis et al. |
| 9,700,292 | B2 | 7/2017 | Nawana et al. |
| 9,717,508 | B2 | 8/2017 | Iannotti et al. |
| 9,730,628 | B2 | 8/2017 | Iasemidis et al. |
| 9,741,263 | B2 | 8/2017 | Iannotti et al. |
| 9,827,051 | B2 | 11/2017 | Arata et al. |
| 9,913,691 | B2 | 3/2018 | Brooks |
| 9,913,692 | B2 | 3/2018 | Arata et al. |
| 9,916,421 | B2 | 3/2018 | Vorhis et al. |
| 10,130,378 | B2 | 11/2018 | Bryan |
| 10,172,675 | B2 | 1/2019 | Mahfouz |
| 10,327,852 | B2 | 6/2019 | Meridew et al. |
| 10,449,003 | B2 | 10/2019 | Reid et al. |
| 10,452,238 | B2 | 10/2019 | Nikou et al. |
| 10,512,496 | B2 | 12/2019 | Iannotti et al. |
| 10,537,390 | B2 | 1/2020 | Varadarajan et al. |
| 10,595,943 | B2 | 3/2020 | Barsoum et al. |
| 10,624,655 | B2 | 4/2020 | Iannotti et al. |
| 10,660,705 | B2 | 5/2020 | Piron et al. |
| 10,660,709 | B2 | 5/2020 | Chaoui |
| 10,736,697 | B2 | 8/2020 | Chaoui et al. |
| 10,739,963 | B2 | 8/2020 | Nikou et al. |
| 10,973,580 | B2 | 4/2021 | Berend et al. |
| 11,083,525 | B2 | 8/2021 | Varadarajan et al. |
| 11,259,874 | B1 * | 3/2022 | Landon ................... G16H 40/67 |
| 11,419,680 | B2 | 8/2022 | Kontaxis et al. |
| 11,443,846 | B2 | 9/2022 | Schoenefeld et al. |
| 11,464,569 | B2 | 10/2022 | Lambers et al. |
| 11,478,168 | B2 | 10/2022 | Fleig et al. |
| 11,488,721 | B2 | 11/2022 | Otto et al. |
| 11,532,402 | B2 | 12/2022 | Farley et al. |
| 11,803,969 | B2 | 10/2023 | Campbell et al. |
| 12,283,047 | B2 | 4/2025 | Campbell et al. |
| 2004/0102866 | A1 | 5/2004 | Harris et al. |
| 2004/0233387 | A1 | 11/2004 | Huang et al. |
| 2011/0082367 | A1 * | 4/2011 | Regazzoni ............. A61B 34/20 |
| | | | 600/425 |
| 2012/0276509 | A1 | 11/2012 | Iannotti et al. |
| 2014/0013565 | A1 | 1/2014 | Macdonald et al. |
| 2014/0257402 | A1 | 9/2014 | Barsoum |
| 2014/0272881 | A1 | 9/2014 | Barsoum |
| 2014/0278322 | A1 | 9/2014 | Jaramaz et al. |
| 2014/0303990 | A1 | 10/2014 | Schoenefeld et al. |
| 2015/0093734 | A1 | 4/2015 | Kaouk |
| 2016/0278868 | A1 | 9/2016 | Berend et al. |
| 2017/0296205 | A1 | 10/2017 | Iannotti et al. |
| 2018/0033338 | A1 | 2/2018 | Iannotti et al. |
| 2018/0168731 | A1 * | 6/2018 | Reid ...................... A61B 34/10 |
| 2018/0233222 | A1 | 8/2018 | Daley et al. |
| 2018/0358120 | A1 | 12/2018 | Schoenefeld et al. |
| 2019/0005186 | A1 | 1/2019 | Nikou et al. |
| 2019/0231431 | A1 | 8/2019 | Paszicsnyek |
| 2019/0246944 | A1 * | 8/2019 | Mahfouz ................ A61B 34/20 |
| 2019/0380792 | A1 | 12/2019 | Poltaretskyi et al. |
| 2019/0388153 | A1 | 12/2019 | Running et al. |
| 2020/0030034 | A1 | 1/2020 | Kontaxis et al. |
| 2020/0113632 | A1 | 4/2020 | Varadarajan et al. |
| 2020/0188026 | A1 | 6/2020 | De Souza et al. |
| 2020/0205900 | A1 | 7/2020 | Buckland et al. |
| 2020/0219626 | A1 | 7/2020 | Otto et al. |
| 2020/0246075 | A1 | 8/2020 | Dohmen et al. |
| 2020/0246077 | A1 | 8/2020 | Chaoui |
| 2021/0000380 | A1 | 1/2021 | West et al. |
| 2021/0093385 | A1 | 4/2021 | Morvan et al. |
| 2021/0093391 | A1 | 4/2021 | Poltaretskyi et al. |
| 2021/0093414 | A1 | 4/2021 | Moore et al. |
| 2021/0100620 | A1 | 4/2021 | Chaoui et al. |
| 2021/0104325 | A1 | 4/2021 | Chaoui et al. |
| 2021/0210189 | A1 | 7/2021 | Casey et al. |
| 2021/0307833 | A1 | 10/2021 | Farley et al. |
| 2021/0315640 | A1 | 10/2021 | Dees, Jr. et al. |
| 2021/0322148 | A1 | 10/2021 | Mitra et al. |
| 2022/0039868 | A1 | 2/2022 | Chaoui et al. |
| 2022/0059212 | A1 | 2/2022 | Chaoui et al. |
| 2022/0059213 | A1 | 2/2022 | Chaoui et al. |
| 2022/0117663 | A1 | 4/2022 | Mcguan et al. |
| 2022/0117755 | A1 | 4/2022 | Mcguan et al. |
| 2022/0226044 | A1 | 7/2022 | Metcalfe et al. |
| 2022/0273281 | A1 | 9/2022 | McKinnon et al. |

FOREIGN PATENT DOCUMENTS

| | | | | |
|---|---|---|---|---|
| WO | 2019245849 | A1 | 12/2019 | |
| WO | 2019245865 | A1 | 12/2019 | |
| WO | 2019245854 | A3 | 2/2020 | |
| WO | 2020033568 | A2 | 2/2020 | |
| WO | 2020037308 | A1 | 2/2020 | |
| WO | WO-2020056443 | A1 * | 3/2020 | ............. A61B 17/56 |
| WO | 2020072255 | A1 | 4/2020 | |
| WO | 2020123706 | A1 | 6/2020 | |
| WO | 2020163317 | A1 | 8/2020 | |
| WO | 2020163318 | A1 | 8/2020 | |
| WO | 2020163324 | A1 | 8/2020 | |
| WO | 2020163352 | A1 | 8/2020 | |
| WO | 2020163358 | A1 | 8/2020 | |
| WO | 2021086687 | A1 | 5/2021 | |
| WO | 2022066693 | A1 | 3/2022 | |
| WO | 2022076773 | A1 | 4/2022 | |

OTHER PUBLICATIONS

International Search Report and Written Opinion for International Application No. PCT/US2022/043287 dated Feb. 6, 2023.

Moroder, P., Akgun, D., Plachel, F., Baur, A.D.J., Siegert, P. (2020). The influence of posture and scapulothoracic orientation on the choice of humeral component retrotorsion in reverse total shoulder arthroplasty. Journal of Shoulder and Elbow Surgery. vol. 29. pp. 1992-2001.

Moroder, P., Urvoy, M., Raiss, P., Werthel, J-D., Akgun, D., Chaoui, J., Siegert, P. (2022). Patient posture affects simulated ROM in reverse total shoulder arthroplasty: A modeling study using preoperative planning software. Clincal Orthopaedics and Related Reserach. vol. 480(3). pp. 619-31.

Poltaretskyi, S., Chaoui, J., Mayya, M., Hamitouche, C., Bercik, M.J., Boileau, P., Walch, G. (2017). Prediction of the pre-morbid 3D anatomy of the proximal humerus based on statistical shape modelling. The Bone & Joint Journal. vol. 99-B(7). Jul. 2017. pp. 927-933.

Simon, P., Diaz, M., Cusick, M., Santoni, B., and Frankle, M. (2018). 3D image-based morphometric analysis of the scapular neck length in subjects undergoing reverse shoulder arthroplasty. Clinical Anatomy. vol. 31(1). Jul. 27, 2017. pp. 43-55.

Steinhaus, M.E., Mclawhorn, A.S., Richardson, S., Maher, P., Mayman, D.J. (2016). Handheld navigation device and patient-specific cutting guides result in similar coronal alignment for primary total knee arthroplasty: A retrospective matched cohort study. HSS Journal. vol. 12(3). Feb. 29, 2016. pp. 224-234.

Von Eisenhart-Rothe, R., Jager, A., Englmeier, K-H., Vogl, T., Graichen, H. (2003). Pathomechanics in atraumatic shoulder instability—Correlation between scapular kinematics and humeral head position. 49th Annual Meeting of the Orthopaedic Research Society. Feb. 2-5, 2003.

Von Eisenhart-Rothe, R., Jager, A., Englmeier, K-H., Vogl, T., Graichen, H. (2003). Pathomechanics in atraumatic shoulder instability—Correlation between scapular kinematics and humeral head position. 49th Annual Meeting of the Orthopaedic Research Society. Feb. 2003.

International Search Report Written Opinion for International Application No. PCT/US2023/028549 mailed Jan. 4, 2024.

Moroder, P., MEng, Mu., Raiss, P., Werthel, J-D., Akgun, D., Chaoui, J., Siegert, P. (2022). Patient posture affects simulated ROM in reverse total shoulder arthroplasty: A modeling study using preoperative planning software. Clin Orthop Relat Res (2022) 480:619-631.

* cited by examiner

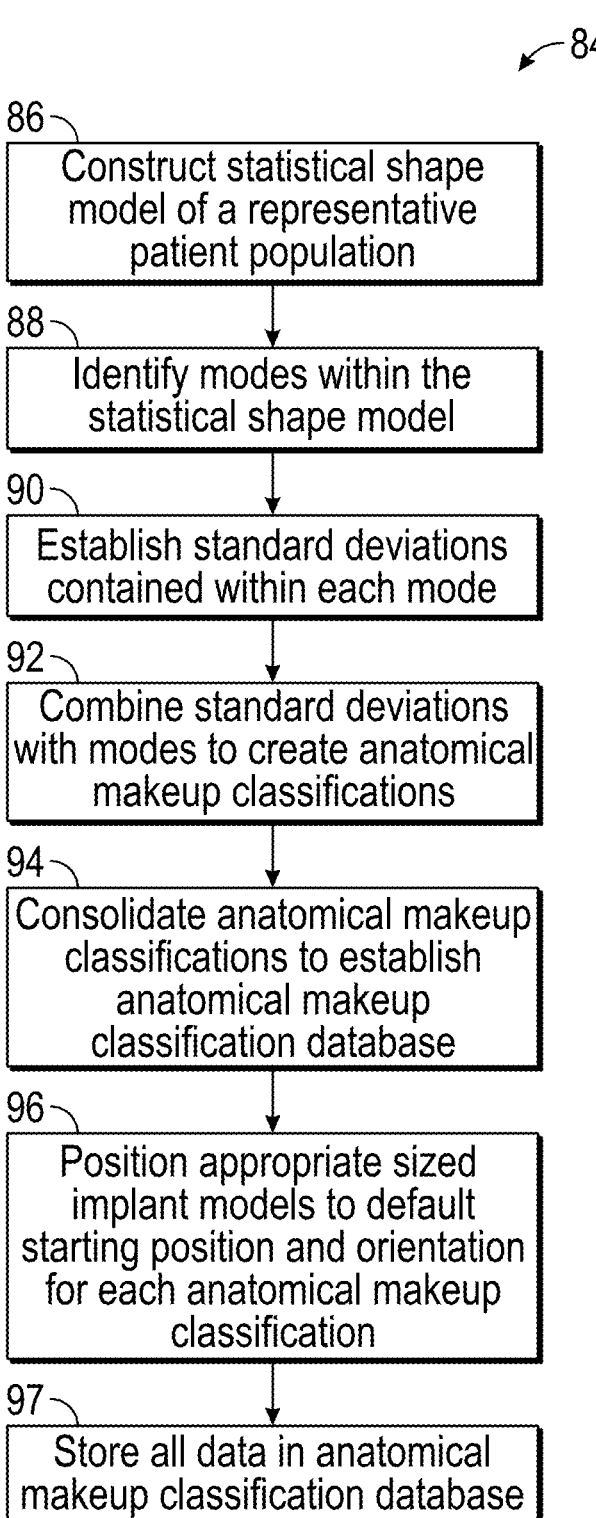

84

86
Construct statistical shape
model of a representative
patient population

88
Identify modes within the
statistical shape model

90
Establish standard deviations
contained within each mode

92
Combine standard deviations
with modes to create anatomical
makeup classifications 94
Consolidate anatomical makeup
classifications to establish
anatomical makeup
classification database 96
Position appropriate sized
implant models to default
starting position and orientation
for each anatomical makeup
classification 97
Store all data in anatomical
makeup classification database

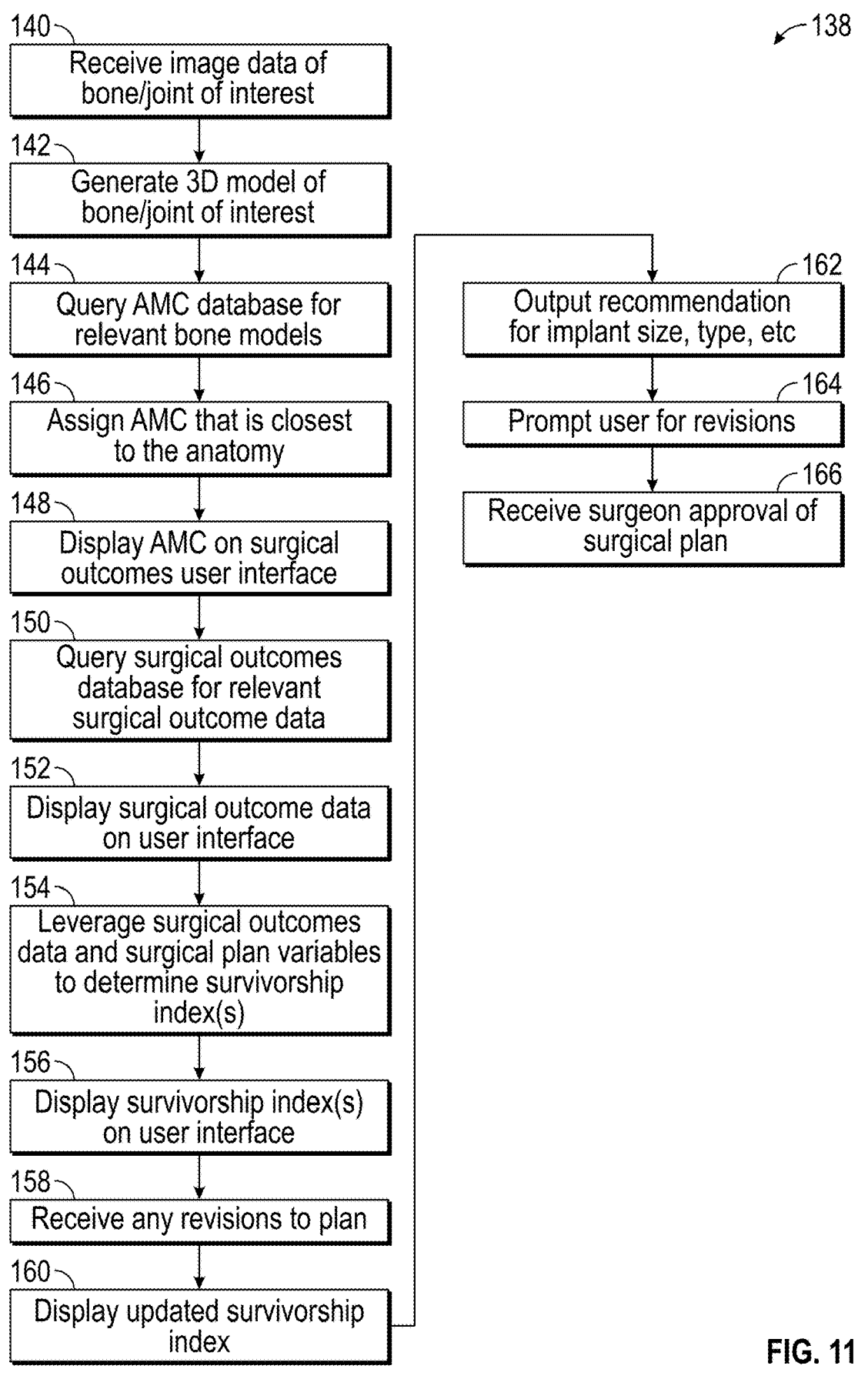

140
Receive image data of
bone/joint of interest

142
Generate 3D model of
bone/joint of interest

144
Query AMC database for
relevant bone models

146
Assign AMC that is closest
to the anatomy

148
Display AMC on surgical
outcomes user interface

150
Query surgical outcomes
database for relevant
surgical outcome data

152
Display surgical outcome data
on user interface

154
Leverage surgical outcomes
data and surgical plan variables
to determine survivorship
index(s)

156
Display survivorship index(s)
on user interface

158
Receive any revisions to plan

160
Display updated survivorship
index

162
Output recommendation
for implant size, type, etc

164
Prompt user for revisions

166
Receive surgeon approval of
surgical plan

FIG. 11

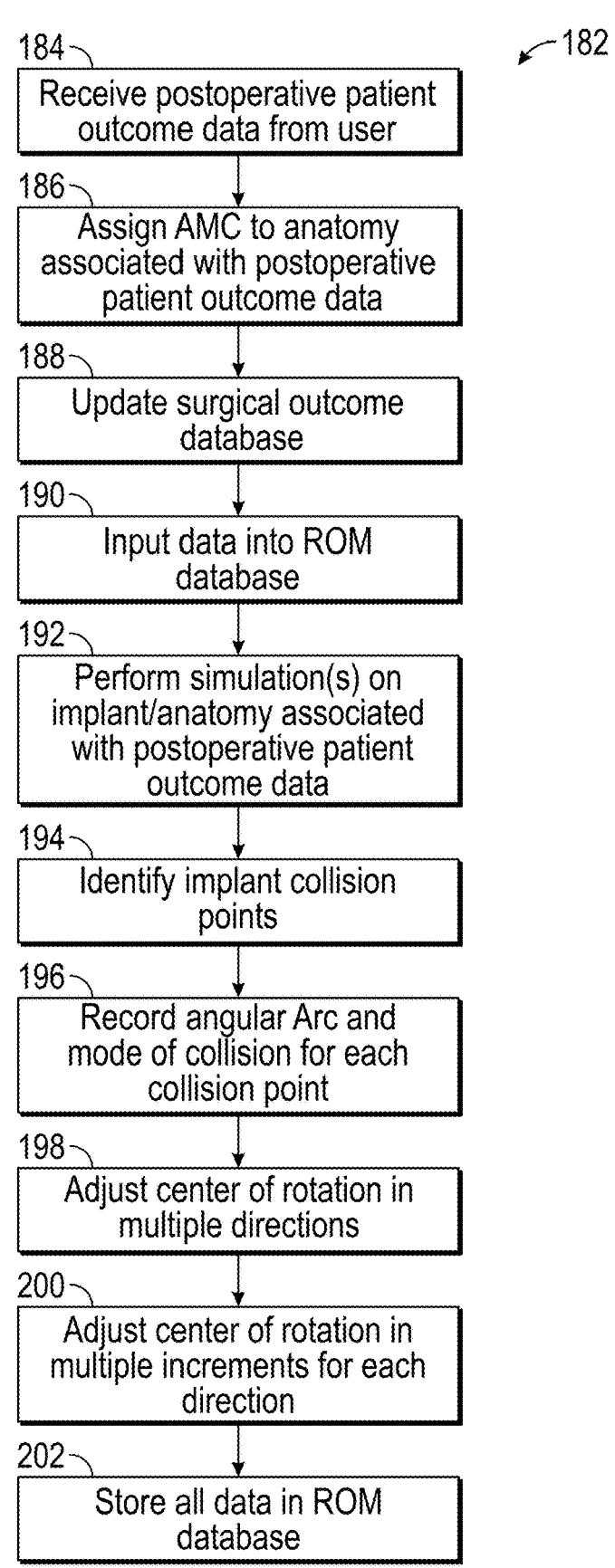

184 — Receive postoperative patient outcome data from user

186 — Assign AMC to anatomy associated with postoperative patient outcome data

188 — Update surgical outcome database

190 — Input data into ROM database

192 — Perform simulation(s) on implant/anatomy associated with postoperative patient outcome data 194 — Identify implant collision points 196 — Record angular Arc and mode of collision for each collision point 198 — Adjust center of rotation in multiple directions 200 — Adjust center of rotation in multiple increments for each direction 202 — Store all data in ROM database

Type A            Type B            Type C 229,229-4

230U

230R

230H 230,230S 330,330S

PL,P2
SA
PL,P1
P3

329,329SM 332G
330,330S
Z
332
X
332H
PL,P1
330H

Z
X
P0
Y

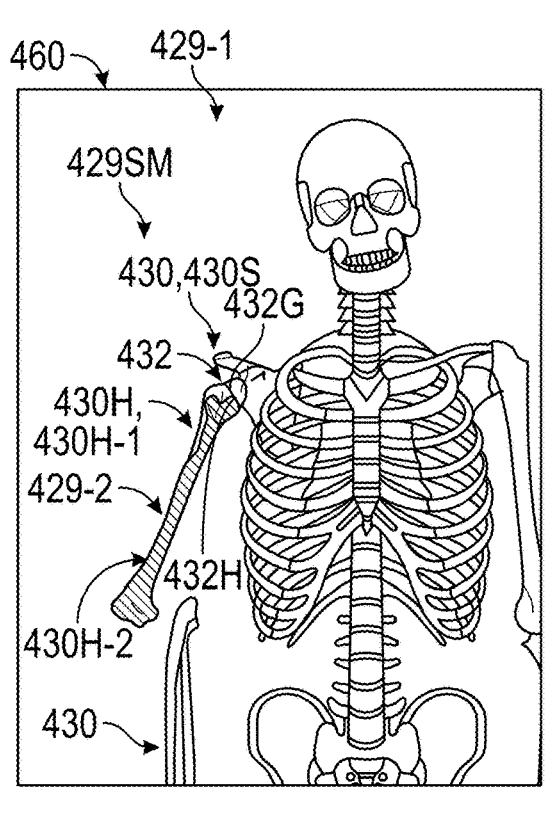
FIG. 37A
FIG. 37B
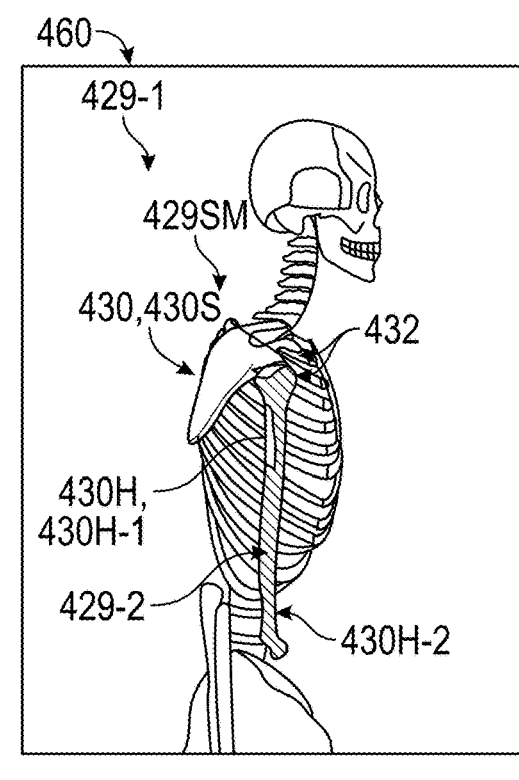
FIG. 38A
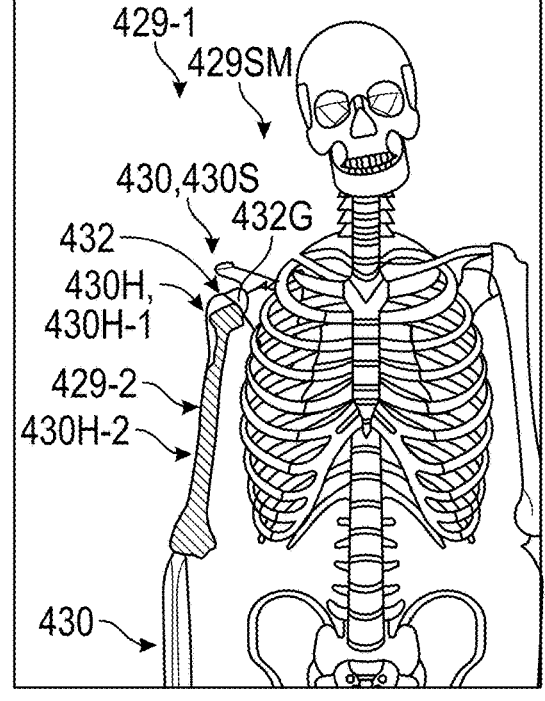
FIG. 38B

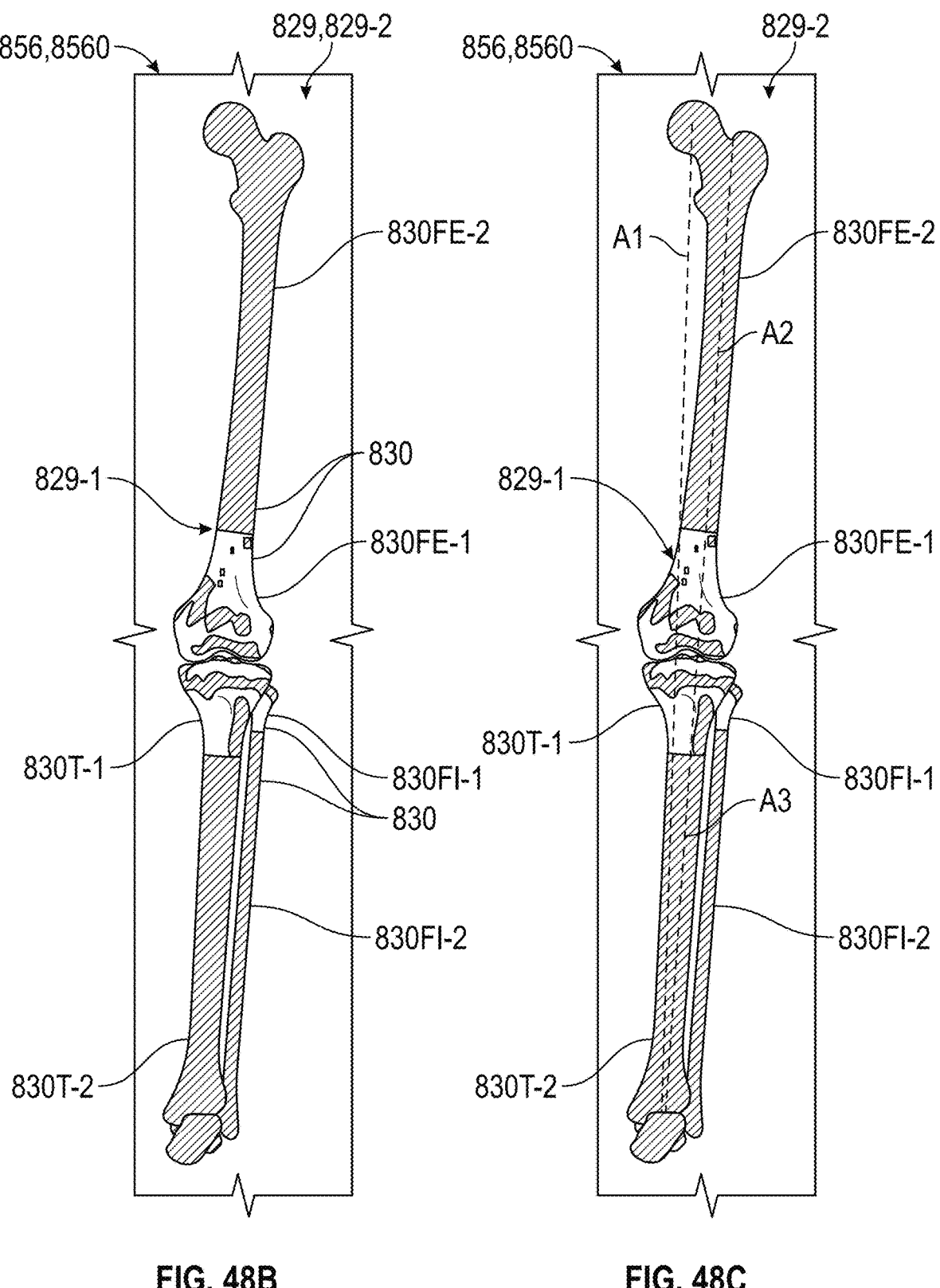
FIG. 48B        FIG. 48C

1056,1060

1056,1060

1029-2

1030

1030FE-2

1029-1

1030FE-1

1030FE,
1030FE-1

1030FI-2

1030T-2

1356,1360

1330F-1'

1330-1'

1330P-1'

F

1332

F 1330M-1'

FRAGMENT REGISTRATION AND ASSOCIATED METHODS FOR REPAIRING FRACTURED BONES

CROSS-REFERENCE TO RELATED APPLICATION

This application claims the benefit of U.S. Provisional Application No. 63/399,190 filed on Aug. 18, 2022 and U.S. Provisional Application No. 63/406,562 filed on Sep. 14, 2022, each of which is incorporated herein by reference in its entirety.

BACKGROUND

This disclosure is directed to surgical planning, and more particularly to improved surgical planning systems and methods for planning orthopedic procedures.

Arthroplasty is a type of orthopedic surgical procedure performed to repair or replace diseased joints. Surgeons may desire to establish a surgical plan for preparing a surgical site, selecting an implant, and placing the implant at the surgical site prior to performing arthroplasty in order to improve outcomes. Surgical planning may include capturing an image of the surgical site and determining a position of an implant based on the image.

SUMMARY

This disclosure relates to improved surgical planning systems and methods.

The surgical planning system and methods of this disclosure may be utilized in some implementations for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint.

A surgical planning system may include, inter alia, a processor configured to categorize a representative patient population into a plurality of anatomical makeup classifications, and perform a range of motion simulation for each of the plurality of anatomical makeup classifications. A memory device of the system may be operably coupled to the processor and may be configured to store range of motion data derived from the range of motion simulation for each of the plurality of anatomical makeup classifications.

A computer implemented surgical planning method may include, inter alia, categorizing, via a processor of a surgical planning system, a representative patient population into a plurality of anatomical makeup classifications, performing a range of motion simulation on each of the plurality of anatomical makeup classifications, and storing range of motion data derived from the range of motion simulation for each of the plurality of anatomical makeup classifications within a memory device of the surgical planning system.

A surgical planning system according to an implementation may include, inter alia, a processor operably connected to a storage system. The storage system may be configured to store a plurality of three-dimensional bone models associated with one or more bones of a representative patient population. The plurality of bone models may include a first set associated with a first bone and a second set associated with a second bone. The processor may be configured to select a first representative bone model from the first set of the bone models in response to comparing the first representative bone model to a first patient three-dimensional bone model associated with the first bone of a patient. The first representative bone model may be associated with a second representative bone model of the second set of the bone models. The first patient bone model and a second patient three-dimensional bone model may establish a first spatial relationship. The second patient bone model may be associated with the second bone of the patient. The first and second representative bone models may establish a second spatial relationship. The processor may be configured to determine at least one patient characteristic associated with the first bone and/or the second bone of the patient in response to comparing the first and second spatial relationships.

A computer implemented surgical planning method according to an implementation may include, inter alia, accessing a first patient bone model of a patient from memory. The first patient model may be associated with a first bone of a patient. The method may include accessing a second patient bone model of the patient from the memory. The second patient bone model may be associated with a second bone of the patient. The method may include selecting an anatomical model from a plurality of anatomical models based on the first patient bone model and the second patient bone model. The plurality of anatomical models may be associated with one or more bones and/or one or more joints of a representative patient population that may include at least the first bone and the second bone. The method may include determining one or more characteristics associated with a posture of the patient based on the selected anatomical model.

A surgical planning system according to an implementation may include, inter alia, a processor and memory operably coupled to the processor. The processor may be configured to receive image data including first and second two-dimensional images of first and second bones of a patient. The processor may be configured to determine a first profile of the first and second bones along a first reference plane associated with the first image. The processor may be configured to determine a second profile of the first and second bones along a second reference plane associated with the second image. The processor may be configured to determine an orientation of the first and second bones based on a representative anatomical model associated with another patient, which may include projecting a first silhouette of the representative anatomical model onto the first profile along the first reference plane, and which may include projecting a second silhouette of the representative anatomical model onto the second profile along the second reference plane. The processor may be configured to determine one or more posture characteristics associated with a posture of the patient based on the determined orientation. The processor may be configured to establish a surgical plan associated with the first bone and/or the second bone based on the one or more posture characteristics.

A surgical planning system according to an implementation may include, inter alia, a processor operably connected to memory. The processor may be configured to access a first three-dimensional bone model from the memory. The first bone model may be associated with a first bone. The processor may be configured to access a partial three-dimensional bone model of the first bone of a patient. The partial bone model may be representative of a lesser portion of the first bone than the first representative bone model. The processor may be configured to at least partially register the partial bone model of the first bone to the first bone model to establish a registered position of the first bone model.

A surgical planning system according to an implementation may include, inter alia, a processor operably connected to a storage system. The storage system may be configured to store a plurality of three-dimensional bone models associated with one or more bones and/or one or more joints of a representative patient population. The processor may be configured to select a first representative three-dimensional bone model from a first set of the bone models associated with a first bone of the representative patient population. The processor may be configured to at least partially register a partial three-dimensional bone model of the first bone of a patient to the first representative bone model. The partial bone model may be representative of a lesser portion of the first bone than the first bone model.

A computer implemented surgical planning method according to an implementation may include, inter alia, selecting a first representative three-dimensional bone model associated with a first bone. The method may include selecting a partial three-dimensional bone model of the first bone of a patient. The partial bone model may be representative of a lesser portion of the first bone than the first representative bone model. The method may include at least partially registering the partial bone model of the first bone to the first representative bone model to establish a registered position of the first representative bone model. The method may include analyzing the first bone based on the registered position of the first representative bone model.

A surgical planning system according to an implementation may include, inter alia, a processor operably connected to memory. The processor may be configured to access a first three-dimensional bone model from the memory. The first bone model may be associated with a first bone. The processor may be configured to access a fragmentary three-dimensional bone model of the first bone of a patient. The fragmentary bone model may include one or more fragment portions associated with one or more respective fragments of the first bone. The processor may be configured to at least partially register the one or more fragment portions of the fragmentary bone model to a volume of the first bone model to establish a registered state of the fragmentary bone model.

A surgical planning system according to an implementation may include, inter alia, a processor operably connected to a storage system. The storage system may be configured to store a plurality of three-dimensional bone models associated with one or more bones and/or one or more joints of a representative patient population. The processor may be configured to select a first three-dimensional bone model from a first set of the bone models associated with a first bone of the representative patient population. The processor may be configured to at least partially register one or more fragment portions of a fragmentary three-dimensional bone model of the first bone of a patient to the first bone model to establish a registered state of the fragmentary bone model. The one or more fragment portions may be associated with one or more respective fragments of the first bone.

A computer implemented surgical planning method according to an implementation may include, inter alia, selecting a first three-dimensional bone model associated with a first bone. The method may include selecting a fragmentary three-dimensional bone model of the first bone of a patient. The fragmentary bone model may include one or more fragment portions associated with one or more respective fragments of the first bone. The method may include at least partially registering the one or more fragment portions of the fragmentary bone model to a volume of the first bone model to establish a registered state of the fragmentary bone model. The method may include analyzing the first bone based on the registered state of the fragmentary bone model.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 6 schematically illustrates a method for establishing an anatomical makeup classification database of a surgical planning system.

FIG. 11 schematically illustrates another exemplary method for planning an orthopedic procedure on a respective patient using a surgical planning system.

FIG. 14 schematically illustrates an exemplary method for postoperatively updating one or more databases associated with a surgical planning system.

FIG. 34 discloses an anatomical model.

FIGS. 35-36, 37A-37B and 38A-38B disclose an anatomical model.

FIGS. 48A-48C disclose an anatomical model associated with a knee joint of a patient.

Like reference numbers and designations in the various drawings indicate like elements.

DETAILED DESCRIPTION

Figure 1:
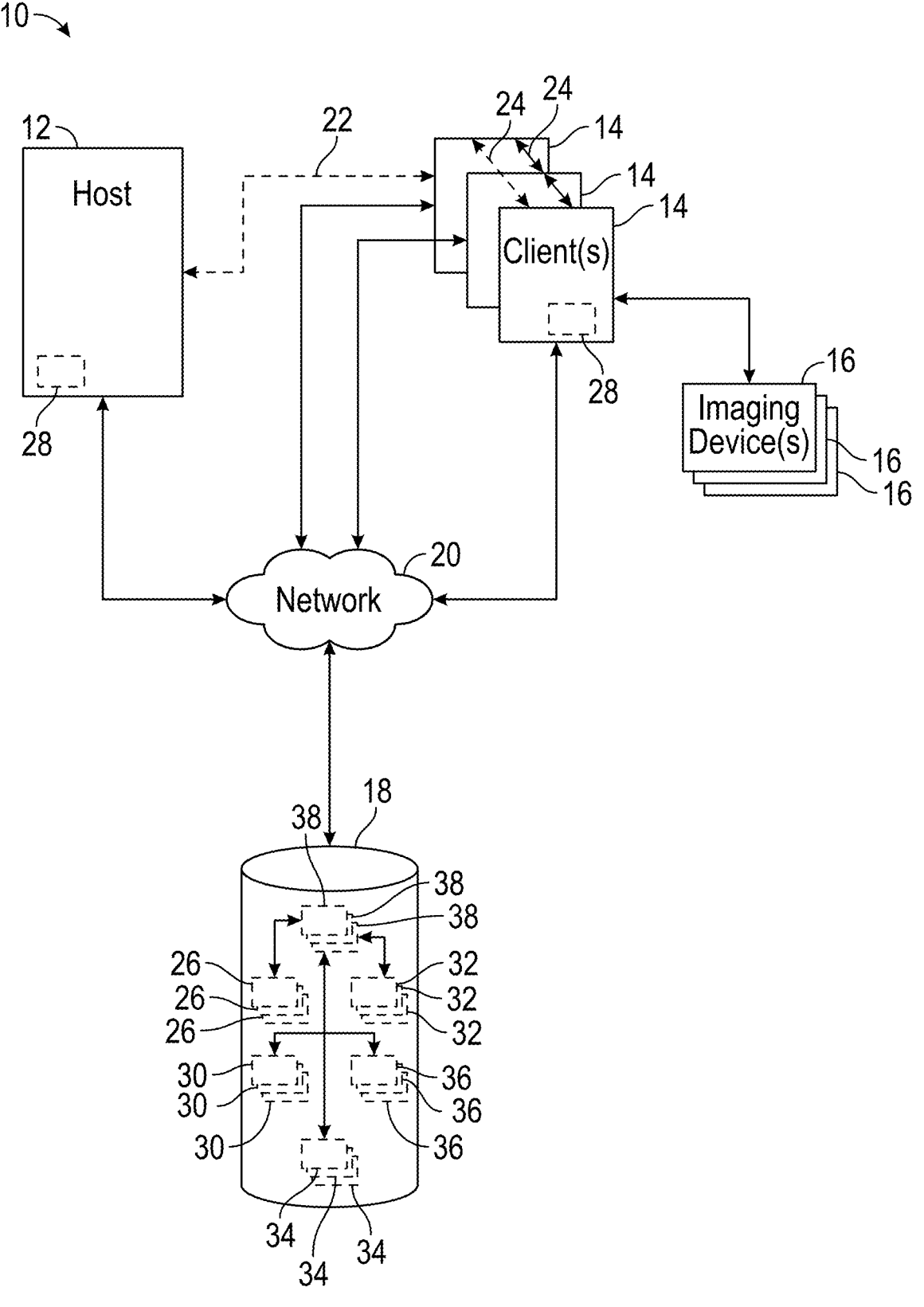
FIG. 1 schematically illustrates an exemplary surgical planning system.

This disclosure is directed to improved surgical planning systems and methods for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint. These and other features of this disclosure are discussed in greater detail in the following paragraphs of this detailed description.

A surgical planning system according to an implementation may include a processor. The processor may be configured to categorize a representative patient population into a plurality of anatomical makeup classifications. The processor may be configured to perform a range of motion simulation for each of the plurality of anatomical makeup classifications. A storage system may be operably connected to the processor and may be configured to store range of motion data that may be derived from the range of motion simulation for each of the plurality of anatomical makeup classifications.

In any implementations, the range of motion simulation may be configured to simulate a motion-related characteristic associated with a virtual joint that may be derived from the representative patient population. The virtual joint may include one or more bones and may include a virtual surgical implant positioned relative to the one or more bones.

In any implementations, the motion-related characteristic may include an abduction, an adduction, an extension, a flexion, an internal rotation, an external rotation, or any combinations thereof.

In any implementations, the processor may be configured to identify a collision point that may mark a maximum range of motion associated with the motion-related characteristic.

In any implementations, the processor may be configured to identify an angular arc and a mode of collision associated with the collision point.

In any implementations, the processor may be configured to adjust a position of the virtual surgical implant relative to the one or more bones in a plurality of offset directions.

In any implementations, the processor may be configured to identify a second angular arc and a second mode of collision associated with a second collision point based on the adjusted position of the virtual surgical implant.

In any implementations, the processor may be configured to receive image data associated with a patient. The processor may be configured to generate a three-dimensional model of a bone or a joint of the patient based on the image data. The processor may be configured to assign one of the plurality anatomical makeup classifications to the three-dimensional model of the bone or the joint. The processor may be configured to display the range of motion data for the assigned anatomical makeup classification.

In any implementations, the processor may be configured to receive an input of an act of daily living goal for the patient. The processor may be configured to adjust a position of a virtual surgical implant within the three-dimensional model for achieving the act of daily living goal.

In any implementations, the processor may be configured to query a surgical outcomes database of the surgical planning system for postoperative surgical outcome data. The processor may be configured to assign one of the plurality anatomical makeup classifications to an anatomy associated with the postoperative surgical outcome data. The processor may be configured to update the range of motion data associated with the assigned anatomical makeup classification based on the postoperative surgical outcome data.

A computer implemented surgical planning method according to an implementation may include the step of categorizing, via a processor of a surgical planning system, a representative patient population into a plurality of anatomical makeup classifications. The method may include the step of performing a range of motion simulation on each of the plurality of anatomical makeup classifications. The method may include the step of storing range of motion data derived from the range of motion simulation for each of the plurality of anatomical makeup classifications within a storage system of the surgical planning system.

In any implementations, the range of motion simulation may be configured to simulate a motion-related characteristic associated with a virtual joint that may be derived from the representative patient population. The virtual joint may include one or more bones and may include a virtual surgical implant positioned relative to the one or more bones.

In any implementations, performing the range of motion simulation may include identifying a collision point that may mark a maximum range of motion associated with the motion-related characteristic within the virtual joint.

In any implementations, performing the range of motion simulation may include identifying an angular arc and a mode of collision associated with the collision point.

In any implementations, performing the range of motion simulation may include adjusting a position of the virtual surgical implant relative to the one or more bones in a plurality of offset directions.

In any implementations, performing the range of motion simulation may include identifying a second angular arc and a second mode of collision associated with a second collision point based on the adjusted position of the virtual surgical implant.

In any implementations, the motion-related characteristic may include an abduction, an adduction, an extension, a flexion, an internal rotation, an external rotation, or any combinations thereof.

In any implementations, the method may include receiving image data associated with a patient. The method may include generating a three-dimensional model of a bone or a joint of the patient based on the image data. The method may include assigning one of the plurality anatomical makeup classifications to the three-dimensional model of the bone or the joint. The method may include displaying the range of motion data for the assigned anatomical makeup classification.

In any implementations, the method may include receiving an input of an act of daily living goal for the patient. The method may include adjusting a position of a virtual surgical implant within the three-dimensional model for achieving the act of daily living goal.

In any implementations, the method may include querying a surgical outcomes database of the surgical planning system for postoperative surgical outcome data. The method may include assigning one of the plurality anatomical makeup classifications to an anatomy associated with the postoperative surgical outcome data. The method may include updating the range of motion data associated with the assigned anatomical makeup classification based on the postoperative surgical outcome data.

A surgical planning system according to an implementation may include a processor operably connected to a storage system. The storage system may be configured to store a plurality of three-dimensional bone models associated with one or more bones of a representative patient population. The plurality of bone models may include a first set associated with a first bone and a second set associated with a second bone. The processor may be configured to select a first representative bone model from the first set of the bone models in response to comparing the first representative bone model to a first patient three-dimensional bone model associated with the first bone of a patient. The first representative bone model may be associated with a second representative bone model of the second set of the bone models. The first patient bone model and a second patient three-dimensional bone model may establish a first spatial relationship. The second patient bone model may be associated with the second bone of the patient. The first and second representative bone models may establish a second spatial relationship. The processor may be configured to determine at least one patient characteristic associated with the first bone and/or the second bone of the patient in response to comparing the first and second spatial relationships.

In any implementations, the at least one patient characteristic may be associated with a posture of the patient.

In any implementations, the processor may be configured to establish an implant plan based on the at least one patient characteristic.

In any implementations, the first bone and the second bone may be adjoining bones.

In any implementations, the first bone and the second bone may be non-adjoining bones.

In any implementations, the processor may be configured to performing a range of motion simulation based on the at least one patient characteristic.

In any implementations, the processor may be configured to receive image data associated with the patient. The processor may be configured to generate the first and second patient bone models based on the image data.

In any implementations, the processor may be configured determine a deviation between the first and second spatial relationships based on one or more landmarks associated with the first bone and/or the second bone. The processor may be configured to determine the at least one patient characteristic based on the deviation.

In any implementations, the processor may be configured to compare the first representative bone model to the first patient bone model in response to at least partially fitting a volume of the first representative model and a volume of the first patient bone model to each other. The processor may be configured to compare the second representative bone model to the second patient bone model in response to at least partially fitting a volume of the second representative bone model and a volume of the second patient bone model to each other.

In any implementations, the processor may be configured to adjust a position of the first patient bone model and/or a position of the second patient bone model based on the at least one patient characteristic.

In any implementations, the processor may be configured to register the first patient bone model and/or the second patient bone model from a local reference system to a global reference system based on the at least one patient characteristic. The processor may be configured to establish a surgical plan associated with the first patient bone model and/or the second patient bone model in the global reference system.

In any implementations, the processor may be configured to analyze the representative patient population within a statistical shape model.

In any implementations, the processor may be configured to create a plurality of anatomical makeup classifications based on a plurality of predefined modes within the statistical shape model that characterize anatomical differences within the representative patient population and a plurality of standard deviations of anatomical variances contained within each of the plurality of predefined modes. The processor may be configured to assign the anatomical makeup classifications to the bone models. The storage system may be configured to store the anatomical makeup classifications.

In any implementations, the processor may be configured to select the first representative bone model in response to varying one or more of the predefined modes.

In any implementations, the processor may be configured to assign the anatomical makeup classification associated with the first representative bone model to the first patient bone model. The processor may be configured to assign the anatomical makeup classification associated with the second representative bone model to the second patient bone model.

The processor may be configured to perform a range of motion simulation for the assigned anatomical makeup classification.

In any implementations, the predefined modes may include a posture mode associated with posture. The processor may be configured to assign the anatomical makeup classifications to the bone models based on the posture mode. The processor may be configured to determine one or more posture parameters associated with a posture of the patient based on the anatomical makeup classification associated with the first representative bone model and/or the second representative bone model.

In any implementations, the processor may be configured to establish an implant plan based on the one or more posture parameters.

A computer implemented surgical planning method according to an implementation may include accessing a first patient bone model of a patient from memory. The first patient model may be associated with a first bone of a patient. The method may include accessing a second patient bone model of the patient from the memory. The second patient bone model may be associated with a second bone of the patient. The method may include selecting an anatomical model from a plurality of anatomical models based on the first patient bone model and the second patient bone model. The plurality of anatomical models may be associated with one or more bones and/or one or more joints of a representative patient population that may include at least the first bone and the second bone. The method may include determining one or more characteristics associated with a posture of the patient based on the selected anatomical model.

In any implementations, the step of selecting the anatomical model may occur in response to at least partially fitting the anatomical model to the first and second patient bone models.

In any implementations, the method may include establishing an implant plan associated with the first bone and/or the second bone of the patient in response to the step of determining the one or more characteristics.

In any implementations, the method may include analyzing the representative patient population within a statistical shape model.

In any implementations, the method may include identifying a plurality of predefined modes within the statistical shape model of the representative patient population. The predefined modes may include a posture mode associated with posture. The method may include establishing a plurality of standard deviations of anatomical variances contained within each of the plurality of predefined modes. The step of selecting the anatomical model may occur in response to varying one or more of the predefined modes within the statistical shape model.

A surgical planning system according to an implementation may include a processor and memory operably coupled to the processor. The processor may be configured to receive image data including first and second two-dimensional images of first and second bones of a patient. The processor may be configured to determine a first profile of the first and second bones along a first reference plane associated with the first image. The processor may be configured to determine a second profile of the first and second bones along a second reference plane associated with the second image. The processor may be configured to determine an orientation of the first and second bones based on a representative anatomical model associated with another patient, which may include projecting a first silhouette of the representative anatomical model onto the first profile along the first reference plane, and which may include projecting a second silhouette of the representative anatomical model onto the second profile along the second reference plane. The processor may be configured to determine one or more posture characteristics associated with a posture of the patient based on the determined orientation. The processor may be configured to establish a surgical plan associated with the first bone and/or the second bone based on the one or more posture characteristics.

In any implementations, the processor may be configured to determine a first acquisition orientation associated with the first image based on comparing a fit between the first silhouette and the first profile. The processor may be configured to determine a second acquisition orientation associated with the second image based on comparing a fit between the second silhouette and the second profile. The processor may be configured to determine the one or more posture characteristics based on the first acquisition orientation and the second acquisition orientation.

In any implementations, the processor may be configured to determine the first acquisition orientation in response to iteratively adjusting a projection of the first silhouette onto the first profile along the first reference plane. The processor may be configured to determine the second acquisition orientation in response to iteratively adjusting a projection of the second silhouette onto the second profile along the second reference plane.

In any implementations, the first reference plane and the second reference plane may be perpendicular to each other.

In any implementations, the first bone may be associated with a scapula of the patient. The second bone may be associated with a humerus of the patient.

A surgical planning system according to an implementation may include a processor operably connected to memory. The processor may be configured to access a first representative three-dimensional bone model from the memory. The first bone model may be associated with a first bone. The processor may be configured to access a partial three-dimensional bone model of the first bone of a patient. The partial bone model may be representative of a lesser portion of the first bone than the first representative bone model. The processor may be configured to at least partially register the partial bone model of the first bone to the first bone model to establish a registered position of the first bone model.

In any implementations, the processor may be configured to establish an implant plan in response to establishing the registered position of the first bone model.

In any implementations, the processor may be configured to determine one or more posture parameters associated with a posture of the patient based on the registered position of the first bone model. The processor may be configured to establish an implant plan based on the one or more posture parameters.

In any implementations, the processor may be configured to receive image data associated with the patient that omits a portion of the first bone. The processor may be configured to generate the partial bone model based on the image data.

In any implementations, the first bone may be a humerus. The partial bone model may omit a distal portion of the humerus. The first bone model may include the distal portion of the humerus.

In any implementations, the processor may be configured to determine an axis associated with the first bone based on the registered position of the first bone model.

A surgical planning system according to an implementation may include a processor operably connected to a storage system. The storage system may be configured to store a plurality of three-dimensional bone models associated with one or more bones and/or one or more joints of a representative patient population. The processor may be configured to select a first representative three-dimensional bone model from a first set of the bone models associated with a first bone of the representative patient population. The processor may be configured to at least partially register a partial three-dimensional bone model of the first bone of a patient to the first representative bone model. The partial bone model may be representative of a lesser portion of the first bone than the first bone model.

In any implementations, the processor may be configured to receive image data associated with the patient that may omit a portion of the first bone. The processor may be configured to generate the partial bone model based on the image data.

In any implementations, the partial bone model may be associated with a long bone. The partial bone model may include a diaphysis portion associated with a diaphysis of the long bone and a head portion associated with a head of the long bone. The processor may be configured to at least partially register the diaphysis portion of the partial bone model to a diaphysis portion of the first representative bone model. The processor may be configured to substantially align a center point of the head portion of the partial bone model with a center point of a head portion of the first representative bone model. The processor may be configured to rotate the head portion of the partial bone model about the respective center point to at least partially register the partial bone model to the first representative bone model.

In any implementations, the processor may be configured to select a second representative three-dimensional bone model from a second set of the bone models associated with a second bone. The processor may be configured to at least partially register the second representative bone model to a second three-dimensional bone model of the second bone of the patient to establish a registered position of the second representative bone model. The processor may be configured to select the first representative bone model from the first set of the bone models based on the registered position of the second representative bone model.

In any implementations, the first bone and the second bone may be adjoining bones.

In any implementations, the processor may be configured to analyze the representative patient population within a statistical shape model.

In any implementations, the processor may be configured to create a plurality of anatomical makeup classifications based on a plurality of predefined modes within the statistical shape model that characterize anatomical differences within the representative patient population and a plurality of standard deviations of anatomical variances contained within each of the plurality of predefined modes. The processor may be configured to assign the anatomical makeup classifications to the bone models. The storage system may be configured to store the anatomical makeup classifications.

In any implementations, the processor may be configured to select the first representative bone model and/or the second representative bone model in response to varying one or more of the predefined modes.

In any implementations, the processor may be configured to establish an implant plan in response to registering the partial bone model to the first representative bone model.

In any implementations, the partial bone model and the second bone model may be associated with an anatomical model of the patient. The first and second representative bone models may be associated with a representative anatomical model of another patient. The processor may be configured to select the representative anatomical model from a set of anatomical models associated with the first bone and the second bone. The processor may be configured to at least partially register the representative anatomical model to the anatomical model of the patient.

In any implementations, the processor may be configured to select the representative anatomical model in response to determining a minimum volume deviation within a first set of volume deviations. The first set of volume deviations may be established between the anatomical model of the patient and the respective representative anatomical models of the set of representative anatomical models in response to varying one or more of the predefined modes within the statistical shape model.

A computer implemented surgical planning method according to an implementation may include selecting a first representative three-dimensional bone model associated with a first bone. The method may include selecting a partial three-dimensional bone model of the first bone of a patient. The partial bone model may be representative of a lesser portion of the first bone than the first representative bone model. The method may include at least partially registering the partial bone model of the first bone to the first representative bone model to establish a registered position of the first representative bone model. The method may include analyzing the first bone based on the registered position of the first representative bone model.

In any implementations, the method may include establishing an implant plan based on the registered position of the first representative bone model.

In any implementations, the method may include accessing a plurality of three-dimensional bone models associated with one or more bones and/or one or more joints of a representative patient population. The method may include selecting the first representative bone model from a first set of the bone models associated with the first bone of the representative patient population.

In any implementations, the method may include selecting a second representative three-dimensional bone model from a second set of the bone models associated with a second bone of the representative patient population. The method may include at least partially registering the second representative bone model to a three-dimensional bone model of the second bone of the patient to establish a registered position of the second representative bone model. The method may include selecting the first representative bone model from the first set of the bone models in response to establishing the registered position of the second representative bone model.

In any implementations, the method may include analyzing the representative patient population within a statistical shape model.

In implementations, the method may include identifying a plurality of predefined modes within the statistical shape model of the representative patient population.

In any implementations, the method may include establishing a plurality of standard deviations of anatomical variances contained within each of the plurality of predefined modes. The step of selecting the first representative bone model and/or the second representative bone model may occur in response to varying one or more of the predefined modes within the statistical shape model.

In any implementations, the first bone may be a humerus. The second bone may be a scapula. The partial bone model may omit a distal portion of the humerus. The first representative bone model may include the distal portion of the humerus.

A surgical planning system according to an implementation may include a processor operably connected to memory. The processor may be configured to access a first three-dimensional bone model from the memory. The first bone model may be associated with a first bone. The processor may be configured to access a fragmentary three-dimensional bone model of the first bone of a patient. The fragmentary bone model may include one or more fragment portions associated with one or more respective fragments of the first bone. The processor may be configured to at least partially register the one or more fragment portions of the fragmentary bone model to a volume of the first bone model to establish a registered state of the fragmentary bone model.

In any implementations, the processor may be configured to establish an implant plan based on the registered state of the fragmentary bone model. The implant plan may be associated with at least one implant configured to secure one or more bone fragments.

In any implementations, the processor may be configured to receive image data associated with the patient. The processor may be configured to generate the fragmentary bone model based on the image data.

In any implementations, the first bone may be a long bone. The fragmentary bone model may include a diaphysis portion associated with a diaphysis of the long bone. The processor may be configured to at least partially register the diaphysis portion of the fragmentary bone model to a diaphysis portion of the first bone model to establish the registered state of the fragmentary bone model.

A surgical planning system according to an implementation may include a processor operably connected to a storage system. The storage system may be configured to store a plurality of three-dimensional bone models associated with one or more bones and/or one or more joints of a representative patient population. The processor may be configured to select a first three-dimensional bone model from a first set of the bone models associated with a first bone of the representative patient population. The processor may be configured to at least partially register one or more fragment portions of a fragmentary three-dimensional bone model of the first bone of a patient to the first bone model to establish a registered state of the fragmentary bone model. The one or more fragment portions may be associated with one or more respective fragments of the first bone.

In any implementations, the processor may be configured to establish an implant plan based on the registered state of the fragmentary bone model.

In any implementations, the processor may be configured to select a second three-dimensional bone model from a second set of the bone models associated with a second bone of the representative patient population. The processor may be configured to at least partially register the second bone model to a three-dimensional bone model of the second bone of the patient to establish a registered position of the second bone model. The processor may be configured to select the first bone model from the first set of the bone models in response to establishing the registered position of the second bone model.

In any implementations, the processor may be configured to analyze the representative patient population within a statistical shape model.

In any implementations, the processor may be configured to create a plurality of anatomical makeup classifications based on a plurality of predefined modes within the statistical shape model that characterize anatomical differences within the representative patient population and a plurality of standard deviations of anatomical variances contained within each of the plurality of predefined modes. The processor may be configured to assign the anatomical makeup classifications to the bone models. The storage system may be configured to store the anatomical makeup classifications.

In any implementations, the processor may be configured to establish an implant plan based on the registered state of the fragmentary bone model. The implant plan may be associated with at least one implant configured to secure one or more bone fragments.

In any implementations, the processor may be configured to select a second three-dimensional bone model from a second set of the bone models associated with a second bone of the representative patient population. The processor may be configured to at least partially register the second bone model to a three-dimensional bone model of the second bone of the patient to establish a registered position of the second bone model. The processor may be configured to select the first bone model from the first set of the bone models based on the registered position of the second bone model.

In any implementations, the first bone may be a humerus.

In any implementations, the one or more fragments may be associated with a proximal portion of the humerus.

A computer implemented surgical planning method according to an implementation may include selecting a first three-dimensional bone model associated with a first bone. The method may include selecting a fragmentary three-dimensional bone model of the first bone of a patient. The fragmentary bone model may include one or more fragment portions associated with one or more respective fragments of the first bone. The method may include at least partially registering the one or more fragment portions of the fragmentary bone model to a volume of the first bone model to establish a registered state of the fragmentary bone model. The method may include analyzing the first bone based on the registered state of the fragmentary bone model.

In any implementations, the method may include establishing an implant plan based on the registered state of the fragmentary bone model, which may include positioning at least one implant model adjacent to the one or more fragment portions of the fragmentary bone model in the registered state.

In any implementations, the first bone may be a long bone. The fragmentary bone model may include a diaphysis portion associated with a diaphysis of the long bone. The method may include at least partially registering the diaphysis portion of the fragmentary bone model to a diaphysis portion of the first bone model to establish the registered state of the fragmentary bone model.

In any implementations, the method may include accessing a plurality of three-dimensional bone models associated with one or more bones and/or one or more joints of a representative patient population. The method may include selecting the first bone model from a first set of the bone models associated with the first bone of the representative patient population.

In any implementations, the method may include selecting a second three-dimensional bone model from a second set of the bone models associated with a second bone of the representative patient population. The method may include at least partially registering the second bone model to a bone model of the second bone of the patient to establish a registered position of the second bone model. The method may include selecting the first bone model from the first set of the bone models in response to establishing the registered position of the second bone model.

In any implementations, the method may include analyzing the representative patient population within a statistical shape model.

In any implementations, the method may include identifying a plurality of predefined modes within the statistical shape model of the representative patient population. The method may include establishing a plurality of standard deviations of anatomical variances contained within each of the plurality of predefined modes. The step of selecting the first bone model may occur in response to varying one or more of the predefined modes within the statistical shape model.

FIG. 1 illustrates an exemplary surgical planning system 10 (hereinafter referred to as "the system 10"). The system 10 may be used for planning orthopaedic procedures, including pre-operatively, intra-operatively, and/or post-operatively to create, edit, review, refine, and/or execute surgical plans. The system 10 may be utilized for various orthopaedic and other surgical procedures, such as an arthroplasty to repair a joint, for example.

Shoulder arthroplasty may be periodically referenced throughout this disclosure to illustrate or emphasize certain features of the system 10. However, the teachings of this disclosure are not intended to be limited to any particular joint of the human musculoskeletal system and should therefore be understood as being applicable to the shoulder, knee, hip, ankle, wrist, etc. Moreover, the teachings of this disclosure are not intended to be limited to arthroplasty procedures and are therefore applicable to the repair of fractures and/or other deformities within the scope of this disclosure.

The system 10 may include, among other things, at least one host computer 12, one or more client computers 14, one or more imaging devices 16, a cloud-based storage system 18, and a network 20. The system 10 may include a greater or fewer number of subsystems within the scope of this disclosure.

The host computer 12 may be configured to execute one or more software programs. In some implementations, the host computer 12 may be more than one computer jointly configured to process software instructions serially or in parallel.

The host computer 12 may be in communication with the network 20, which itself may include one or more computing devices. The network 20 may be a private local area network (LAN), a private wide area network (WAN), the Internet, or a mesh network, for example.

The host computer 12 and each client computer 14 may include one or more of a computer processor, memory, storage means, network device and input and/or output devices and/or interfaces. The input devices may include a keyboard, mouse, etc. The output devices may include a monitor, speakers, printers, etc. The memory may, for example, include UVPROM, EEPROM, FLASH, RAM, ROM, DVD, CD, a hard drive, or other computer readable medium that may store data and/or other information relating to the surgical planning and implementation techniques disclosed herein. The host computer 12 and each client computer 14 may be a desktop computer, laptop computer, smart phone, tablet, virtual machine, or any other computing device. The interfaces may facilitate communication with the other systems and/or components of the network 20.

Each client computer 14 may be configured to communicate with the host computer 12 either directly, such as via a direct client interface 22, or over the network 20. In other implementations, the client computers 14 are configured to communicate with each other directly via a peer-to-peer interface 24.

Each client computer 14 may be coupled to one or more of the imaging devices 16. Each imaging device 16 may be configured to capture or acquire one or more images 26 of patient anatomy residing within a scan field (e.g., window) of the imaging device 16. The imaging device 16 may be configured to capture or acquire two dimensional (2D) and/or three dimensional (3D) greyscale and/or color images 26. Various imaging devices 16 may be utilized, including but not limited to an X-ray machine, a computerized tomography (CT) machine, or a magnetic resonance imaging (MRI) machine, for obtaining one or more images 26 of a patient.

The client computers 14 may also be configured to execute one or more software programs, such as those associated with various surgical planning tools. Each client computer 14 may be operable to access and locally and/or remotely execute a planning environment 28 for creating, editing, executing, refining, and/or reviewing one or more surgical plans 36 during pre-operative, intra-operative and/or post-operative phases of a surgery. The planning environment 28 may be a standalone software package or may be incorporated into another surgical tool. The planning environment 28 may be configured to communicate with the host computer 12 either over the network 20 or directly through the direct client interface 22.

The planning environment 28 may be further configured to interact with one or more of the imaging devices 16 to capture or acquire images 26 of patient anatomy. The planning environment 28 may provide a display or visualization of one or more images 26, bone models 30, implant models 32, transfer models 34, and/or surgical plans 36 via one or more graphical user interfaces (GUI). Each image 26, bone model 30, implant model 32, transfer model 34, surgical plan 36, and other data and/or information may be stored in one or more files or records according to a specified data structure.

The planning environment 28 may include various modules for performing the desired planning functions. For example, as further discussed below, the planning environment 28 may include a data module for accessing, retrieving, and/or storing data concerning the surgical plans 36, a display module for displaying the data (e.g., within one or more GUIs), a spatial module for modifying the data displayed by the display module, and a comparison module for determining one or more relationships between selected bone models and selected implant models. However, a greater or fewer number of modules may be utilized, and/or one or more of the modules may be combined to provide the disclosed functionality.

The storage system 18 may be operable to store or otherwise provide data from/to other computing devices, such as the host computer 12 and/or the one or more client computers 14, of the system 10. The storage system 18 may be a storage area network device (SAN) configured to communicate with the host computer 12 and/or the client computers 14 over the network 20, for example. Although shown as a separate device of the system 10, the storage system 18 may in some implementations be incorporated within or directly coupled to the host computer 12 and/or client computers 14. The storage system 18 may be configured to store one or more of computer software instructions, data, database files, configuration information, etc.

In some implementations, the system 10 may be a client-server architecture configured to execute computer software on the host computer 12, which may be accessible by the client computers 14 using either a thin client application or a web browser that can be executed on the client computers 14. The host computer 12 may load the computer software instructions from local storage, or from the storage system 18, into memory and may execute the computer software using the one or more computer processors.

The system 10 may further include one or more databases 38. The databases 38 may be stored at a central location, such as on the storage system 18. In another implementation, one or more databases 38 may be stored at the host computer 12 and/or may be a distributed database provided by one or more of the client computers 14. Each database 38 may be a relational database configured to associate one or more images 26, bone models 30, implant models 32, and/or transfer models 34 to each other and/or to a respective surgical plan 36. Each surgical plan 36 may be associated with the anatomy of a respective patient. Each image 26, bone model 30, implant model 32, transfer model 34, and surgical plan 36 may be assigned a unique identifier or database entry for storage on the storage system 18. Each database 38 may be configured to store data and other information corresponding to the images 26, bone models 30, implant models 32, transfer models 34, and surgical plans 36 in one or more database records or entries, and/or may be configured to link or otherwise associate one or more files corresponding to each respective image 26, bone model 30, implant model 32, transfer model 34, and surgical plan 36. The various data stored in the database(s) 38 may correspond to respective patient anatomies from prior surgical cases, and may be arranged into one or more predefined categories such as sex, age, ethnicity, defect category, procedure type, anatomical makeup classification, surgeon, facility or organization, etc.

Each image 26 and bone model 30 may include data and other information obtained from one or more medical devices or tools, such as the imaging devices 16. The bone models 30 may include one or more digital images and/or coordinate information relating to an anatomy of the patient obtained or derived from image(s) 26 captured or otherwise obtained by the imaging device(s) 16.

Each implant model 32 and transfer model 34 may include coordinate information associated with a predefined design or a design established or modified by the planning environment 28. The predefined design may correspond to one or more components. The planning environment 28 may incorporate and/or interface with one or more modeling packages, such as a computer aided design (CAD) package, to render the models 30, 32, and 34 as two-dimensional (2D) and/or three-dimensional (3D) volumes or constructs, which may overlay one or more of the images 26 in a display screen of a GUI.

The implant models 32 may correspond to implants and components of various shapes and sizes. Each implant may include one or more components that may be situated at a surgical site including screws, anchors, grafts, etc. Each implant model 32 may correspond to a single component or may include two or more components that may be configured to establish an assembly. Each implant and associated component(s) may be formed of various materials, including metallic and/or non-metallic materials. Each bone model 30, implant model 32, and transfer model 34 may correspond to 2D and/or 3D geometry, and may be utilized to generate a wireframe, mesh, and/or solid construct in a GUI.

Each surgical plan 36 may be associated with one or more of the images 26, bone models 30, implant models 32, and/or transfer models 34. The surgical plan 36 may include various parameters associated with the images 26, bone models 30, implant models 32, and/or transfer models 34. For example, the surgical plan 36 may include parameters relating to bone density and bone quality associated with patient anatomy captured in the image(s) 26. The surgical plan 36 may include parameters including spatial information relating to relative positioning and coordinate information of the selected bone model(s) 30, implant model(s) 32, and/or transfer model(s) 34.

The surgical plan 36 may define one or more revisions to a bone model 30 and information relating to a position of an implant model 32 and/or transfer model 34 relative to the original and/or revised bone model 30. The surgical plan 36 may include coordinate information relating to the revised bone model 30 and a relative position of the implant model 32 and/or transfer model 34 in one or more predefined data structure(s). The planning environment 28 may be configured to implement one or more revisions to the various models, either automatically or in response to user interaction with the user interface(s). Revisions to each bone model 30, implant model 32, transfer model 34, and/or surgical plan 36 may be stored in one or more of the databases 38, either automatically and/or in response to user interaction with the system 10.

One or more surgeons and/or other staff users may be presented with the planning environment 28 via the client computers 14 and may simultaneously access each image 26, bone model 30, implant model 32, transfer model 34, and surgical plan 36 stored in the database(s) 38. Each user may interact with the planning environment 28 to create, view, refine, and/or modify various aspects of the surgical plan 36. Each client computer 14 may be configured to store local instances of the images 26, bone models 30, implant models 32, transfer models 34, and/or surgical plans 36, which may be synchronized in real-time or periodically with the database(s) 38. The planning environment 28 may be a standalone software package executed on a client computer 14 or may be provided as one or more web-based services executed on the host computer 12, for example.

The system 10 described above may be configured for preoperatively planning surgical procedures. The preoperative planning provided by the system 10 may include, but is not limited to, features such as constructing a virtual model of a patient's anatomy, classifying the virtual model, identifying landmarks within the virtual model, selecting and orienting virtual implants within the virtual model, etc.

Figure 2:
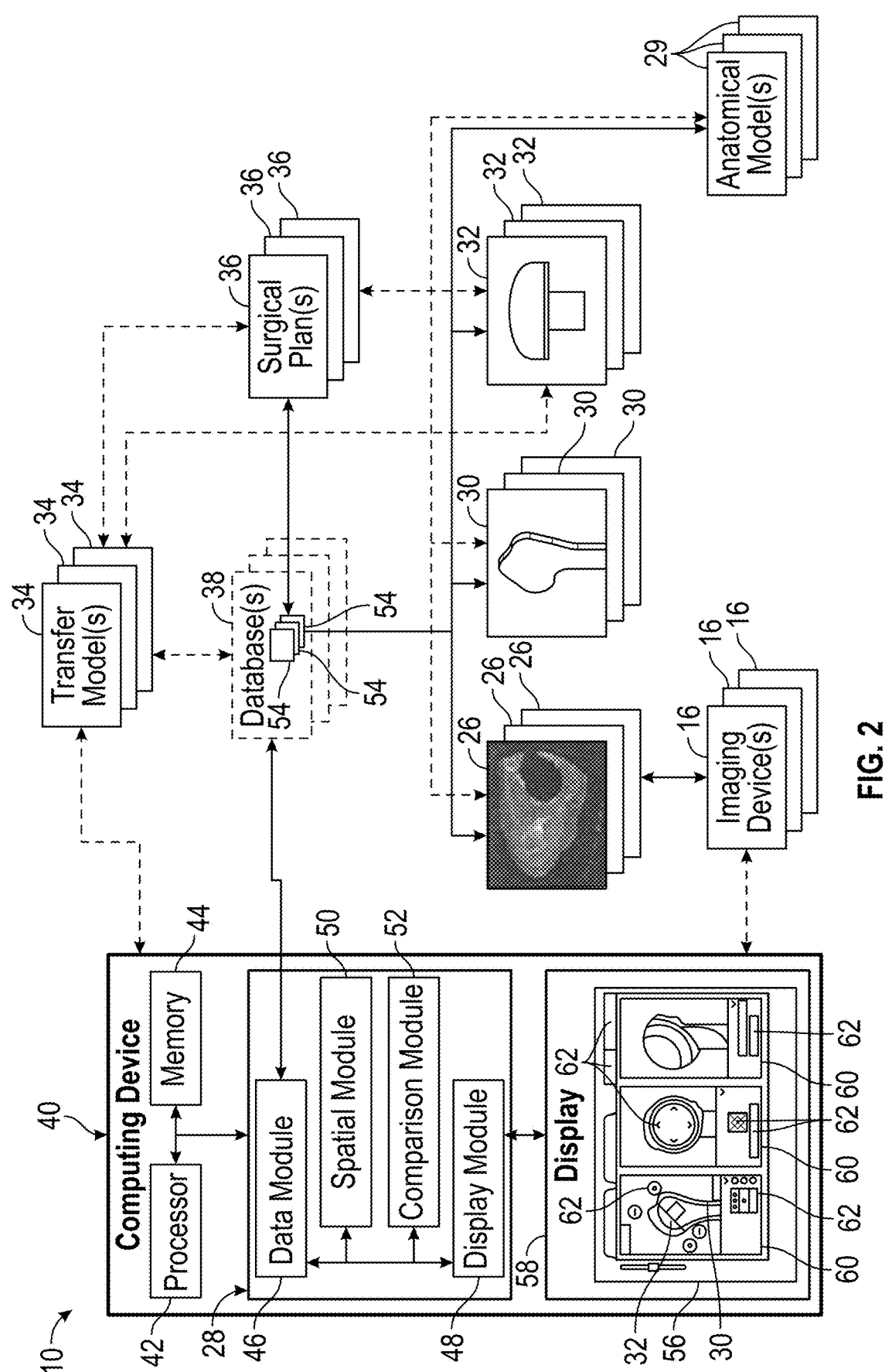
FIG. 2 schematically illustrates exemplary aspects of the surgical planning system of FIG. 1.

Referring now to FIG. 2, with continuing reference to FIG. 1, the system 10 may include a computing device 40 including at least one processor 42 operably coupled to a memory 44 capable of storing computer executable instructions. The computing device 40 may be considered representative of any of the computing devices disclosed herein, including but not limited to the host computer 12 and/or the client computers 14. The processor 42 may be configured to execute one or more of the planning environments 28 for creating, editing, executing, refining, and/or reviewing one or more surgical plans 36 and any associated bone models 30, implant models 32, and transfer models 34 during pre-operative, intra-operative, and/or post-operative phases of a surgery.

The processor 42 can be a custom made or commercially available processor, central processing unit (CPU), or generally any device for executing software instructions. The memory 44 can include any one or combination of volatile memory elements and/or nonvolatile memory elements. The processor 42 may be operably coupled to the memory 44 and may be configured to execute one or more programs stored in the memory 44 based on various inputs received from other devices or data sources.

The planning environment 28 may include at least a data module 46, a display module 48, a spatial module 50, and a comparison module 52. Although four modules are shown, it should be understood that a greater or fewer number of modules could be utilized, and/or further that one or more of the modules could be combined to provide the disclosed functionality.

The data module 46 may be configured to access, retrieve, and/or store data and other information in the database(s) 38 corresponding to one or more images 26 of patient anatomy, bone model(s) 30, implant model(s) 32, transfer model(s) 34, and/or surgical plan(s) 36. The data and other information may be stored in one or more databases 38 as one or more records or entries 54. In some implementations, the data and other information may be stored in one or more files that are accessible by referencing one or more objects or memory locations referenced by the entries 54.

The memory 44 may be configured to access, load, edit, and/or store instances of one or more images 26, bone models 30, implant models 32, transfer models 34, and/or surgical plans 36 in response to one or more commands from the data module 46. The data module 46 may be configured to cause the memory 44 to store a local instance of the image(s) 26, bone model(s) 30, implant model(s) 32, transfer model(s) 34, and/or surgical plan(s) 36, which may be synchronized with the entries 54 stored in the database(s) 38.

The data module 46 may be configured to receive data and other information corresponding to at least one or more images 26 of patient anatomy from various sources, such as the imaging device(s) 16, for example. The data module 46 may be further configured to command the imaging device 16 to capture or acquire the images 26 automatically or in response to user interaction.

The display module 48 may be configured to display data and other information relating to one or more surgical plans 36 in at least one graphical user interface (GUI) 56, including one or more of the images 26, bone models 30, implant models 32, and/or transfer models 34. The computing device 40 may incorporate or be coupled to a display device 58. The display module 48 may be configured to allow the display device 58 to display information in the user interface 56. A surgeon or other user may interact with the user interface 56 within the planning environment 28 to view one or more images 26 of patient anatomy and/or any associated bone models 30, implant models 32, and transfer models 34. The surgeon or other user may interact with the user interface 56 via the planning environment 28 to create, edit, execute, refine, and/or review one or more surgical plans 36.

The user interface 56 may include one or more display windows 60 and one or more objects 62 that may be presented within the display windows 60. The display windows 60 may include any number of windows, and the objects 62 may include any number of objects within the scope of this disclosure.

A surgeon or user may interact with the user interface 56, including the objects 62 and/or display windows 60, to retrieve, view, edit, store, etc., various aspects of a respective surgical plan 36, which may include information from the selected image(s) 26, bone model(s) 30, implant model(s) 32 and/or transfer model(s) 34. The objects 62 may include graphics such as menus, tabs, buttons, drop-down lists, directional indicators, etc. The objects 62 may be organized in one or more menu items associated with the respective display windows 60. Geometric objects, including selected image(s) 26, bone model(s) 30, implant model(s) 32, transfer model(s) 34, and/or other information relating to the surgical plan 36, may be displayed in one or more of the display windows 60. Each transfer model 34 may include one or more surgical instruments used to implant a selected implant as part of the surgical plan 36.

The surgeon may interact with the objects 62 to specify various aspects of the surgical plan 36. For example, the surgeon may select one of the tabs to view or specify aspects of the surgical plan 36 for one portion of a joint, such as a glenoid, for example, and may select another one of the tabs to view or specify aspects of the surgical plan 36 for another portion of the joint, such as a humerus, for example. The surgeon make further take various measurements (e.g., linear, angular, tissue density, etc.) of the joint as part specifying aspects of the surgical plan 36.

The surgeon may interact with the menu items to select and specify various aspects of the bone models 30, implant models 32, and/or transfer models 34 from the database 38. For example, the display module 48 may be configured to display one or more bone models 30 together with the respective image(s) 26 of the patient anatomy and implant models 32 selected in response to user interaction with the user interface 56. The user may interact with the drop-down lists of the objects 62 within the display windows 60 to specify implant type, resection angle, and implant size. The resection angle menu item may be further associated with a resection plane.

The user may also interact with various buttons to change (e.g., increase or decrease) a resection angle. The user may interact with buttons adjacent the selected implant model 32 to change (e.g., increase or decrease) a size of a component of the selected implant model 32. The buttons may be overlaid onto or may be situated adjacent to the display windows 60.

The user may further interact with directional indicators to move a portion of the selected implant model 32 in different directions (e.g., up, down, left, right) in one of the display windows 60. The surgeon may drag or otherwise move the selected implant model 32 to a desired position in the display window 60 utilizing a mouse or other input device, for example. The surgeon may interact with one of the drop-down lists to specify a type and/or size of a component of the selected implant model 32.

The display module 48 may be configured to superimpose one or more of the bone models 30, the implant models 32, and the transfer models 34 over one or more of the images 26 within one or more of the display windows 60. The implant model 32 may include one or more components that establish an assembly. At least a portion of the implant model 32 may be configured to be at least partially received in a volume of a selected one of the bone models 30. In some implementations, the implant model 32 may have an articulation surface dimensioned to mate with an articular surface of an opposed bone or implant.

The display windows 60 may be configured to display the images 26, bone models 30, implant models 32, and/or transfer models 34 at various orientations. The display module 48 may be configured to display two dimensional (2D) representation(s) of the selected bone model(s) 30, implant model(s) 32, and/or transfer model(s) 34 in the some of the display windows 60, and may be configured to display 3D representation(s) of the selected bone model 30, implant model 32, and/or transfer model(s) 34 in another of the display windows 60, for example. The surgeon may interact with the user interface 56 to move (e.g., up, down, left, right, rotate, etc.) the selected bone model 30, selected implant model 32, and/or selected transfer model 34 in 2D space and/or 3D space. Other implementations for displaying 2D and/or 3D representations in the various display windows 60 are further contemplated within the scope of this disclosure.

The display module 48 may be further configured such that the selected image(s) 26, bone model(s) 30, implant model(s) 32, and/or transfer model(s) 34 may be selectively displayed and hidden (e.g., toggled) in one or more of the display windows 60 in response to user interaction with the user interface 56, which may provide the surgeon with enhanced flexibility in reviewing aspects of the surgical plan 36. For example, the surgeon may interact with drop-down lists of the objects 62 to selectively display and hide components of the selected implant model 32 in one of the display windows 60.

The selected bone model 30 may correspond to a bone associated with a joint, including any of the exemplary joints disclosed herein. The display module 48 may be configured to display a sectional view of the selected bone model 30 and selected implant model 32 in one or more of the display windows 60, for example. The sectional view of the bone model(s) 30 may be presented or displayed together with the associated image(s) 26 of the patient anatomy.

The spatial module 50 may be configured to establish one or more resection planes along the selected bone model 30. A volume of the selected implant model 32 may be at least partially received in a volume of the selected bone model 30 along the resection plane(s). The resection plane(s) may be defined by a resection angle.

The spatial module 50 may be further configured to cause the display module 48 to display an excised portion of the selected bone model 30 to be displayed in one of the display windows 60 in a different manner than a remainder of the bone model 30 on an opposed side of the resection plane. For example, the excised portion of the bone model 30 may be hidden from display in the display window 60 such that the respective portion of the 26 of the patient anatomy is shown. In other implementations, the excised portion of the selected bone model 30 may be displayed in a relatively darker shade. The spatial module 50 may determine the excised portion by comparing coordinates of the bone model 30 with respect to a position of the resection plane, for example. The user may interact with one or more buttons of the objects 62 to toggle between a volume of previous and revised (e.g., resected) states of the selected bone model 30.

The planning environment 28 may be further configured such that changes in one of the display windows 60 are synchronized with each of the other windows 60. The changes may be synchronized between the display windows 60 automatically and/or manually in response to user interaction.

The surgeon may utilize various instrumentation and devices to implement each surgical plan 36, including preparing the surgical site and securing one or more implants to bone or other tissue to restore functionality to the respective joint. Each of the transfer models 34 may be associated with a respective surgical instrument or device (e.g., transfer guides, etc.) or a respective implant model 32.

The surgical plan 36 may be associated with one or more positioning objects such as a guide pin (e.g., guide wire or Kirschner wire) dimensioned to be secured in tissue to position and orient the various instrumentation, devices and/or implants. The display module 48 may be configured to display a virtual position and virtual axis in one or more of the display windows 60. The virtual position may be associated with a specified position of the positioning object relative to the patient anatomy (as represented by the image(s) 26). The virtual axis may extend through the virtual position and may be associated with a specified orientation of the positioning object relative to the patient anatomy. The spatial module 50 may be configured to set the virtual position and/or virtual axis in response to placement of a respective implant model 32 relative to the bone model 30 and associated patient anatomy. The virtual position and/or virtual axis may be set and/or adjusted automatically based on a position and orientation of the selected implant model 32 relative to the selected bone model 30 and/or in response to user interaction with the user interface 56.

The spatial module 50 may be further configured to determine one or more collision or contact points associated with the patient anatomy. The contact points may be associated with one or more landmarks or other surface features along the bone model 30 and/or other portions of the patient anatomy. Each contact point may be established along an articular surface or non-articular surface of a joint. The spatial module 50 may be configured to set the contact points based on the virtual position, virtual axis, and/or position and orientation of the respective implant model 32 relative to the patient anatomy. The spatial module 50 may be configured to cause the display module 48 to display the contact points in one or more of the display windows 60. In some implementations, the contact points may be set and/or adjusted automatically based on a position of the implant model 32 and/or in response to user interaction with the user interface 56. The virtual position, virtual axis, and/or contact points may be stored in one or more entries 54 in the database 38 and may be associated with the respective surgical plan 36.

The comparison module 52 may be configured to generate or set one or more parameters associated with implementing the surgical plan 36. The parameters may include one or more settings or dimensions associated with the respective transfer models 34. The parameters may be based on the virtual position, virtual axis, and/or contact points. The comparison module 52 may be configured to determine one or more settings or dimensions associated with the respective transfer models 34 relative to the patient anatomy, bone model(s) 30, implant model(s) 32, virtual position, virtual axis, and/or contact points CP. The dimensions and settings may be utilized to form a physical instance of each respective transfer model 34. The settings may be utilized to specify a position and orientation of each respective transfer model 34 relative to the implant model 32 and/or bone model 30. The settings may be utilized to configure one or more transfer members (e.g., objects) and related instrumentation or devices associated with the transfer model 34. The comparison module 52 may be configured to generate the settings and/or dimensions such that the transfer model 34 contacts one or more predetermined positions at or along the bone model 30 or patient anatomy in an installed position when coupled to the respective implant model 32. The predetermined positions may include one or more of the contact points. The settings and dimensions may be communicated utilizing various techniques, including one or more graphics in the user interface 56 or output files. The settings and/or dimensions may be stored in one or more entries 54 in the database 38 associated with the transfer models 34.

The user may interact with a list of the objects 62 associated with one of the display windows 60 to select a desired transfer model 34 from the database 38. The display module 48 may be configured to display the selected transfer model 34 in the display windows 60 at various positions and orientations. The spatial module 50 may be configured to set an initial position of the selected transfer model 34 according to the virtual position, virtual axis, and/or contact points.

The user may interact with the user interface 56 to set or adjust a position and/or orientation of the selected transfer model 34. The user may interact with directional indicators of the objects 62 to move the selected transfer model 34 and/or virtual position in different directions (e.g., up, down, left, right) in the display windows 60. The surgeon may drag or otherwise move the selected transfer model 34 and/or virtual position to a desired position in the display windows 60 utilizing a mouse or other input device, for example. The user may interact with rotational indicators of the objects to adjust a position and/or orientation of the transfer model 34 about the virtual axis relative to the selected bone model 30 and/or implant model 32. The user may interact with tilt indicators of the objects 62 to adjust an orientation of the selected transfer model 34 and associated virtual axis at the virtual position relative to the selected bone model 30 and/or implant model 32. The user may interact with other buttons and/or directional indicators to cause the transfer model 34 to articulate or otherwise move. The transfer model 34 may be articulated or otherwise moved independently or synchronously, which may occur manually in response to user interaction and/or automatically in response to situating the transfer model 34 relative to the bone model 30 and/or implant model 32. Movement of the transfer model 34 may cause an automatic adjustment to the respective contact points.

Various transfer members may be utilized with the planning environment 28 to implement the surgical plan(s) 36. Each transfer member may be associated with a respective transfer model 34. The transfer members may be incorporated into transfer guides, implants, and/or assemblies to set a position and orientation of the respective implant prior to fixing or otherwise securing the implant at a surgical site.

Figure 3:
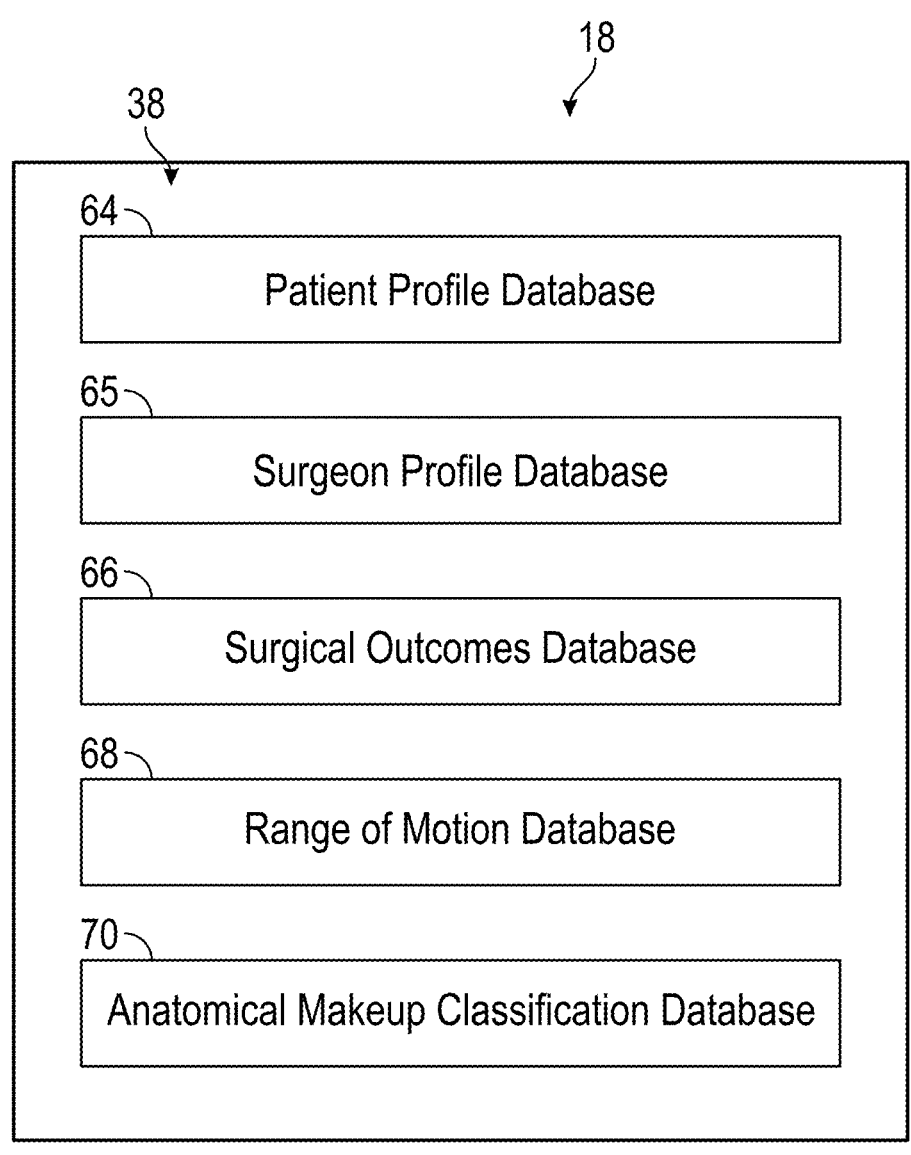
FIG. 3 schematically illustrates exemplary cloud-based databases that can be accessed by a surgical planning system.

Referring now to FIG. 3, with continued reference to FIG. 2, the computing device 40 including the processor 42 may be operably connected to storage system(s), such the storage system 18. The computing device 40 may interface with the storage system 18 over the network 20 for accessing various databases 38 stored thereon in order to establish and implement the surgical plans 36.

The databases 38 of the storage system 18 may include a patient profile database 64, a surgeon profile database 65, a surgical outcomes database 66, a range of motion database 68, and an anatomical makeup classification database 70. Additional databases could be stored on and accessed from the storage system 18 within the scope of this disclosure. Moreover, although shown as separate databases, one or more of the databases could be combined or linked together. For example, the anatomical makeup classification database 70 could be combined or linked with the surgical outcomes database 66, the range of motion database 68, or both.

The patient profile database 64 may include information that is part of an indexed and stored record or entry related to one or more current patients associated with the system 10. The information stored on the patient profile database 64 may include the sex, age, ethnicity, height, weight, defect category, procedure type, surgeon, facility or organization, dominant joint, acts of daily living/lifestyle goals profile (e.g., desired post-surgery range of motion for abduction, adduction, external rotation, internal rotation, extension, flexion, external rotation combined with 60° abduction, internal rotation with 60° abduction, etc.), current surgical plan information, etc. for each patient. The patient profile database 64 may further store or link to the images 26 for a given patient.

The surgeon profile database 65 may include information that is part of indexed and stored records or entries related to one or more surgeon users associated with the system 10. The information stored on the surgeon profile database 65 may include the surgeon's name, facility or organization, historical data concerning the types of prior surgeries planned by the surgeon using the system 10, data concerning the types of implants included in the surgeon's preoperative surgical plans, data concerning the actual implants utilized in the surgeon's prior surgeries, etc. In some implementations, the surgeon profile database 65 may interface with the patient profile database 64 for linking each surgeon from the surgeon profile database 65 to his/her patients listed in the patient profile database 64.

The surgical outcomes database 66 may include information that is part of indexed and stored records or entries related to one or more prior patients associated with the system 10. The surgical outcomes database 66 may be created based on information logged by surgeons and/or other staff users after performing each surgery and at each follow-up visit for indicating the progress of the prior patient. The information stored on the surgical outcomes database 66 may include the sex, age, ethnicity, height, weight, defect category, procedure type, specific implants used, surgeon, facility or organization, dominant joint, visual analog pain scores, ASES scores, achieved acts of daily living/lifestyle profile (e.g., achieved post-surgery range of motion for abduction, adduction, external rotation, internal rotation, extension, flexion, external rotation combined with 60° abduction, internal rotation with 60° abduction, etc.), surgical plan information, etc. for each prior patient. The surgical outcomes database 66 may additionally store or link to preoperative and postoperative images 26 for each prior patient.

The range of motion database 68 may include information that is part of indexed and stored records or entries related to one or more current and prior patients associated with the system 10. The range of motion database 68 may store range of motion data derived from range of motion simulations performed by the computing device 40 for each surgical plan 36. The range of motion data may include information related to simulated joint motions (e.g., abduction/adduction, flexion/extension, internal/external rotation, etc.), identified contact or collision points for various implant positions, angular arc and mode of collision (e.g., implant-to-implant, implant-to-bone, bone-to-bone, etc.) for various implant positions, adjusted center of rotation of implants in multiple increments and offset directions for various implant positions, etc.

The anatomical makeup classification database 70 may store a plurality of anatomical makeup classifications that characterize anatomical differences and variances within the anatomical differences within a representative patient population for one or more intended surgeries (e.g., total shoulder, reverse shoulder, etc.). In some implementations, the representative patient population may be derived by analyzing image data, such as images from the prior patients stored on the surgical outcomes database 66 and/or any other imaging source, associated with a plurality of prior patients who have already received the intended surgery. Each of the plurality of anatomical makeup classifications is a numerical classification of an anatomical makeup of a bone or a joint of the representative patient population.

Figure 4:
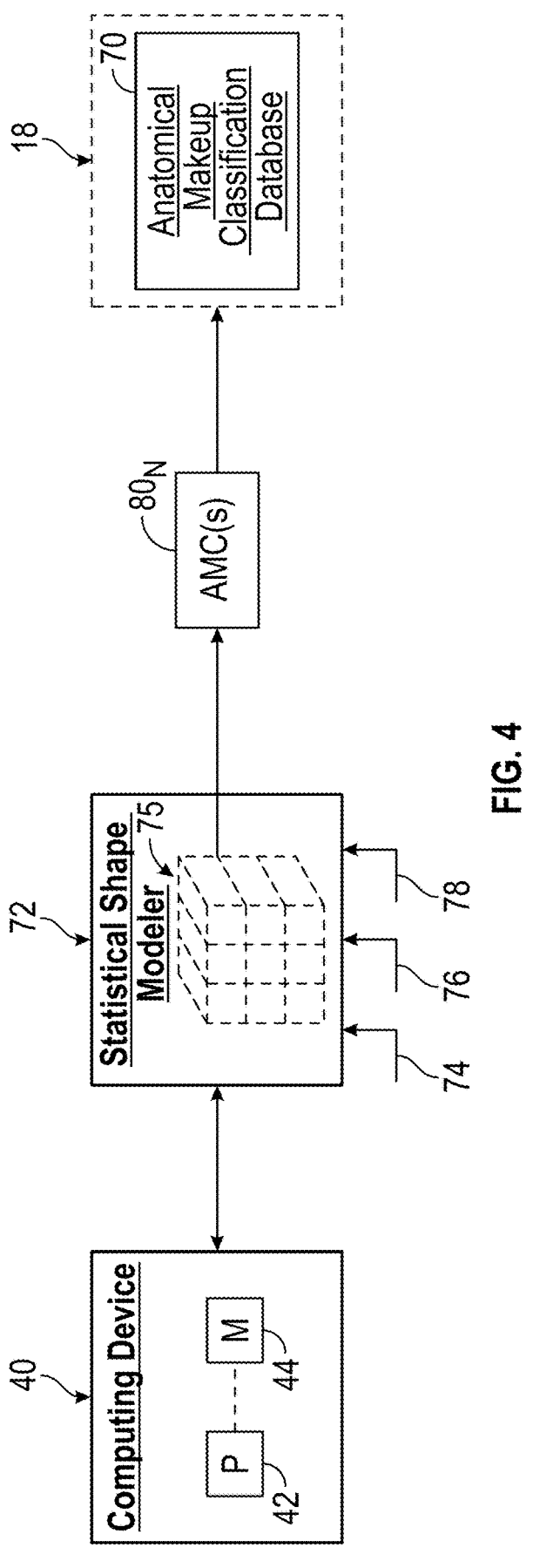
FIG. 4 schematically illustrates additional exemplary aspects of the surgical planning system of FIG. 1.

Referring now to FIG. 4, with continued reference to FIGS. 1-3, the computing device 40 may interface with a statistical shape modeler 72 for creating the anatomical makeup classification database 70. The statistical shape modeler 72 may be a software package stored in the memory 44 of the computing device 40 or in the storage system 18 and which may be executed by the processor 42.

The statistical shape modeler 72 may receive a plurality of sets of image data 74 associated with a bone or joint of interest. In some implementations, the sets of image data 74 is made up of tens of thousands of sets of image data. Each set of image data 74 may include 2D and/or 3D anatomical images specific to prior patients of a representative patient population for the bone or joint of interest and related to a given type of surgery. The statistical shape modeler 72 may analyze the plurality of sets of image data 74 for constructing a statistical shape model 75.

As an input, the statistical shape modeler 72 may receive a plurality of predefined modes 76 to be used for analyzing the plurality of sets of image data 74. Each of the modes 76 is a descriptor configured for characterizing anatomical differences in the bone or joint associated with the statistical shape model 75. Exemplary modes 76 that may be provided to the statistical shape modeler 72 may include but are not limited to size of glenoid, size of scapula, amount of inclination, amount of version, projected amount of glenoid and sagittal neck length, angle of glenoid relative to scapular neck, critical shoulder angle, projection of acromion and/or coracoid, size of humeral head, varus/valgus of humeral head, varus/valgus of femur and/or tibia, internal/external rotation of femur and/or tibia, integrity of subscapularis, deltoid, and/or supraspinatus, ML and AP width, intercondylar notch depth, tibial slope, Q-angle of the knee, ACL/PCL stability, MCL/LCL stability, amount of flexion, amount of extension, quality and amount of soft tissue surrounding joint, patellar tracking angle, bone density, bone quality subluxation percentage, anatomical landmarks, joint space, pre-operative range of motion, any combinations of the foregoing, etc.

In some implementations, at least seven different modes may be utilized by the statistical shape modeler 72 to characterize the statistical shape model 75. However, a greater or fewer number of modes may be provided within the scope of this disclosure.

In some implementations, the modes 76 may not be predefined. Rather, the statistical shape modeler 72 may be programmed to utilize artificial intelligence (e.g. a neural network) or machine learning to extrapolate the modes that best relate to the bone or joint being modeled within the statistical shape model 75.

As another input, the statistical shape modeler 72 may receive a plurality of predefined standard deviations 78 to be used for analyzing the plurality of sets of image data 74. Each standard deviation 78 may represent anatomical variances (e.g., distances between features, orientation of features, relative features, etc.) contained within each of the plurality of predefined modes 76. The standard deviations 78 may be used to validate a percentile coverage of the representative patient population that is represented within the statistical shape model 75. In some implementations, at least seven different standards of deviation (e.g., −3, −2, −1, 0, 1, 2, and 3) may be utilized by the statistical shape modeler 72 to further characterize all anatomical variances contained within the anatomies described within the statistical shape model 75. However, a greater or fewer number of standard deviations could be utilized within the scope of this disclosure.

The statistical shape modeler 72 may, in response to commands from the processor 42, combine the plurality of standard deviations 78 with the plurality of predefined modes 76 to assign a plurality of anatomical makeup classifications 80N, wherein N is any number, to the bone or joint associated with the statistical shape model 75 in order to categorize the anatomical makeup of the entire patient population represented within the statistical shape model 75. Each anatomical makeup classification 80N may then be saved in the anatomical makeup classification database 70 of the storage system 18.

Figure 5:
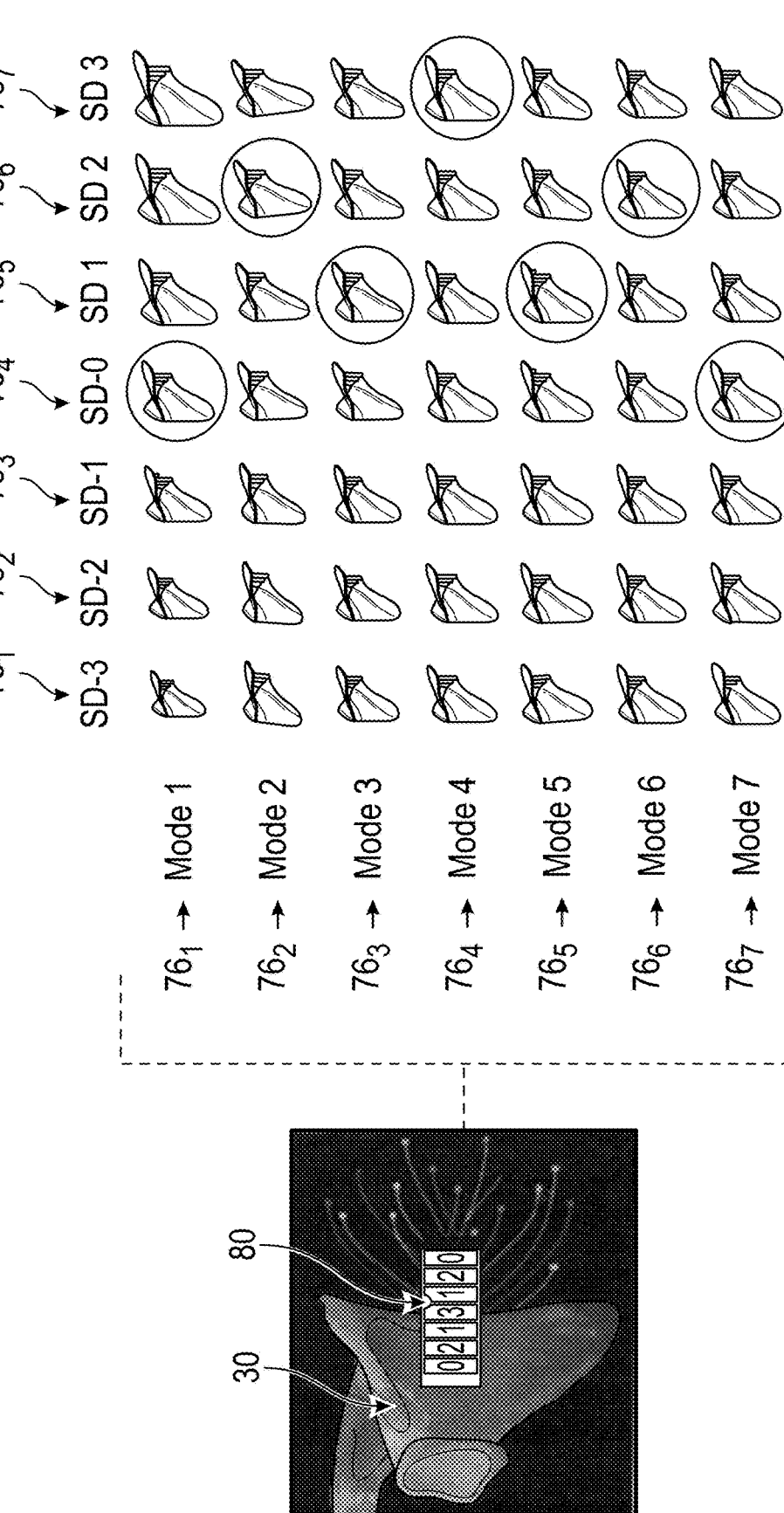
FIG. 5 schematically illustrates an exemplary anatomical makeup classification that can be assigned by a surgical planning system.

FIG. 5 illustrates an exemplary anatomic makeup classification 80 as assigned to a specific bone model 30 derived from the statistical shape model 75. In an embodiment, the bone model 30 is a 3D model of a scapula of a shoulder joint. However, other bones and joints could also be classified in a similar manner.

The statistical shape modeler 72 of FIG. 4 may analyze the bone model 30 in respect to each of a plurality of modes $76_1$ to $76_7$, in order to characterize any anatomical differences in the bone model 30 compared to the other similar bones/joints associated with the statistical shape model 75. Of course, a greater or fewer number of modes are possible.

The statistical shape modeler 72 may further characterize any anatomical variances contained within each of the plurality of predefined modes $76_1$-$76_7$ by analyzing each of the modes with respect to a plurality of standard deviations $78_1$-$78_7$. Of course, a greater or fewer number of standards of deviation are possible.

In the implementation shown in FIG. 5, the bone model 30 is assigned the numerical value 0213120 as its anatomical makeup classification 80. This numerical value represents a standard of deviation of 0 within the first mode $76_1$, a standard of deviation of 2 within the second mode $76_2$, a standard of deviation of 1 within the third mode $76_3$, a standard of deviation of 3 within the fourth mode $76_4$, a standard of deviation of 1 in the fifth mode 765, a standard of deviation of 2 within the sixth mode $76_6$, and a standard of deviation of 0 in the seventh mode $76_7$. The anatomical makeup classification 80 is a unique numeric identifier for describing the anatomy associated with the bone model 30.

FIG. 6, with continued reference to FIGS. 1-5, schematically illustrates a method 84 for creating the anatomical makeup classification database 70 described above. The method 84 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 84. In an exemplary implementation, the computing device 40 of the host computer 12 may be programmed to execute the method 84. However, other implementations are further contemplated within the scope of this disclosure.

A statistical shape model 75 that is representative of a patient population having pathologic anatomies associated with an intended surgery may be constructed at step 86. A plurality of modes 76 may be identified within the statistical shape model 75 at step 88. The modes 76 may characterize anatomical differences within the statistical shape model 75.

Next, at step 90, a plurality of standard deviations 78 of anatomical variances contained within each of the modes 76 may be established. The standard deviations 78 may be used to validate a percentile coverage of the representative patient population associated with the statistical shape model 75.

The standard deviations 78 may be combined with the modes 76 to create a plurality of unique anatomical makeup classifications 80 at step 92. At step 94, the anatomical makeup classifications 80 may be consolidated to form the anatomical makeup classification database 70. The anatomical makeup classification database 70 may therefore represent major variances within the representative patient population which may influence implant function.

As further part of the method 84, an appropriate sized implant model 32 may be selected and positioned to a default starting position and orientation relative to the bone or joint associated with each of the plurality of anatomical makeup classifications 80 at step 96. The default starting positions and orientations of the implant models 32 may therefore also be linked to and stored, at step 97, with the anatomical makeup classifications 80 as part of the anatomical makeup classification database 70.

Once built, the anatomical makeup classification database 70 may enable additional features, processes, and/or capabilities to be implemented within or executed by the system 10 for enhancing surgical planning. Example implementations of such features are detailed below.

Figure 7:
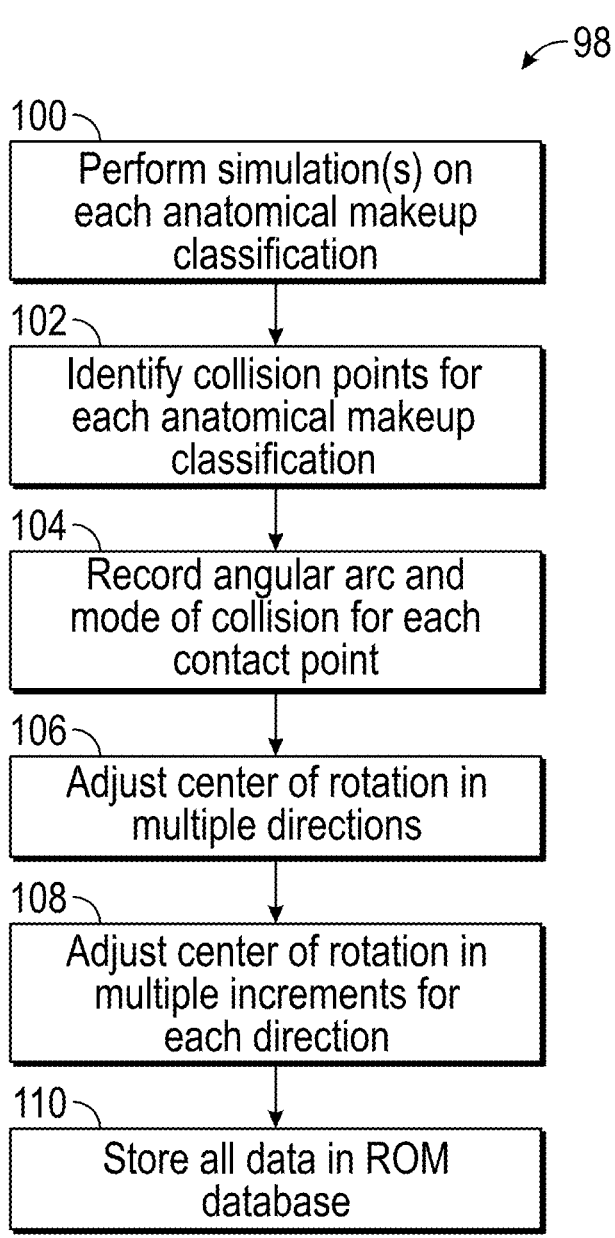
FIG. 7 schematically illustrates a method for establishing a range of motion database of a surgical planning system.

FIG. 7, for example, illustrates a method 98 for augmenting the range of motion database 68 with the information contained within the anatomical makeup classification database 70. The method 98 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 98. In an exemplary implementation, the computing device 40 of the host computer 12 may be programmed to execute the method 98. However, other implementations are further contemplated within the scope of this disclosure.

Figure 8:
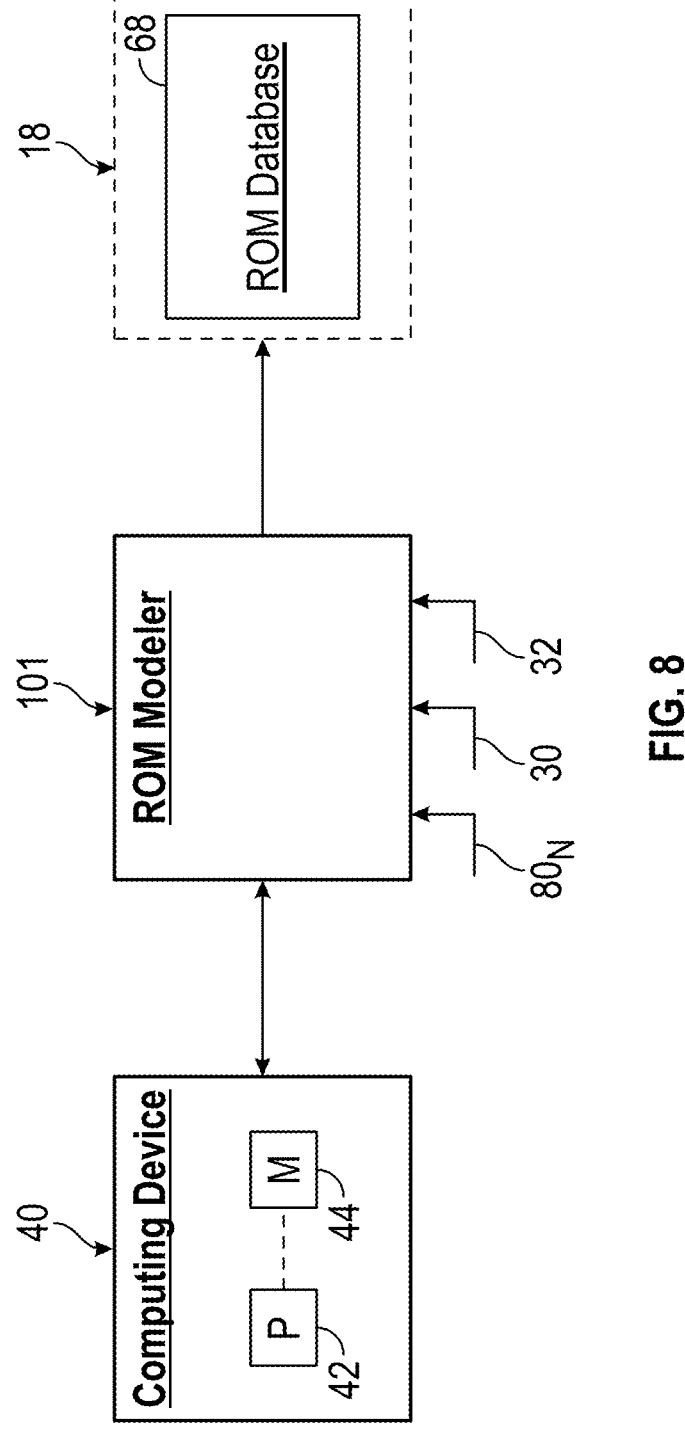
FIG. 8 schematically illustrates additional exemplary aspects of the surgical planning system of FIG. 1.

First, at step 100, one or more motion simulations may be performed on each anatomical makeup classification 80 stored on the anatomical makeup classification database 70. The motion simulations may be performed within a range of motion modeler 101, which may be a software package stored in the memory 44 of the computing device 40 or in the storage system 18 and which may be executed by the processor 42 (see, e.g., FIG. 8). The range of motion modeler 101 may receive each of the anatomical makeup classifications 80 (and each associated bone model 30 and implant model 32, including default implant starting positions and orientations) as inputs from the anatomical makeup classification database 70 when performing the motion simulations.

The range of motion simulations actually performed at step 100 will depend on the type of bone or joint being analyzed, among other criteria. Examples of the types of motions that can be simulated as part of step 100 of the method 98 include but are not limited to abduction/adduction, flexion/extension, internal/external rotation, etc.

Contact or collision points may be identified at step 102 for identifying the range of motion end points for each range of motion simulation performed on each anatomical makeup classification 80. The angular arc and mode of collision (e.g., implant-to-implant, implant-to-bone, bone-to-bone, etc.) for each contact point may be recorded at step 104.

The center of rotation of the implant models 32 positioned within the bone models 30 for each anatomical makeup classification 80 may be adjusted at step 106. In some implementations, this step may include adjusting each implant model 32 in at least three offset directions (e.g., medial, interior, and posterior) relative to the respective bone model 30 to simulation different positions of the implant models 32.

At step 108, the center of rotation of the implant model 32 for each anatomical makeup classification 80 may be adjusted relative to the respective bone model 30 in multiple increments for recording the angular arcs and collision modes associated with the adjusted positions. All range of motion data derived from the simulations performed at steps 100-108 may then be saved within the range of motion database 68 at step 110.

Figure 9:
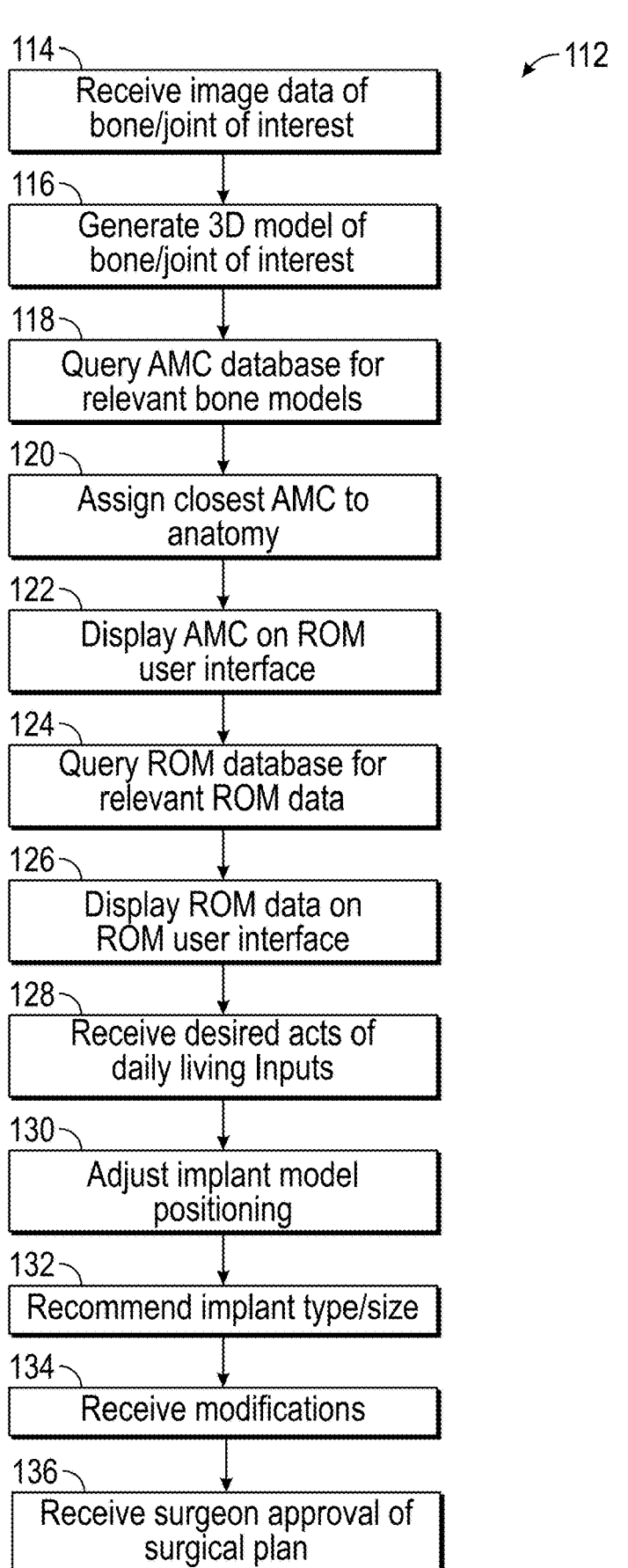
FIG. 9 schematically illustrates a method for planning an orthopedic procedure on a respective patient using a surgical planning system.

FIG. 9 schematically illustrates a method 112 for planning an orthopedic procedure for a respective patient using the system 10. The method 112 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 112. In an exemplary implementation, the computing device 40 of one or more of the client computers 14 may be programmed to execute the method 112. However, other implementations are further contemplated within the scope of this disclosure.

Image data of a bone or joint of interest of the patient may be received at step 114. The image data may be received directly from the imaging device 16 or may be acquired by accessing the record or entry associated with the patient from the patient profile database 64.

A 3D model 30 (FIG. 2) of the bone or joint of interest may be generated at step 116. The planning environment 28 of the computing device 40 may incorporate and/or interface with one or more modeling packages, such as a computer aided design (CAD) package, to render the 3D model of the bone or joint of interest.

Next, at step 118, the computing device 40 may query the anatomical makeup classification database 70 to locate bone models stored therein that have similar anatomical makeup classifications. The anatomical makeup classification 80 (FIG. 4) that is closest to the anatomy encompassed by the 3D model 30 (FIG. 2) may then be assigned to the 3D model 30 at step 120 and displayed on a range of motion user interface of the computing device 40 at step 122. As part of displaying the anatomical makeup classification 80, a confidence level indicator may be displayed within the range of motion user interface for visually indicating the similarity between the assigned anatomical makeup classification 80 and the anatomy being analyzed. The confidence level indicator may be displayed as a percentage or any other visual indicator.

The range of motion database 68 may be queried at step 124 to obtain range of motion data that is relevant to the assigned anatomical makeup classification 80. The range of motion data associated with the assigned anatomical makeup classification 80, including information such as the angular arc and the mode of impingement, may be displayed on the range of motion user interface at step 126.

At step 128, the surgeon or other staff user of the system 10 may be queried to select the desired acts of daily living goals of the patient. The positioning of the implant model 32 may be automatically adjusted relative to the bone model based on the selected acts of daily living at step 130. The system 10 may then output a recommended implant size/type and position and orientation for meeting the selected acts of daily living at step 132.

The surgeon may be prompted to modify the recommended implant type, positioning, and/or orientation per his/her clinical judgement at step 134. The method 112 may end at step 136 in response to receiving the surgeon's approval of the surgical plan. As part of this step, a comparison of the simulated range of motion results stored in the ROM database 68 to the range of motion achieved by the surgeon's planned positions and orientations may be presented to the user within a graphical user interface. This step may further include notifying the surgeon within the graphical user interface of any potential impact the proposed changes may have based on past surgical outcome data associated with prior patients having similar anatomical makeup classifications.

Figure 10:
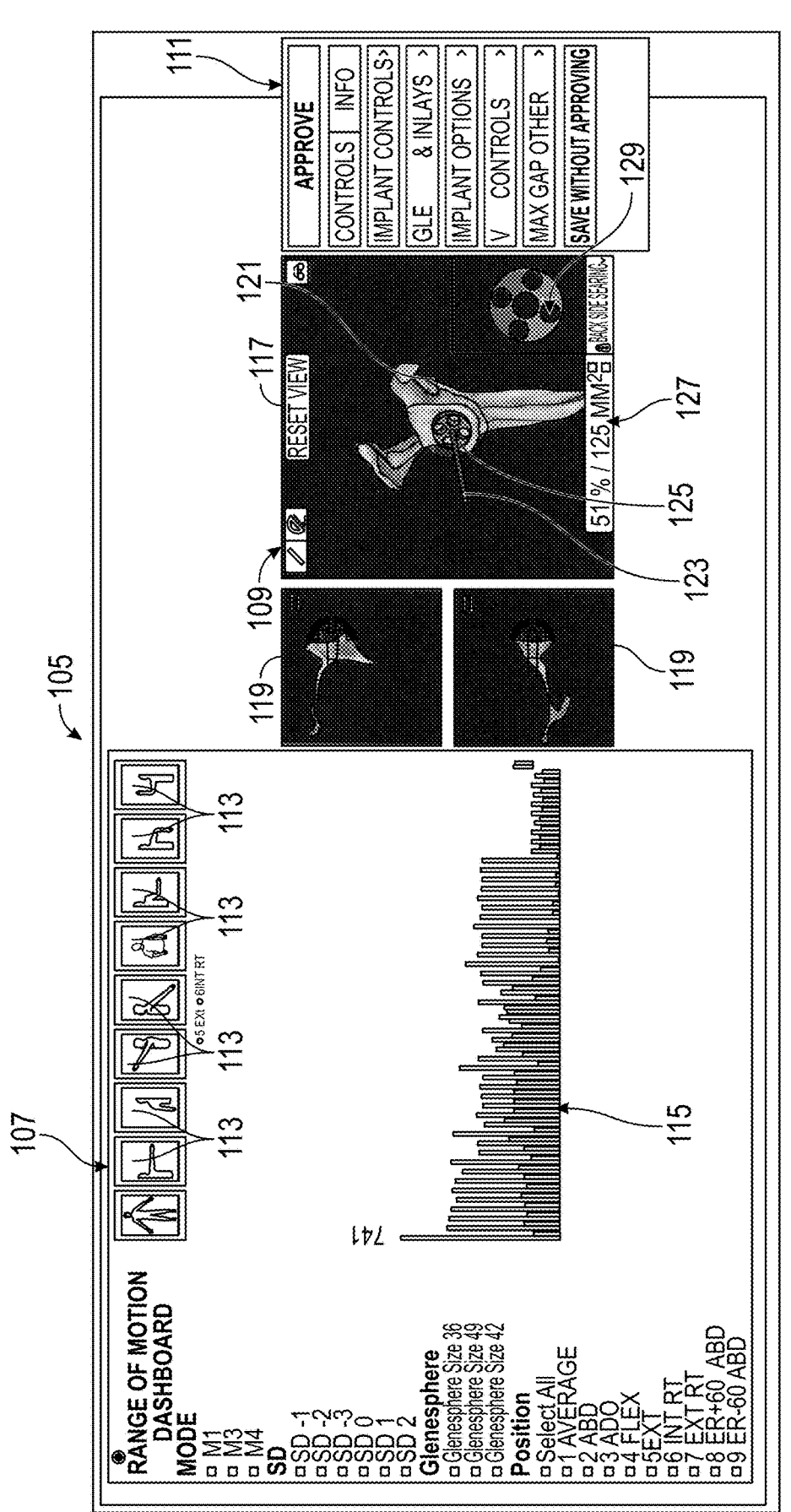
FIG. 10 illustrates an exemplary user interface of a surgical planning system.

FIG. 10 illustrates an exemplary range of motion user interface 105 that may be provided during the method 112 discussed above. The range of motion user interface 105 may be presented within the planning environment 28, for example.

The range of motion user interface 105 may include a range of motion dashboard 107, a display window 109, and a control panel 111. The range of motion dashboard 107 may present various range of motion data to the user. The range of motion dashboard 107 may include a plurality of selectable buttons 113 related to foundational joint motion expectations for the patient. The foundational joint motion expectations that may be represented by the buttons 113 may include but is not limited to desired post-surgery range of motion for abduction, adduction, external rotation, internal rotation, extension, flexion, external rotation combined with 60° abduction, and internal rotation combined with 60° abduction.

The range of motion dashboard 107 may further include a bar graph 115 for illustrating range of motion data for each of the foundational joint motion expectations. For example, the bar graph 115 may provide a visual display of the range of motion achieved for a selected foundational joint motion expectation for one or more AMCs 80 (FIG. 4) that are closest to the anatomy of the patient that the surgical plan is being created for.

The display window 109 may include a 3D window 117 and multiple 2D windows 119. A virtual bone model 121 of the patient's anatomy may be displayed within the 3D window 117 and the 2D windows 119. A positioning of both a virtual guide pin 123 and a virtual implant 125 that is necessary for achieving the desired joint motion expectations may be displayed relative to the virtual bone model 121 to provide the user with information on how to best approach the surgery being planned.

The display window 109 may be manipulated using the control panel 111. For example, the control panel 111 may include a plurality of toggles, buttons, sliders, etc. that allow the user to modify various settings, such as the positioning of the virtual guide pin 123 and/or the virtual implant 125 relative to the virtual bone model 121. In an embodiment, a backside seating amount 127 and a color-coded backside seating map 129 may be provided on the display window 109 and may automatically update as adjustments are made to the virtual positions of the virtual guide pin 123 and the virtual implant 125 relative to the virtual bone model 121. The information presented in the display window 109 may also automatically update as the user pages through each of the buttons 113.

FIG. 11 schematically illustrates another method 138 for planning an orthopedic procedure for a respective patient using the system 10. The method 138 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 138. In an exemplary implementation, the computing device 40 of one or more of the client computers 14 may be programmed to execute the method 138. However, other implementations are further contemplated within the scope of this disclosure.

Image data of a bone or joint of interest of the patient may be received at step 140. The image data may be received directly from the imaging device 16 or may be acquired by accessing the record or entry associated with the patient from the patient profile database 64.

A 3D model of the bone or joint of interest may be generated at step 142. The planning environment 28 of the computing device 40 may incorporate and/or interface with one or more modeling packages, such as a computer aided design (CAD) package, to render the 3D model of the bone or joint of interest.

Next, at step 144, the computing device 40 may query the anatomical makeup classification database 70 to locate bone models stored therein that have anatomical makeup classifications 80 that are similar to the anatomical makeup classification 80 of the bone or joint of the patient. The anatomical makeup classification 80 that is closest to the anatomy encompassed by the 3D model may then be assigned to the 3D model at step 146 and displayed on a surgical outcomes user interface of the computing device 40 at step 148. As part of displaying the anatomical makeup classification 80, a confidence level indicator may be displayed within the graphical user interface for visually indicating the similarity between the assigned anatomical makeup classification and the anatomy being analyzed. The confidence level indicator may be displayed as a percentage or any other visual indicator.

The surgical outcomes database 66 may be queried at step 150 to obtain surgical outcomes data that is most relevant to the assigned anatomical makeup classification. The surgical outcomes data associated with the assigned anatomical makeup classification 80 may be displayed on the surgical outcomes user interface at step 152. The surgical outcomes data that is displayed to the user may be automatically updated in response to a user prompt, such as when the user changes the planned procedure type, for example.

In an embodiment, the surgical outcomes database 66 may be queried to locate prior surgeries that involved patients having an average bone density that is comparable to an estimated average bone density of a bone associated with the anatomy of the patient. This comparison can be used to recommend a particular surgical implant that is not incompatible with the average bone density of the bone under study, for example.

Next, at step 154, data from the surgical outcomes database 66 for the comparable anatomical makeup classifications 80 and a plurality of variables associated with a surgical plan for operating on the patient may be leveraged in order to determine one or more survivorship predictive indexes. The variables may include factors such as surgical implant type, surgical implant size, surgical implant orientation, a surgical procedure type, a surgical implant backside seating configuration, a fastener orientation, or any combinations thereof. The variables are inputs to the system 10 that may be selected by the surgeon or staff user within the surgical outcomes user interface.

The determined survivorship predictive index may be displayed on the surgical outcomes user interface at step 156. Each survivorship predictive index may be a percentile representation of a confidence level that the surgical plan will result in a successful surgical outcome for at least a predefined amount of time. For example, based on the data of the comparable anatomical makeup classifications 80 and the relevant variables selected/set by the surgeon, the system 10 may determine and display a survivorship predictive index of 40% at three years post-surgery for comparable patients who underwent a standard total shoulder arthroplasty procedure and a survivorship predictive index of 85% at three years post-surgery for comparable patients who underwent a reverse shoulder arthroplasty procedure, thus indicating to the surgeon that a more successful outcome for the patient could likely be obtained by performing a reverse shoulder arthroplasty procedure rather than a standard total shoulder arthroplasty procedure.

After displaying the survivorship predictive index displayed at step 156, the system 10 may prompt the surgeon for making any revisions to the variables associated with the current surgical plan at step 158. If revisions are received as inputs into the system 10, an updated survivorship predictive index may be displayed at step 160.

The system 10 may output a recommended procedure type, implant size/type, and implant position/orientation for best matching the comparable anatomical makeup classifications at step 162. The surgeon may be prompted to modify the recommended implant type, positioning, and/or orientation per his/her clinical judgement at step 164. The method 138 may end after receiving, at step 166, the surgeon's approval of the surgical plan.

Figure 12:
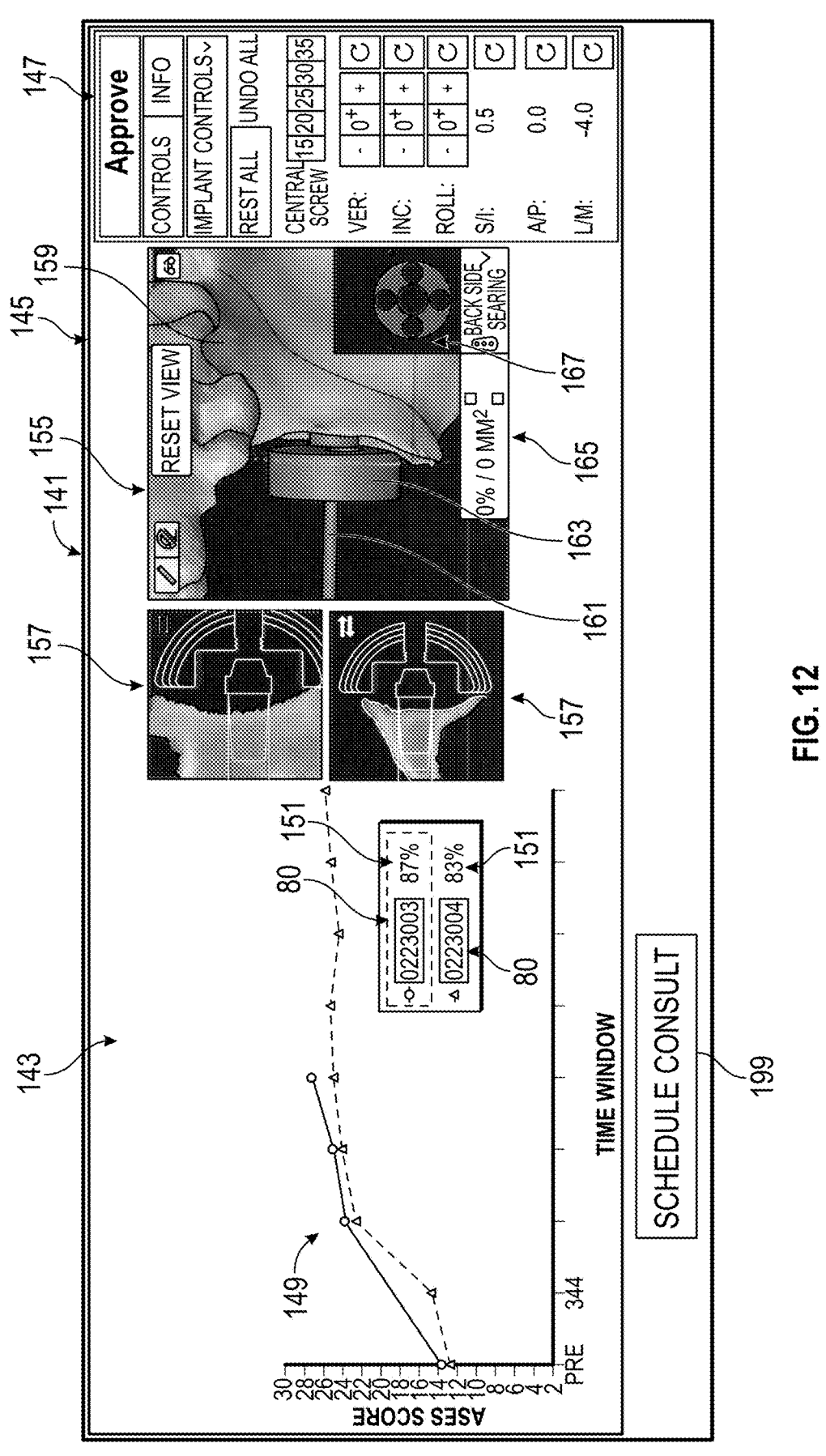
FIG. 12 illustrates another exemplary user interface of a surgical planning system.

FIG. 12 illustrates an exemplary surgical outcomes user interface 141 that may be provided during the method 138 discussed above. The surgical outcomes user interface 141 may be presented within the planning environment 28, for example.

The surgical outcomes user interface 141 may include a graphical listing 143 for displaying the anatomical makeup classifications 80 most similar to the anatomical makeup classification of the bone or joint of the patient, a display window 145, and a control panel 147.

The graphical listing 143 may include a graph 149 of ASES score versus time for each of the comparable anatomical makeup classifications 80 that are listed. Although two anatomical makeup classifications 80 are shown being listed in FIG. 12, the graphical listing 143 could provide a greater or fewer number of anatomical makeup classifications 80 within the scope of this disclosure.

The graphical listing 143 may further include a confidence level indicator 151 that may be displayed adjacent to each comparable anatomical makeup classification 80. The confidence level indicator 151 may be a percentage or any other visual indicator for visually indicating the similarity between the assigned anatomical makeup classification and the anatomy being analyzed. The user may select the desired comparable anatomical makeup classification 80 using an input selector 153, for example.

The display window 145 may include a 3D window 155 and multiple 2D windows 157. A virtual bone model 159 of the patient's anatomy may be displayed within the 3D window 155 and the 2D windows 157. A virtual guide pin 161 and a virtual implant 163 associated with the selected comparable anatomical makeup classification 80 may be displayed relative to the virtual bone model 159 to provide the user with information on how prior surgeries were conducted for patient's having the comparable anatomical makeup classification 80.

The display window 145 may be manipulated using the control panel 147. For example, the control panel 147 may include a plurality of toggles, buttons, sliders, etc. that allow the user to modify various settings, such as the positioning of the virtual guide pin 161 and/or the virtual implant 163 relative to the virtual bone model 159. In an embodiment, a backside seating amount 165 and a color-coded backside seating map 167 may be displayed on the display window 145 and may automatically update as adjustments are made to the virtual positions of the virtual guide pin 161 and the virtual implant 163 relative to the virtual bone model 159.

The surgical outcomes user interface 141 may further include a consult scheduling button 199. The user may press or otherwise actuate the consult scheduling button 199 in order to arrange a consultation with a surgeon who performed the prior surgery for the comparable anatomical makeup classification 80. Once the consult scheduling button 199 has been actuated, the user and the relevant surgeon may be presented with a series of prompts for coordinating and carrying out the consultation. The consultation may be conducted via chat room, telephone, video conference, etc. If desired, the identities of one or both of the requesting surgeon and the consulting surgeon may be kept confidential during the consultation.

Figure 13A:
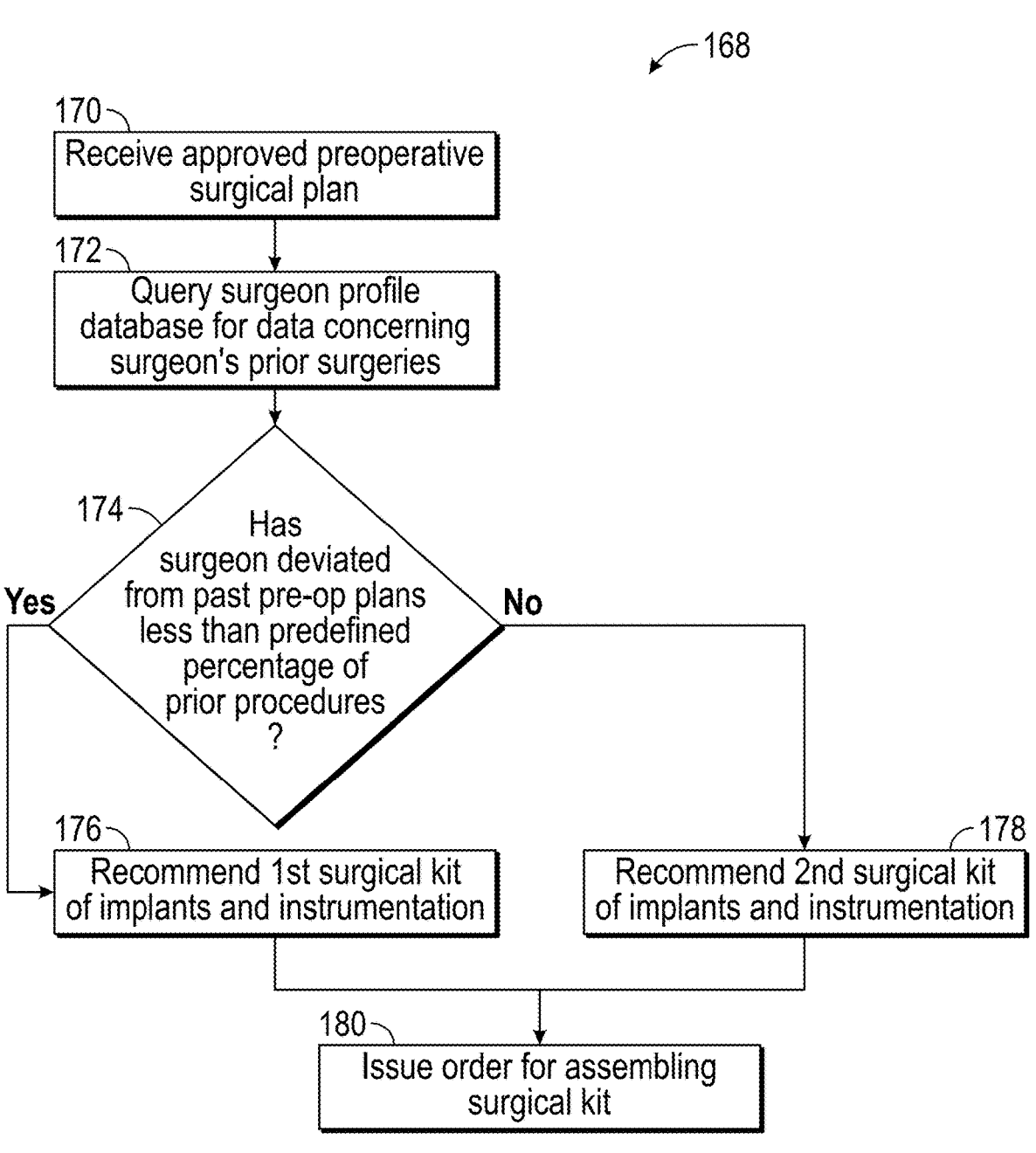
FIG. 13A schematically illustrates yet another exemplary method for planning an orthopedic procedure on a respective patient using a surgical planning system.

FIG. 13A schematically illustrates yet another method 168 for planning an orthopedic procedure for a respective patient using the system 10. The method 168 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 168. In an exemplary implementation, the computing device 40 of the host computer 12 may be programmed to execute the method 168. However, other implementations are further contemplated within the scope of this disclosure.

The method 168 may begin at step 170 in response to receiving a preoperative surgical plan that has been approved by a respective surgeon. The surgeon profile database 65 may then be queried at step 172 for data concerning the surgeon's prior surgeries planned using the system 10 for the procedure indicated by the approved preoperative surgical plan. The data analyzed from the surgeon profile database 65 may include the type and amount of implants actually used in the surgeon's prior surgeries, and the type and amount of implants included as part of the preoperative surgical plan for each of the surgeon's relevant prior surgeries.

At step 174, the system 10 may determine, based on a comparison of the pre-operative and post-operative data analyzed at step 172, for example, whether the surgeon has deviated from his/her past preoperative surgical plans in less than a predefined percent of his/her prior surgical procedures. In some implementations, the predefined percent may be defined as 5% of the prior surgical procedures. However, other thresholds may be established within the scope of this disclosure. In an embodiment, a "deviation" is assumed to have taken place when the surgeon changed the pre-planned procedure type, changed the pre-planned implant type, or employed a size deviation of more than one size during the prior surgical procedures.

If a YES flag is returned at step 174, a first surgical kit that includes only those implants and instrumentation necessary for executing the approved preoperative surgical may be recommended at step 176. Alternatively, if a NO flag is returned at step 174, a second surgical kit that includes a greater number of implants and instrumentation than the first surgical kit may be recommended at step 178. An order for assembling the relevant surgical kit may then be issued at step 180.

Figure 13B:
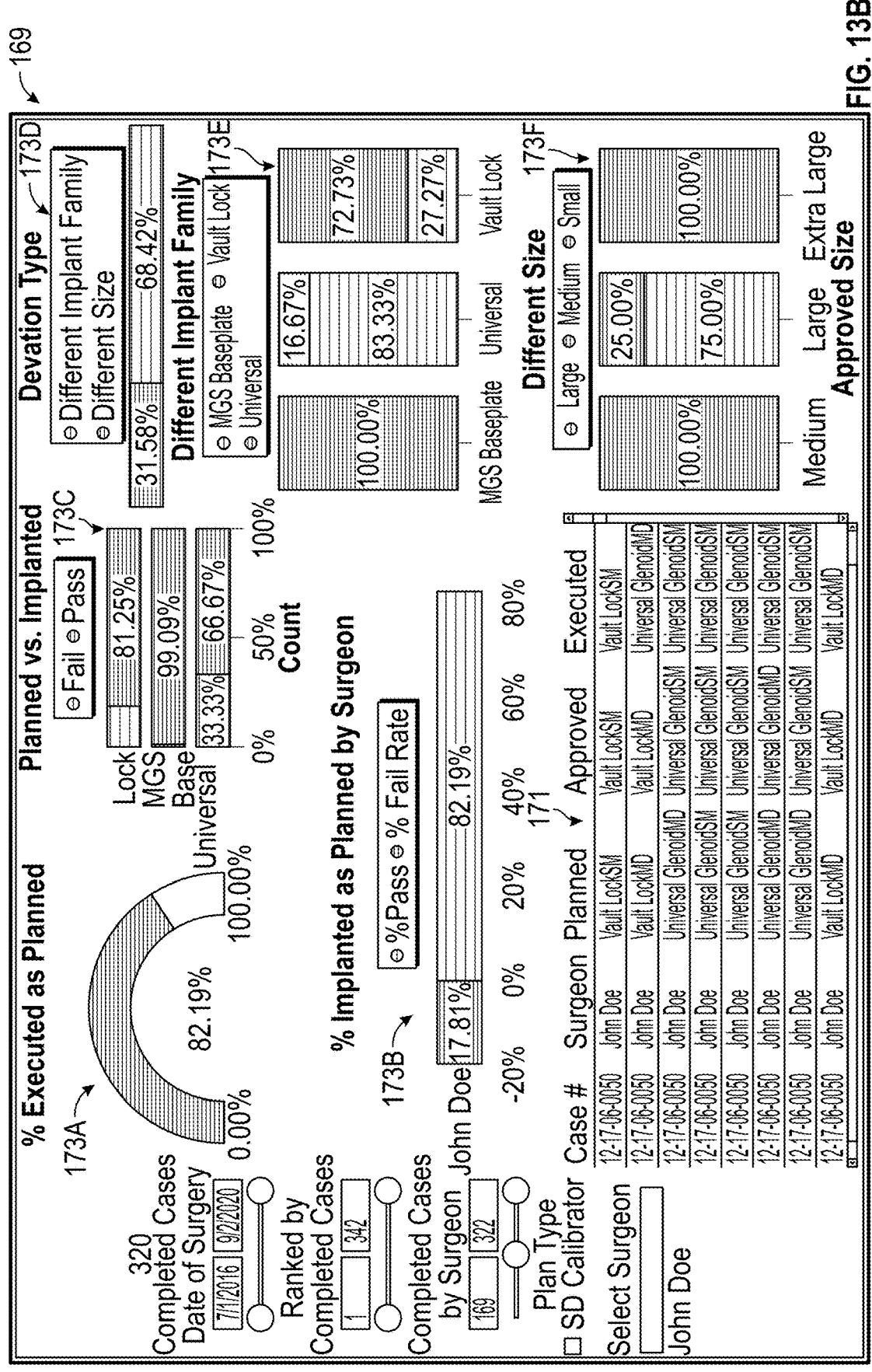
FIG. 13B illustrates yet another exemplary user interface of a surgical planning system.

FIG. 13B illustrates an exemplary deviation user interface 169 that may be provided during the method 168 discussed above. The deviation user interface 169 may be presented within the planning environment 28, for example.

The deviation user interface 169 may be configured to present various surgery-related information pertaining to a selected surgeon related to how often the surgeon has deviated from his/her past preoperative surgical plans. The deviation user interface 169 may provide a case listing 171 of the surgeon's prior surgeries and various bar graphs 173A-173F designed for conveying deviation related information to the user. For example, the bar graph 173A may illustrate the percent of prior surgeries executed as planned, the bar graph 173B may illustrate the percent of implants implanted as planned during prior surgeries, the bar graph 173C may illustrate planned versus implanted implants, the bar graph 173D may illustrate deviation type, the bar graph 173E may illustrate different implant families used in the prior surgeries, and the bar graph 173F may illustrate different sizes of implants used during prior surgeries. Other deviation related information could alternatively or additionally be conveyed to the user via the deviation user interface 169.

FIG. 14 schematically illustrates a method 182 for post-operatively updating one or more databases 38 associated with the system 10. The method 182 may be performed subsequent to using the system 10 to prepare a surgical plan for a patient and subsequent to implementing the surgical plan during an actual surgery. Fewer or additional steps than are recited below could be performed within the scope of this disclosure, and the recited order of steps is not intended to limit this disclosure. The system 10, via any of its associated computing devices and modules, may be configured to execute each of the steps of the method 182. In an exemplary implementation, the computing device 40 of the host computer 12 may be programmed to execute the method 182. However, other implementations are further contemplated within the scope of this disclosure.

The system 10 may receive postoperative patient outcome data from a user at step 184. In some implementations, the postoperative patient outcome data may be manually entered by a surgeon or other staff after intraoperatively performing a surgical procedure on the patient according to a preoperative surgical plan previously created within the system 10. In other implementations, the postoperative patient outcome data may be automatically communicated to the system 10 after performing the surgical procedure as part of a closed feedback loop that can be implemented via a neural network, for example. The postoperative outcome data may include information such as the size and types of implants used during the now completed surgical procedure, the positions and orientations of the used implants, implant failure data, data related to the achievement or non-achievement of pre-operative acts of daily living goals, etc.

An anatomic makeup classification 80 may be assigned to each anatomy associated with the postoperative patient outcome data at step 186. This may be achieved, for example, by querying the anatomical makeup classification database 70 to locate bone models stored therein that have anatomical makeup classifications that are similar to the anatomical makeup classification of the anatomy indicated within the postoperative patient outcome data.

At step 188, the surgical outcomes database 66 may be updated with the information contained within the postoperative patient outcome data. For example, the surgical outcomes database 66 may be updated with the size and types of implants used during the now completed surgical procedure, the positions and orientations of the used implants, etc.

The size, type, position, and orientation of the implants indicated within the postoperative patient outcome data may be input into the range of motion database 68 at step 190. Next, at step 192, one or more motion simulations may be performed on the anatomy and implants associated with the postoperative patient outcome data. Contact or collision points may be identified at step 194 for identifying the range of motion end points for each range of motion simulation performed. The angular arc and mode of collision (e.g., implant-to-implant, implant-to-bone, bone-to-bone, etc.) for each contact point may be recorded at step 196.

The center of rotation of the implants associated with the postoperative patient outcome data may be adjusted at step 198. At step 200, the center of rotation of the implants may be adjusted relative to the respective bone model in multiple increments for recording the angular arcs and collision modes associated with the adjusted positions. All range of motion data derived from the simulations performed at steps 190-200 may then be saved within the range of motion database 68 at step 202.

Figure 15:
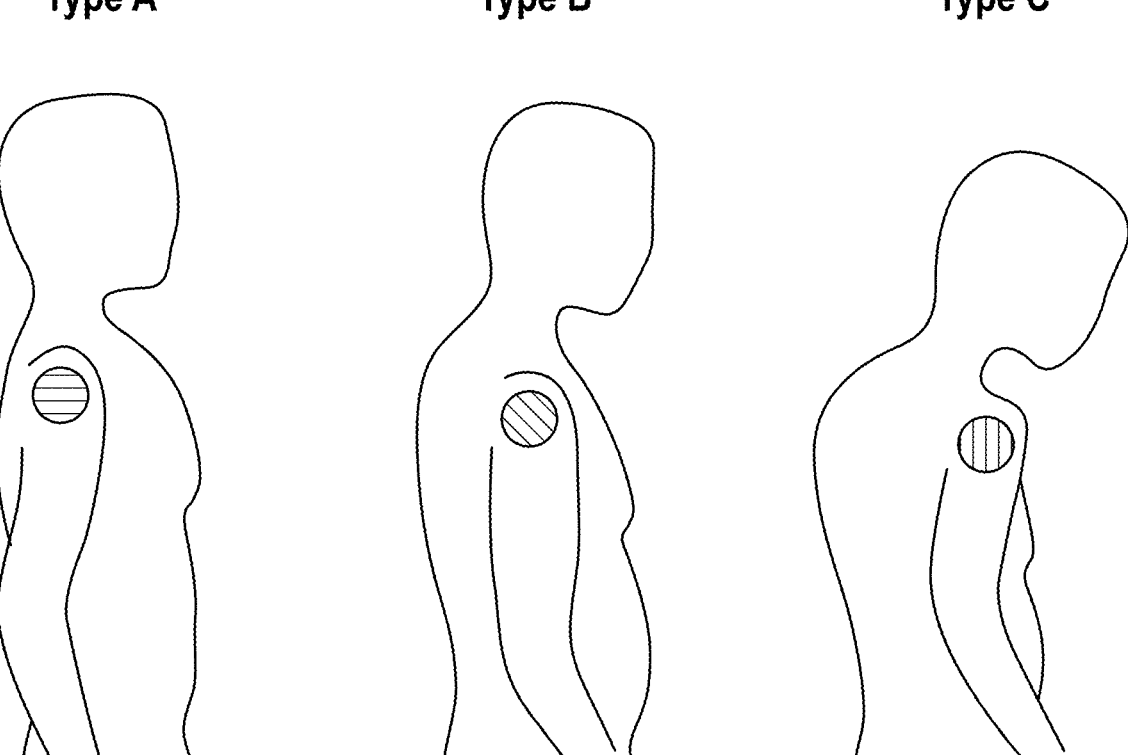
FIG. 15 illustrates a set of posture types associated with an anatomy.

Referring to FIG. 15, the anatomy of a patient may be associated with a respective posture as disclosed in Moroder, P., et al. (2020). The influence of posture and scapulothoracic orientation on the choice of humeral component retrotorsion in reverse total shoulder arthroplasty. J Shoulder Elbow Surg (2020) 29, 1992-2001. A range of postures may be assigned to a set of posture types of an anatomy (e.g., A, B, C). FIG. 15 discloses a set of posture types (e.g., A, B, C). Posture type A may be representative of a perfect posture. Posture types B and C may deviate from posture type A.

Utilizing the techniques disclosed herein, one or more characteristics associated with a posture of the patient may be determined. Although three posture types are disclosed, it should be understood that fewer or more than three posture types may be utilized according to the teachings disclosed herein. The posture of a patient may affect a relative position between two or more bones and/or joints, including non-adjoining and/or adjoining bones. The posture of a patient may affect a relative position between opposed articular surfaces of adjoining bones. Utilizing the techniques disclosed herein, the position and orientation of one or more implants for treating the patient may be established based on the determined posture characteristics.

Figures 16A, 16B, 16C:
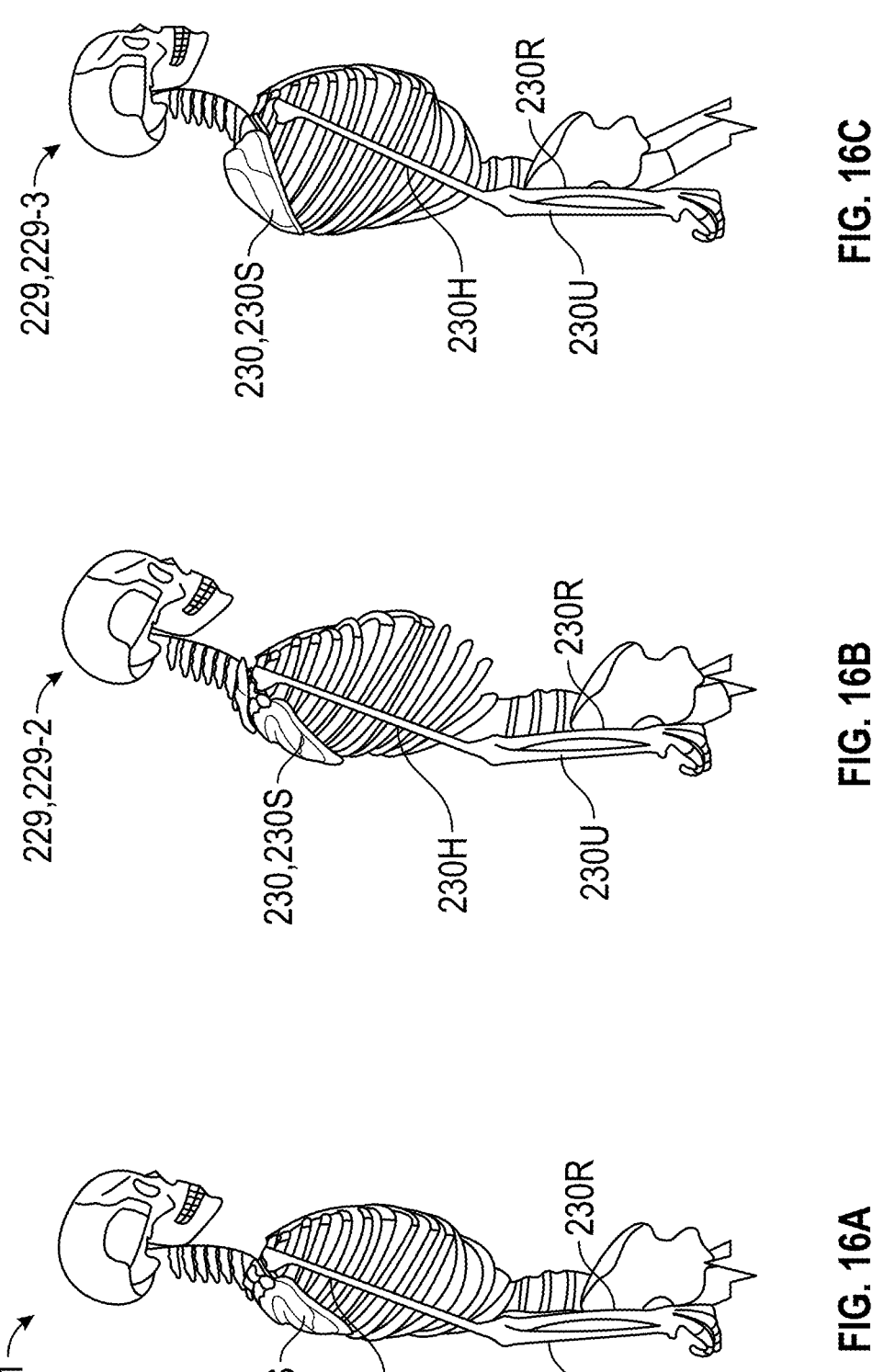
FIGS. 16A-16C illustrate anatomical models associated with a set of posture types of an anatomy.

FIGS. 16A-16C disclose anatomical models 229 (indicated as models 229-1, 229-2, 229-3). The anatomical models 229-1 to 229-3 may be associated with respective patients. The anatomical models 229 may include one or more bone models 230, which may be associated with any of the bones of the anatomy. The bone models 230 may be representative of bones associated with a shoulder joint, such as a scapula and/or humerus, and one or more bones of an associated limb, such as an ulna and/or radius of a forearm. The scapula may be associated with a scapula bone model 230S. The humerus may be associated with a humerus bone model 230H. The ulna and radius may be associated with an ulna bone model 230U and radius bone model 230R. The anatomical models 229 and/or associated bone models 230 may be established and arranged utilizing any of the techniques disclosed herein.

Figures 17A, 17B, 17C:
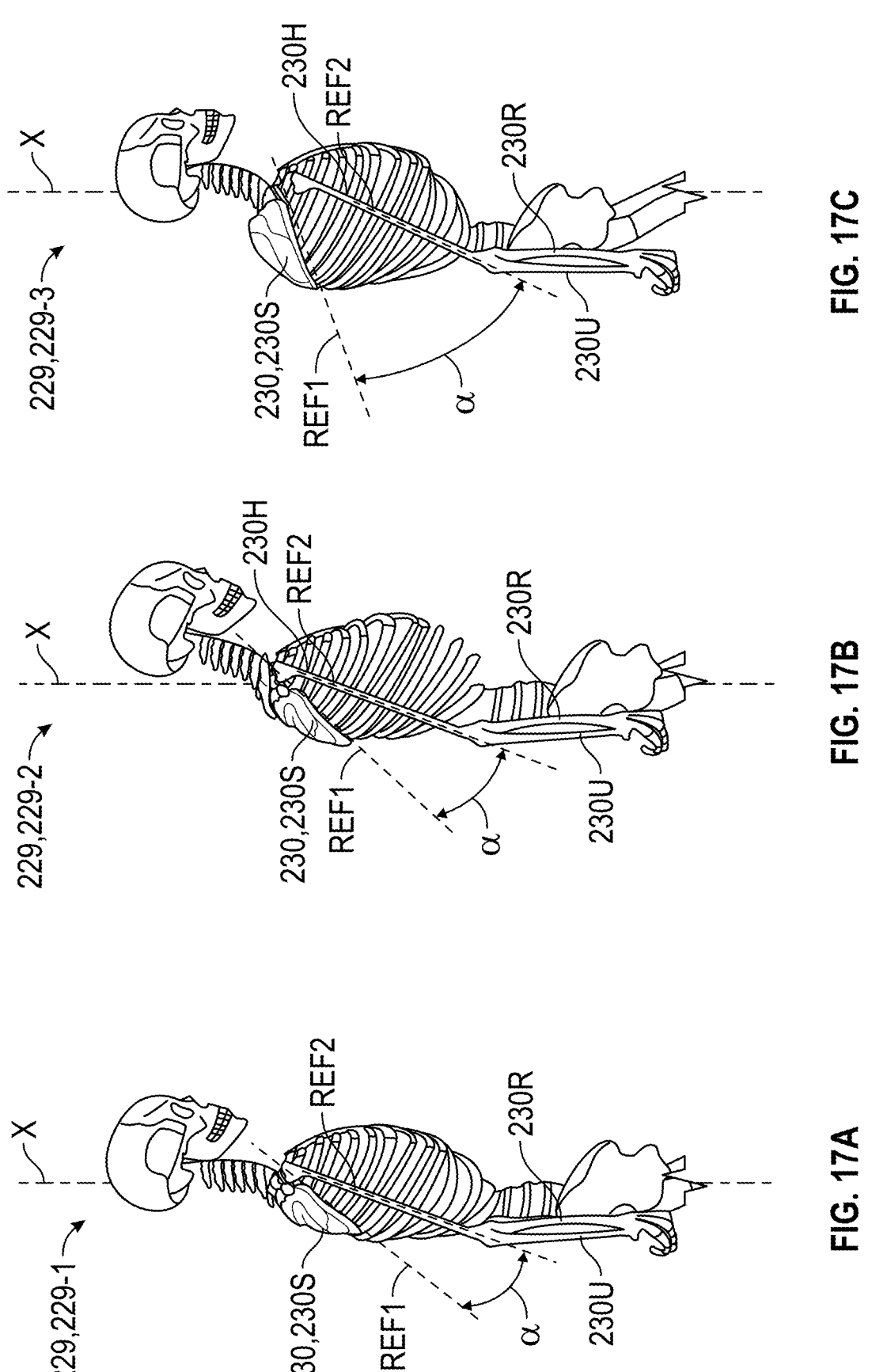
FIGS. 17A-17C illustrate scapular angles associated with the respective posture types of FIGS. 16A-16C.

Referring to FIGS. 17A-17C, with continuing reference to FIGS. 15 and 16A-16C, anatomical models 229-1 to 229-3 may be associated with postures of respective patients. Various techniques may be utilized to characterize a posture of the patient. The planning system 10 (FIGS. 1-2) may be configured to determine one or more characteristics associated with a posture of the patient based on an orientation of one or more of the bone models 230 of the anatomical model 229. Bone models 230 of the humerus 230H, ulna 230U and/or radius 230R may be situated at a resting (e.g., starting) angle relative to the scapula model 230S, including during image acquisition.

The anatomical models 229-1 to 229-3 may establish one or more angles α that may be associated with a posture of the patient anatomy. Various techniques may be utilized to define the angle α. A first bone model 230 associated with a first bone of the patient may extend along a first reference plane REF1. A second bone model 230 associated with a second bone of the patient may extend along a second reference plane REF2. The first and second reference planes REF1, REF2 may intersect to establish the angle α. In implementations, the angle α may be established relative to the first reference plane REF1 and axis X of the patient. The angle α may be associated with a posture of the patient.

A scapular angle associated with the scapula of the patient may be established. The scapular angle can include one or more components relative to an anatomy of the patient (e.g., a set of angles). In implementations, the scapular angle may be defined based on scapular internal rotation, scapular upward rotation and/or scapular interior tilt. The scapular angle may be determined when the patient is standing or situated in a resting (e.g., horizontal) position. In implementations, the first bone model 230 may be a scapula bone model 230S associated with the scapula of the patient. The second bone model 230 may be a humerus bone model 230H associated with the humerus of the patient. The angle α may be defined as an angle between a spine of the scapula and an axis of the humeral diaphysis with respect to a medial plane of the patient. A spine of the scapula model 230S may extend along the first reference plane REF1. A diaphysis of the humeral model 230H may extend along the second reference plane REF2. The spatial module 50 and/or another portion of the planning system 10 may be configured to determine the first and/or second reference planes REF1, REF2 and associated angle α. In implementations, the surgeon or clinical user may interact with the user interface 56 to specify the first and/or second reference planes REF1, REF2.

The anatomical models 229 may include one or more bone models 230 arranged relative to the axis X. The axis X may be a vertical axis associated with a patient in an upright (e.g., standing) position and may be normalized relative to a coordinate system. The anatomical model 229 may include two or more bone models 230 arranged relative to each other to establish the scapular angle. The axis X may extend along one or more of the bone models 230. The axis X may be established along an intersection between the (e.g., sagittal and coronal) kinematic planes of the patient. The first reference plane REF1 may extend along another one of the bone models 230, such as along the spine of the scapula bone model 230S. The first reference plane REF1 may intersect the axis X of the patient to establish the scapular angle. An orientation of the first reference plane REF1 may be established based on an internal rotation, an upward rotation and/or an anterior tilt of the scapula. In implementations, the scapular angle may be a set of values defined relative to the scapula internal rotation, scapula upward rotation and/or scapula anterior tilt. For the purposes of this disclosure, the terms "about," "substantially" and "approximately" mean±10 percent of the stated value or relationship unless otherwise indicated. The humerus bone model 230H, ulna bone model 230U and/or radius bone model 230R may be substantially vertical or may be transverse to the axis X of the patient. In the implementation of FIGS. 17A-17C, the ulna bone model 230U and radius bone model 230R may be substantially parallel to the axis X.

The scapular angles of the anatomical models 229-1 to 229-3 may be the same or may differ from each other. The postures of the respective anatomical models 229-1 to 229-3 may be characterized by a set of posture types (e.g., A, B, C). Each posture type may be assigned a range of values for one or more posture parameters (e.g., characteristics), such as the scapular angle. In implementations, posture type A may be associated with a scapular internal rotation of approximately 32±6 degrees, a scapular upward rotation of approximately −3±6 degrees, and a scapular interior (e.g., anterior) tilt of approximately 23±11 degrees. Posture type B may be associated with a scapular internal rotation of approximately 42±3 degrees, a scapular upward rotation of approximately −12±7 degrees, and a scapular interior tilt of approximately 24±8 degrees. Posture type C may be associated with a scapular internal rotation of approximately 53±5 degrees, a scapular upward rotation of approximately −15±13 degrees, and a scapular interior tilt of approximately 33±7 degrees.

The scapular angles of FIGS. 17A-17C may be associated with the posture types of FIGS. 15 and/or 16A-16C. The anatomical model 229-1 of FIG. 17A may be associated with posture type A of FIGS. 15 and 16A. The anatomical model 229-2 of FIG. 17B may be associated with posture type B of FIGS. 15 and 16B. The anatomical model 229-3 of FIG. 17C may be associated with posture type C of FIGS. 15 and 16C. In implementations, the anatomical model 229-1 may be associated with posture type A and/or a scapular angle having any of the value(s) within the disclosed range(s) associated with posture type A. The anatomical model 229-2 may be associated with posture type B and/or a scapular angle having any of the value(s) within the disclosed range(s) associated with posture type B. The anatomical model 229-3 may be associated with posture type C and/or a scapular angle having any of the value(s) within the disclosed range(s) associated with posture type C.

Figures 18A, 18B, 18C:
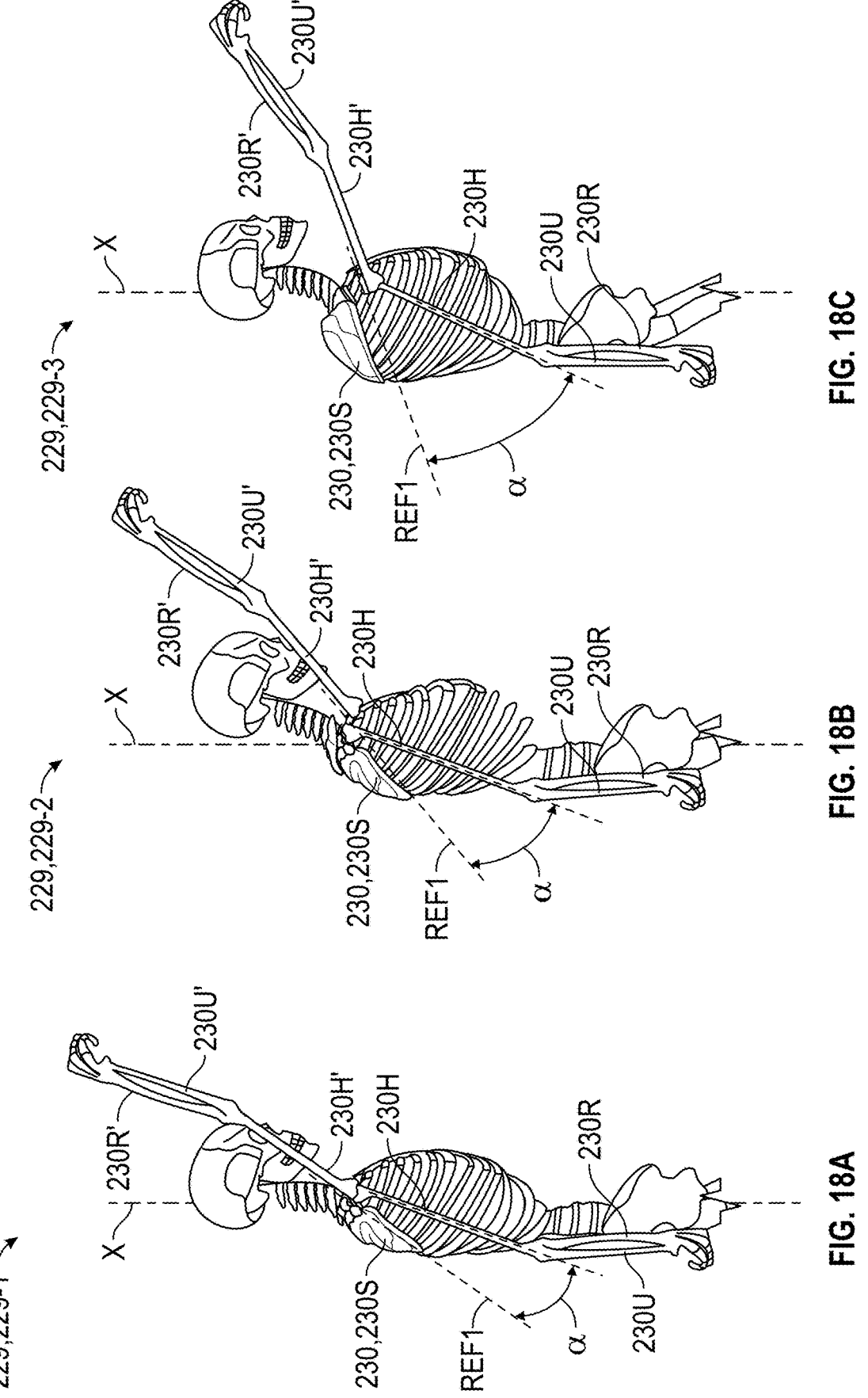
FIGS. 18A-18C illustrates the scapular angles associated with the respective posture types of FIGS. 17A-17C with respective models of a humerus and forearm in an elevated position.

Referring to FIGS. 18A-18C, with continuing reference to FIGS. 17A-17C, the posture of a patient may limit a range of motion of the limb such as the humerus and associated forearm. The anatomical models 229-1 to 229-3 may be associated with instances of the humerus bone model 230H', ulna bone model 230U' and radius bone model 230R' in an elevated position. Range of motion may be characterized by a reference (e.g., scapular) plane REF1 and/or associated scapular angle. Movement of the humerus in an upward direction may generally be limited at approximately the reference plane REF1.

Figure 16D:
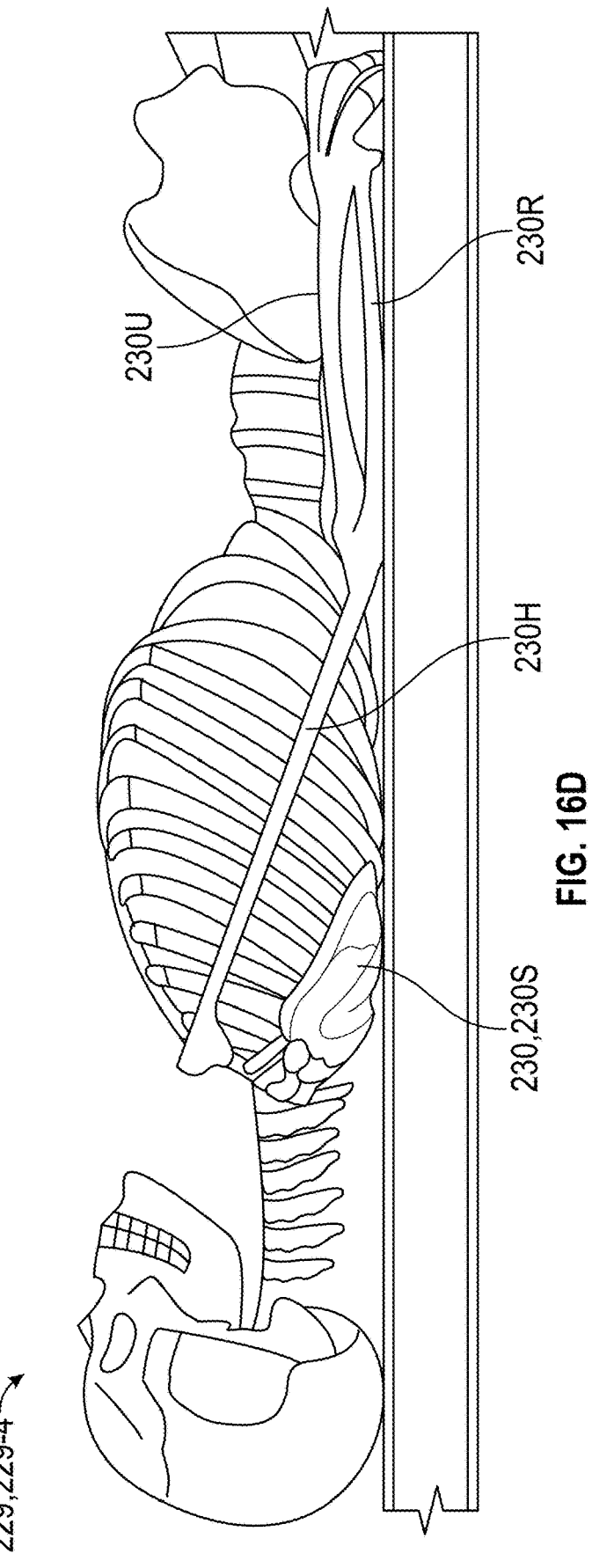
FIG. 16D discloses an anatomical model in a laying position.

Image data associated with the anatomical and bone models 229, 230 may be captured in an acquisition orientation associated with one or more imaging devices 16 (FIGS. 1-2). Each imaging device 16 may be associated with an acquisition reference system. The acquisition reference systems of two or more imaging devices 16 may be the same or may differ from each other. The patient may be positioned relative to a reference point of the acquisition reference system, which may differ between patients based on anatomical makeup, posture, morbidity, etc. The bone models 230 may be in a resting (e.g., starting) position of the patient during acquisition. The resting position may be associated with an upright (e.g., vertical) position or a laying (e.g., horizontal or supine) position of the patient during acquisition of the associated image data. FIG. 16D discloses an anatomical model 229-4. The anatomical models 229-4 may include one or more bone models 230, which may be associated with any of the bones of the anatomy. The anatomical model 229-4 may be associated with a laying (e.g., horizontal) position of the patient (e.g., on a bed of the imaging device) during acquisition of the associated image data. The anatomical model 229-4 may be associated with the same patient as one of the anatomical models 229-1 to 229-3, such as the anatomical model 229-2. An orientation of one or more bones of the patient in an upright position, such as the scapula and humerus, may be determined based on a transformation associated with a laying position of the patient. In implementations, the orientation of the scapula 230S and/or humerus 230H of the anatomical model 229-2 (FIG. 16B) may be established based on a transformation applied to the orientation of the scapula 230S and/or humerus 230H of the anatomical model 229-4 (FIG. 16D). An orientation of the scapula may be non-perpendicular to the axes of the acquisition reference system. The scapula orientation in the acquisition reference system may be characterized by a posture of the patient. A transformation may account for effects on the patient anatomy in the laying position, such as relaxation of the musculature, etc. In implementations, the transformation may include one or more predefined transformation angles. The predefined transformation angles may include three angles of rotation relative to the axes of the reference system. Predefined transformation angles may be established for one or more acquisition positions, such as the laying position and/or upright position. A set of predefined transformation angles may be established for each respective bone of the anatomy. The spatial module 50 may be configured to apply the transformation to the respective bone model(s) 330 to transform the bone model(s) 330 from the laying position to the upright position, or vice versa.

Information relating to the posture of a patient may be incorporated into the systems and methods disclosed herein, such as the system 10 (FIGS. 1-2), to establish a surgical (e.g., preoperative) plan and/or determine and/or validate aspects of range of motion (ROM) associated with the patient utilizing any of the techniques disclosed herein. The system 10 may establish a preoperative plan 36 based on one or more determined posture characteristics (e.g., parameters) associated with the posture of a patient. A position and/or orientation of one or more implants specified in the preoperative plan 36 may be determined based on the determined posture characteristic(s). By incorporating posture information into the systems and methods disclosed herein, the surgeon or clinical user may plan the placement of one or more implants with consideration to the resting (e.g., starting) angle of the shoulder blade ("scapular"). The implant may be assigned a default starting position and/or orientation relative to an adjacent bone. The system 10 may determine a correction value to adjust the default starting position and/or orientation of the implant based on the determined posture characteristic(s). The posture information may be utilized for determining range of motion, including with respect to acts of daily living.

The system 10 may be configured to determine one or more posture parameters associated with a posture of a patient. The system 10 may be configured to adjust an implant plan based on the one or more posture parameters. The implant plan may include any of the parameters disclosed herein, such as implant type, implant dimension and implant position.

Figure 19:
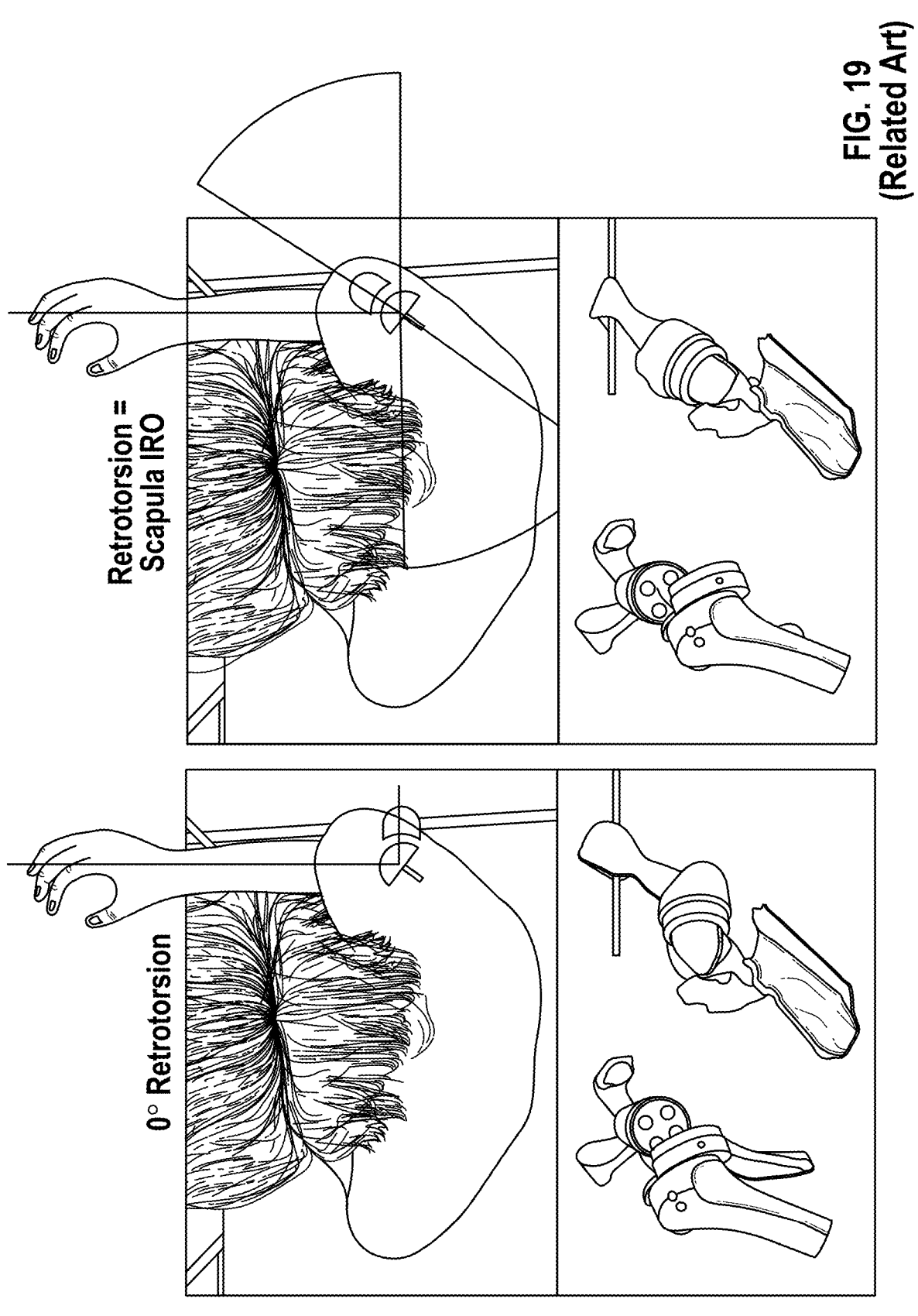
FIGS. 19-20 disclose a clinical example utilizing the techniques disclosed herein.
Figure 20:
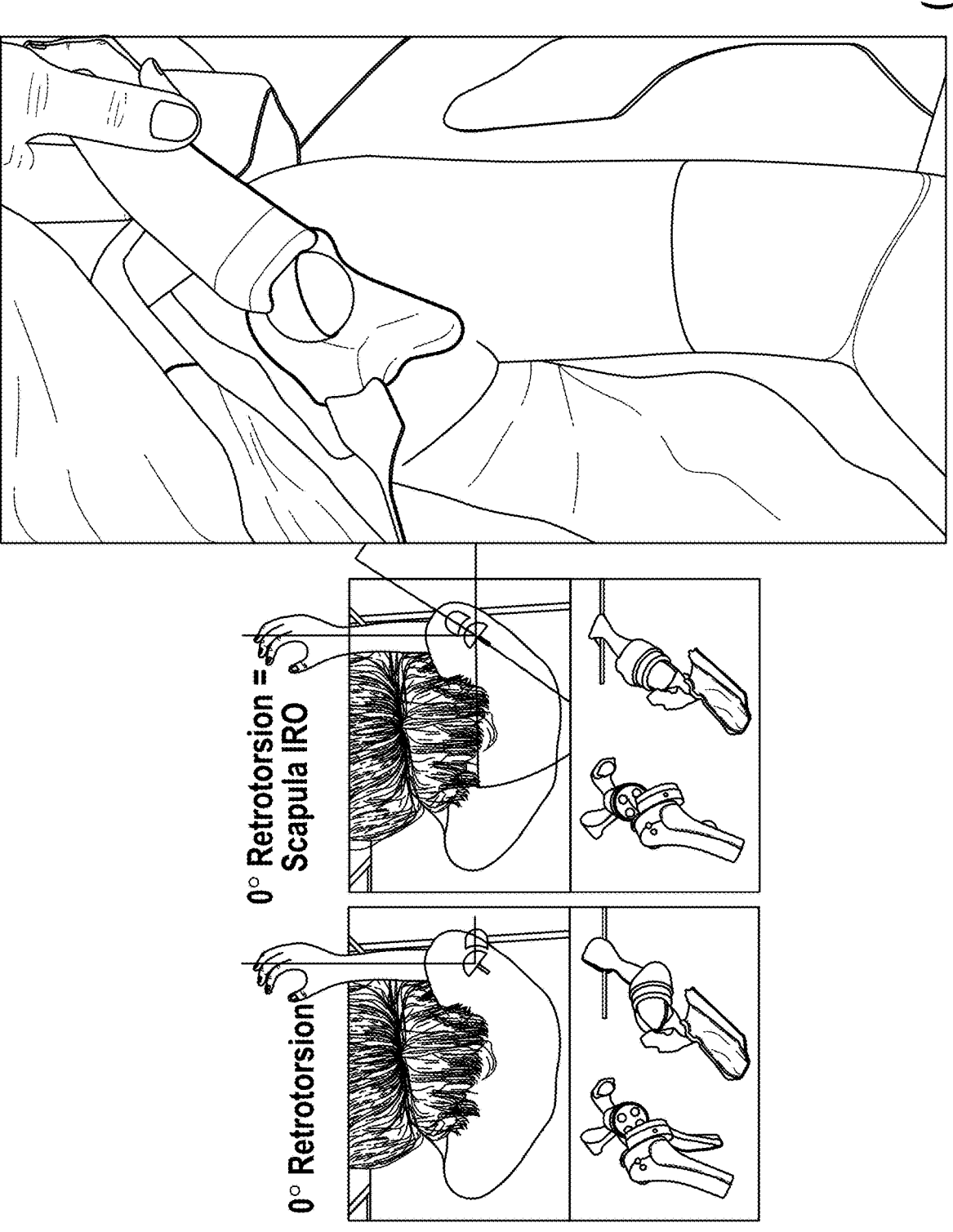

Referring to FIGS. 19-20, the posture of a patient may affect retrotorsion as disclosed in Moroder, P., et al. (2022). Patient Posture Affects Simulated ROM in Reverse Total Shoulder Arthroplasty: A Modeling Study Using Preoperative Planning Software. Clin Ortop Relat Res (2022) 480: 619-631. FIGS. 19-20 disclose a clinical example of a shoulder arthroplasty for a patient. An orientation of an implant associated with a humerus may be adjusted to vary retrotorsion from 0 degrees to a value equal to an internal rotation of the scapula (IRO). Setting the orientation of the implant to the internal rotation of the scapula (IRO) may achieve a relatively greater range of motion and/or reduce a likelihood of impingement of the implant.

In implementations, a posture transformation may be established. The posture transformation may be based on a posture classification and/or one or more measured posture parameters, including any of the posture parameters disclosed herein. Posture parameters may include one or more landmarks of the scapula, a distance or relative position between two or more landmarks, a scapular angle, and/or a dimension of one or more bones of the anatomy (e.g., length of humerus). In implementations, the posture transformation may be utilized to adjust or otherwise set a planned implant position and/or orientation to treat the patient, which may improve range of motion and acts of daily living.

One or more range of motion parameters may be utilized to establish the posture transformation. In implementations, the parameters may be associated with one or more acts of daily living and/or lifestyle goals (e.g., desired post-surgery range of motion for abduction, adduction, external rotation, internal rotation, upward rotation, extension, flexion, external rotation combined with 60° abduction, internal rotation with 60° abduction, etc.). Defined values of the one or more acts of daily living and/or lifestyle goals may be utilized as criteria for establishing the posture transformation.

The system 10 may be configured to perform a range of motion simulation based on one or more parameters associated with a posture of a patient. A storage system 18 may be configured to store range of motion data derived from the range of motion simulation. The parameters may include a scapular angle associated with a scapula of the patient.

Methods may include performing a range of motion simulation based on one or more parameters associated with a posture of a patient. A method may include storing range of motion data derived from the range of motion simulation within a storage system 18 of the surgical planning system 10. The parameters may include a scapular angle associated with a scapula of the patient.

Referring to FIGS. 21-25, with continuing reference to FIG. 2, the planning system 10 may be configured to display a selected anatomical model 329 in one or more display windows 360 of a graphical user interface 356. The anatomical model 329 may include one or bone models 330, which may be associated with respective joint(s). The display module 48 may be configured to display the anatomical model 329 in the display window(s) 360. The spatial module 50 may be configured to adjust a position of one or more bone models 330 relative to each other, another portion of the anatomical model 329, and/or a reference system.

FIGS. 21-26 disclose anatomical models 329 associated with one or more patients. The anatomical models 329 may include a first anatomical model 329-1 (FIGS. 21-23) and/or a second anatomical model 329-2. The anatomical model 329 may include a shoulder model 329SM and one or more implant models 332 associated with various postures and scapular angles of the anatomy. The shoulder model 329SM may include a scapula bone model 330S and a humeral bone model 330H.

The spatial module 50 may be configured to arrange one or more implant models 332 relative to each other and/or the anatomical model 329. The implant models 332 may include a first (e.g., glenoid) implant model 332G and a second (e.g., humeral) implant model 332H. The implant models 332G, 332H may mate with each other. The scapula model 330S, anatomical model 329, glenoid implant model 332G and/or humeral implant model 332H may be associated with various postures and scapular angles. Various parameters may be associated with the scapular angle, such as abduction, adduction, flexion, extension, external rotation, internal rotation, upward rotation, abduction and internal rotation and abduction and external rotation. Values may be assigned to each of the parameters and may be displayed to the user. A summation of the values may be displayed to the surgeon or clinical user in the user interface 356 (see, e.g., FIGS. 22 and 25). A posture transformation may be applied to adjust a default starting position and/or orientation of the implant(s) 332 based on the determined parameters.

The user interface 356 may include a first display window 360-1 and a second display window 360-2. The display module 48 may be configured to cause the user interface 356 to display different anatomical views in the display windows 360-1, 360-2. In implementations, the display module 48 may be configured to cause the first display window 360-1 to display an anterior (or posterior) view of the anatomical model 329-1. The display module 48 may be configured to cause the second display window 360-2 to display a lateral view of the anatomical model 329-1. The spatial module 50 may be configured to set a position of the bone models 330 relative to each other and/or a reference system based on a determined posture of the patient. The surgeon or clinical user may interact with the display windows 360 and/or another portion of the user interface 356 to select one or more of the bone models 330. The display module 48 may be configured to establish a visual contrast between the selected bone model(s) 330 and any remaining bone models 330 and/or other portions of the anatomical model 329.

Figure 21:
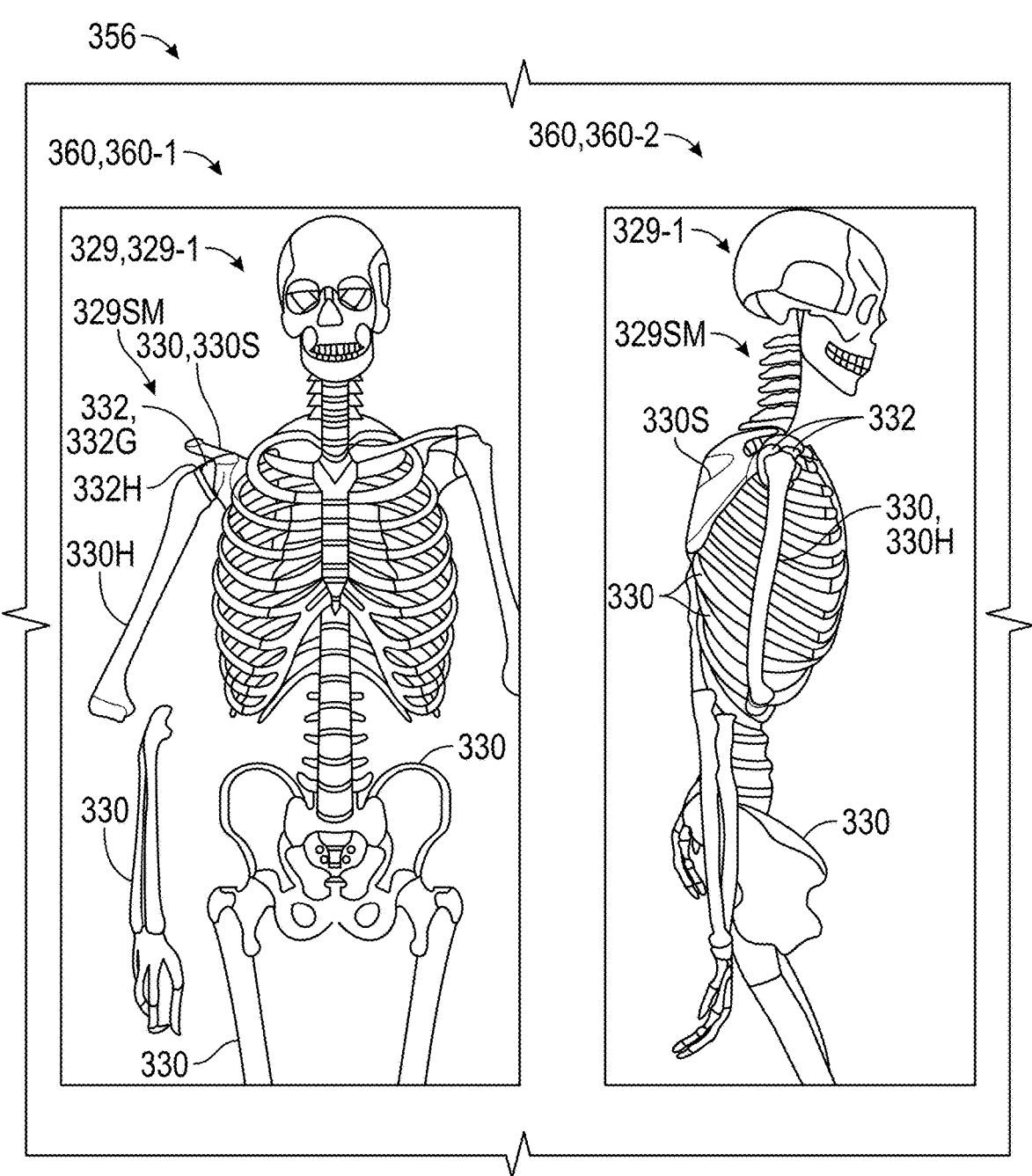
FIGS. 21-23 discloses a shoulder model including a humeral implant mating with a glenoid implant associated with various postures and scapular angles.
Figure 22:
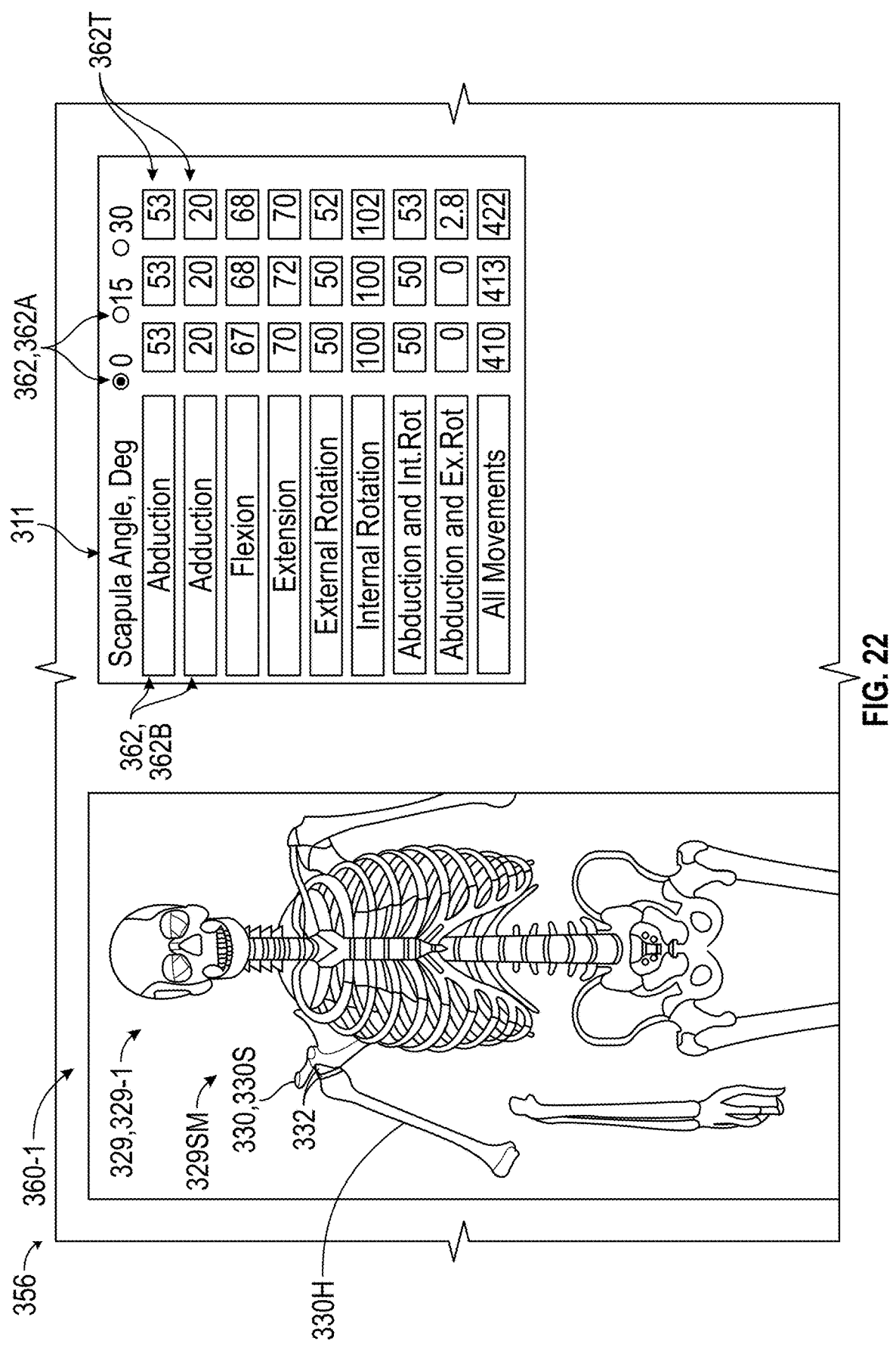

Referring to FIG. 22, with continuing reference to FIGS. 2 and 21, the spatial module 50 may be configured to adjust a position of the selected bone model(s) 330 relative to each other and/or another portion of the anatomical model 329-1. The user interface 356 may include one or more (e.g., interactive) objects 362. The objects 362 may be arranged in a control panel 311. The objects 362 may include buttons 362B, radial buttons 362R and/or text boxes 362T. The text boxes 362T may be configured to display one or more values associated with the anatomical model 329-1. The surgeon or clinical user may adjust one or more of the values displayed in the text boxes 362T in response to selecting the respective text box 362T, button 362B and/or radial button 362R. The buttons 362B, 362R may be associated with various characteristics (e.g., angular relationships) of the selected bone model 330, including any of the characteristics disclosed herein. In implementations, the characteristics may include abduction, adduction, flexion, extension, external rotation, internal rotation, upward rotation, abduction and internal rotation, abduction and external rotation, and/or all movements. The text boxes 362T associated with all movements may be configured to display summations of values for text boxes 362T in the respective columns. The surgeon or clinical user may specify values in one or more of the text boxes 362T to adjust a position and/or orientation of one or more of the selected bone models 330. The surgeon or clinical user may interact with the display window 360 to adjust a position and/or orientation of one or more selected bone models 330 and any associated values in the control panel 311. The display windows 360 and control panel 311 may be dynamically linked such that changes to one may cause respective changes to the other, including values specified in the text boxes 362T.

Figure 23:
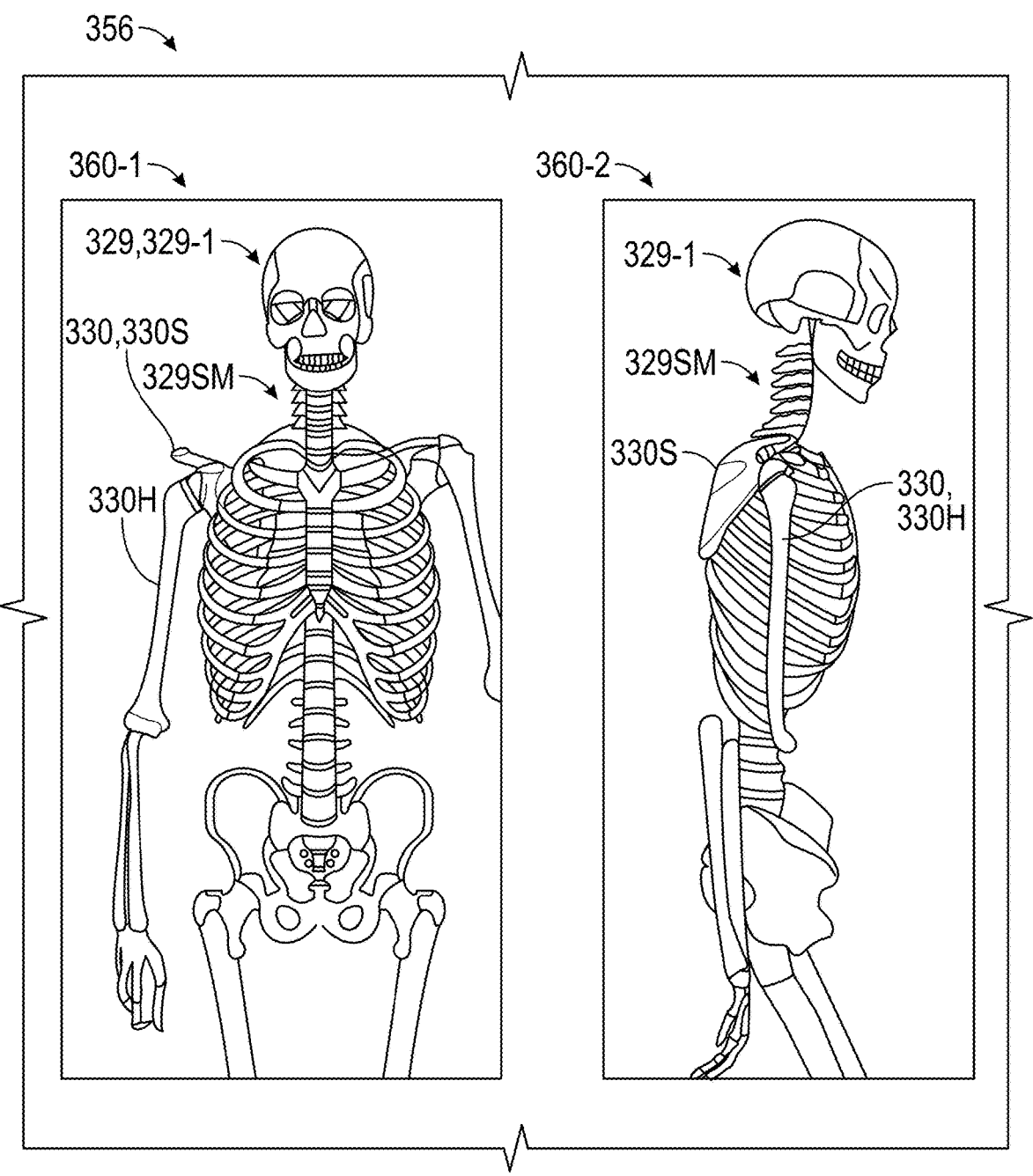

In the implementation of FIGS. 21-23, the anatomical model 329-1 may be associated with a scapular angle (e.g., interior tilt) of 0 degrees. The spatial module 50 may be configured to assign default values for each of the characteristics associated with the objects 362 of the control panel 311 based on a determined and/or selected scapular angle. The spatial module 50 may be configured to arrange the selected bone model(s) 330 relative to each other based on the assigned values. A posture associated with the scapular angle and anatomical model 329-1 of FIG. 21 may be assigned a posture type (e.g., type A).

Referring to FIG. 23, with continuing reference to FIG. 22, the surgeon or clinical user may interact with one or more of the objects 362 to adjust a position of the selected bone model(s) 330, such as the humeral model 330H. The surgeon or clinical user may interact with one or more of the objects 362 to adjust an adduction of the humeral model 330H from a first position (e.g., FIG. 22) to a second position (e.g., FIG. 23). The spatial module 50 may be configured such that unselected bone model(s) 330 may remain in a fixed position during adjustment of the selected bone model(s) 330, which may provide flexibility in determining one or more parameters of a preoperative plan, such as a position and/or orientation of implant(s) associated with respective implant model(s) 332. The surgeon or clinical user may interact with the user interface 356 to observe the effect of the various characteristics with respect to range of motion and one or more acts of daily living and/or lifestyle goals, including any of those disclosed herein.

Figure 24:
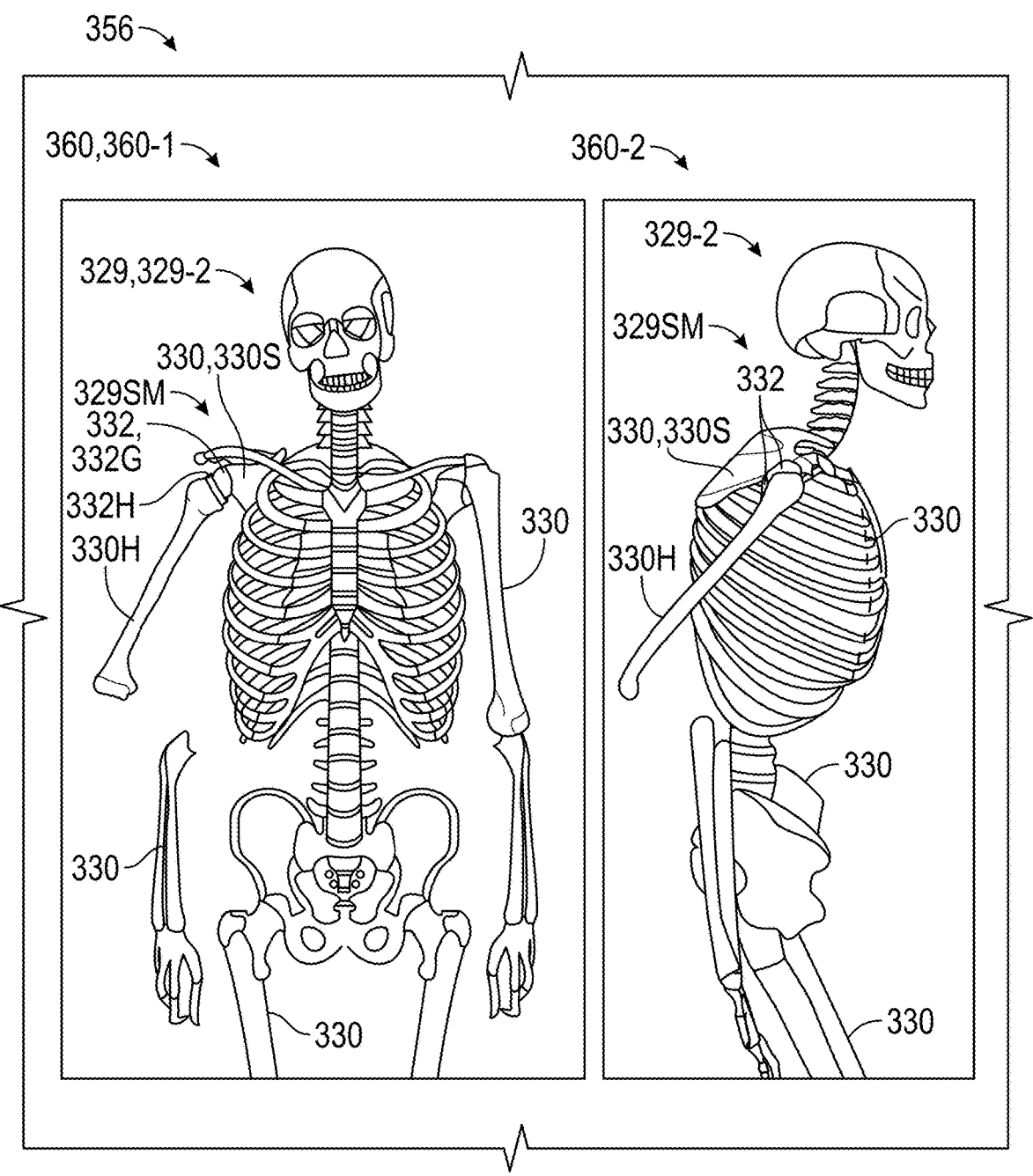
FIGS. 24-26 disclose another shoulder model including a humeral implant mating with a glenoid implant associated with a posture and scapular angle.
Figure 25:
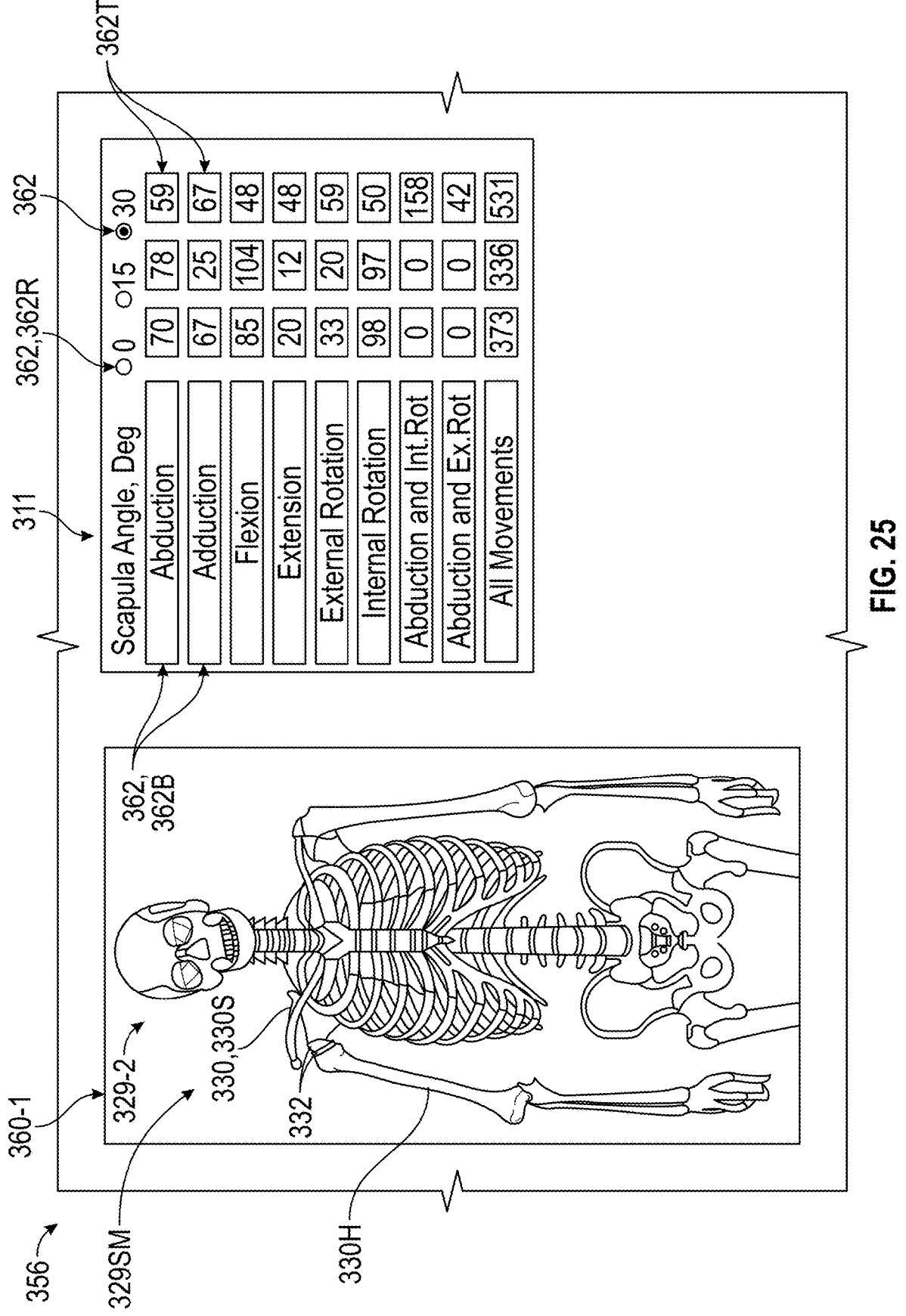
Figure 26:
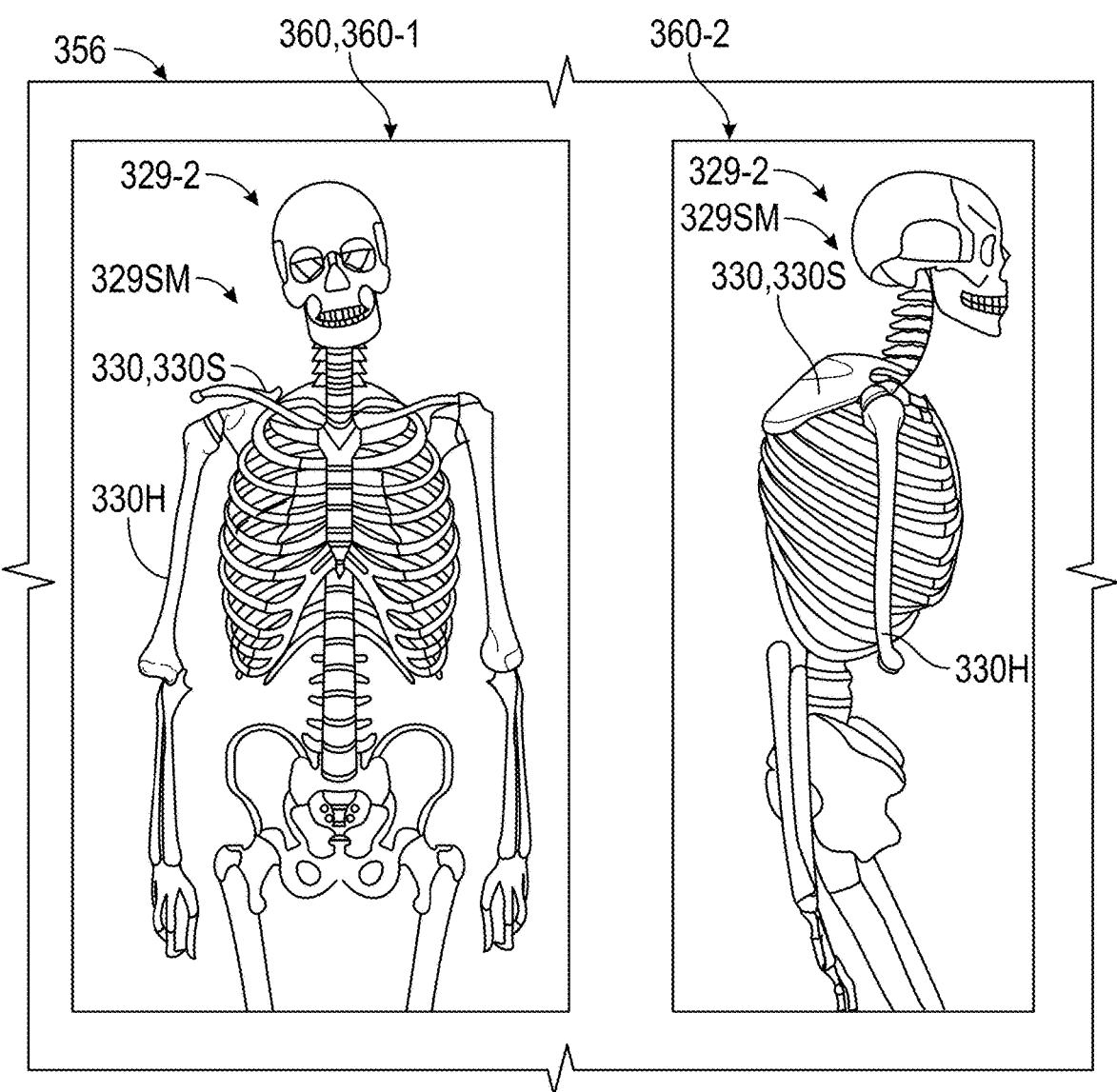

FIGS. 24-26 disclose an implementation of a second anatomical model 329-2 in the display windows 360 of the graphical user interface 356. A posture associated with the second anatomical model 329-2 may differ from a posture associated with the first anatomical model 329-1. The anatomical model 329-2 may be associated with a scapular angle (e.g., interior tilt) of approximately 30 degrees. A posture associated with the scapular angle and anatomical model 329-2 of FIG. 24 may be assigned a posture type (e.g., type C).

The planning system 10 may be configured to establish surgical plans 36 based on the determined postures and/or scapular angles of respective patients. The planning system 10 may be configured to determine posture and/or scapular angle based on an acquisition position of the patient (e.g., upright or laying position). The planning system 10 may be configured to apply a transformation to the acquisition position of the patient to predict or otherwise determine the posture and/or scapular angle of the patient in an upright (e.g., standing) position. The surgeon or clinical user may interact with the planning system 10 to establish a surgical plan 36 based on the determined posture and/or scapular angle to achieve one or more acts of daily living and/or lifestyle goals and/or evaluate range of motion with respect to planned implant positioning, which can improve mobility of the patient.

Figure 27:
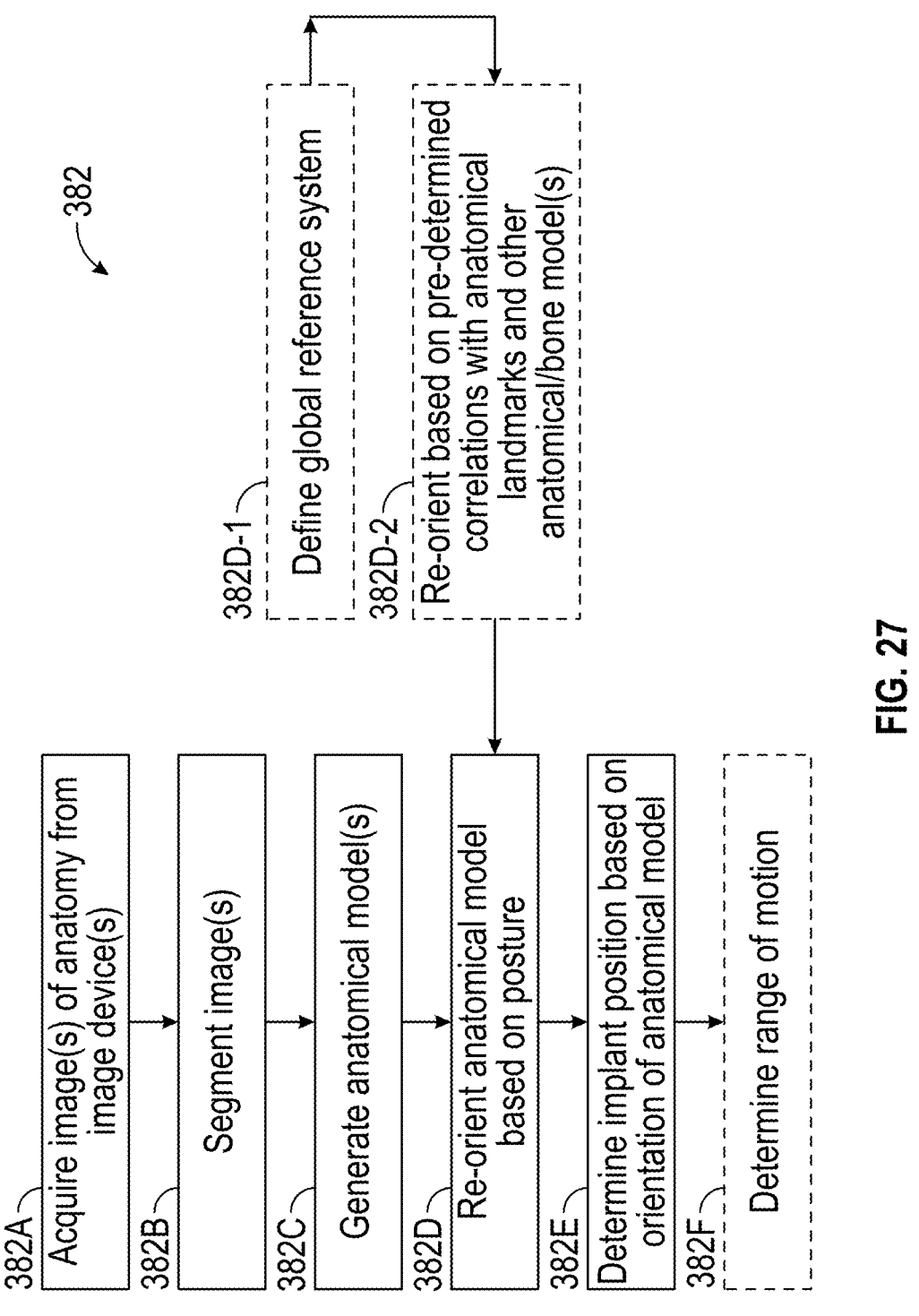
FIG. 27 discloses a method for planning a surgical procedure on a respective patient using a surgical planning system.

FIG. 27 discloses a method for a surgical procedure in a flowchart 382. The method 382 may be utilized to preoperatively plan, implement, evaluate and/or validate aspects of various surgical procedures, such as an arthroplasty for restoring functionality to shoulders, ankles, knees, hips and other joints. The method 382 may be utilized with any of the planning systems and methods, virtual anatomical models and/or bone models disclosed herein, such as the planning system 10. The method 382 may be utilized to determine a posture of the patient. The method 382 may be utilized to establish a position and/or orientation of one or more implants based on an orientation of the anatomy, such as an orientation of the scapula. The orientation of the anatomy may be associated with a posture of a patient. Method 382 may be utilized to determine a posture of the patient. In implementations, the planning method 382 may be utilized to predict or otherwise determine a position, alignment and/or angle of a bone based on a geometry of one or more other bones, including adjoining bone(s) and/or non-adjoining bones of the patient. The method 382 may configured to predict or otherwise determine the position, alignment and/or angle of the bone based on a relationship of the bone to a (e.g., global) reference system and/or one or more kinematic planes and/or axes of the patient. Fewer or additional steps than are recited below could be performed within the scope of this disclosure, and the recited order of steps is not intended to limit this disclosure. The system 10 and any of the associated modules may be configured to implement the features of any of the methods disclosed herein, including method 382. Reference is made to the system 10.

Referring to FIGS. 2 and 27, at step 382A digital imagery of anatomy of a patient may be captured or otherwise obtained by an imaging device 16 (FIGS. 1-2), including any of the imaging devices disclosed herein such as a computed tomography (CT) or magnetic resonance imaging (MRI) device. The digital imagery may include image data which may be captured or otherwise obtained to establish one or more images 26 of the anatomy, such as with the imaging device 16. The data module 46 may receive the image data directly from the imaging device 16 or may acquire the image data by accessing the record or entry associated with the patient from the database 38 (FIG. 2) and/or the patient profile database 64 (FIG. 3). The digital imagery may include any of the anatomy disclosed herein, such as anatomy represented by the bone models 330 and/or anatomical models 329 of FIGS. 21-23. The imaging device 16 may be associated with an acquisition reference system. The acquisition reference system may be associated with axes and a set of coordinate values. The images 26 may be associated with the acquisition reference system of the respective imaging device 16.

Figure 28:
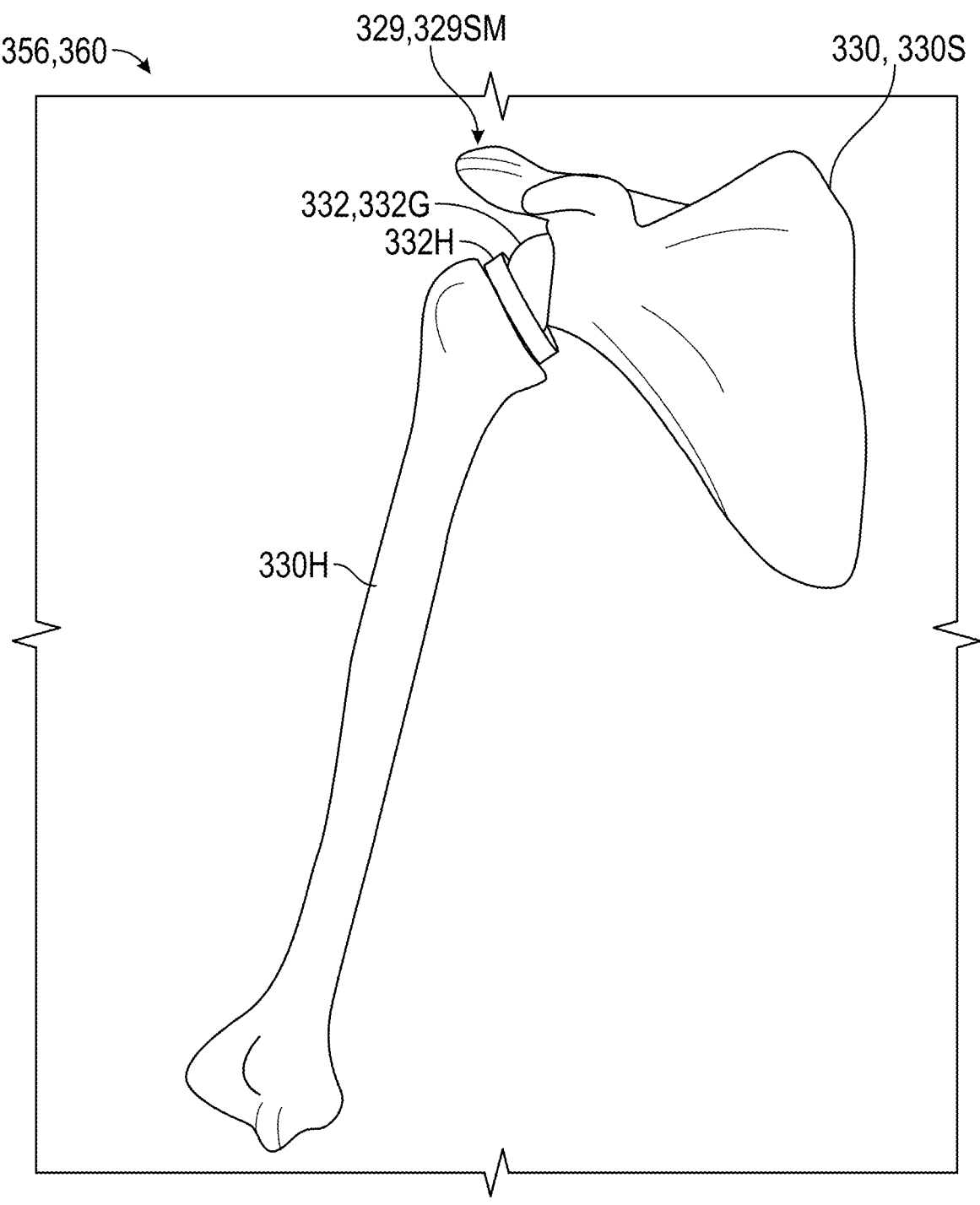
FIGS. 28-32 discloses a shoulder model of a patient.

Referring to FIG. 28, with continuing reference to FIGS. 2 and 27, the images 26 may be associated with an anatomical model 329 and/or bone model(s) 330. The spatial module 50 may be configured to associate the anatomical model 329 with the acquisition reference system. Although FIG. 28 discloses the anatomical model 329 relative to a set of implant models 332, it should be understood that the implant models 332 may be positioned relative to the anatomical model 329 subsequent to establishing a modified instance of the anatomical model 329 associated with a surgical plan 36. The data module 46 may be configured to store an instance of one or more anatomical and bone models and associated coordinate values in the memory 44, such as the anatomical model 329 and/or bone models 330.

The digital imagery may be captured relative to various acquisition positions of a patient with respect to the imaging device 16. The acquisition position of the patient may be generally horizontal. In implementations, the acquisition of the patient may be substantially vertical. Imagery of the patient may be captured while the patient is standing. A posture of the patient in the standing position may deviate from a perfect posture. The imagery may be captured by a standing imaging device.

At step 382B, the digital image(s) 26 may be segmented utilizing various techniques, such as by applying automatic, semi-automatic or manual segmentation to the images 26. The system 10 may be configured to segment the images 26.

At step 382C, one or more anatomical and/or bone models may be generated. The system 10 may be configured to generate one or more anatomical models 29, such as the anatomical model 329. The anatomical model 329 may include one or more bone models 330. The anatomical model 329 may include information specifying an arrangement of the bone models 330 relative to each other.

The anatomical model 329 may include a shoulder model 329SM. The shoulder model 329SM may be associated with the first anatomical model 329-1 of FIGS. 21-23. The bone models 330 may include a scapula bone model 330S associated with a scapula of a patient and a humeral bone model 330H associated with a humerus of the patient.

In implementations, 3D meshes of a scapula and humerus may be reconstructed to establish the scapula bone model 330S and humerus bone model 330H. The scapula model 330S may be established with respect to a local (e.g., scapula) reference system. The local reference system may be associated with a set of coordinate values. The spatial module 50 may be configured to associate the scapula reference system with a scanned (e.g., acquisition) position of the scapula relative to the imaging device 16.

Various techniques for orientation of the anatomy, including the scapular, may be utilized. The anatomy including the scapular may remain in a local (e.g., acquisition) orientation for planning. The acquisition orientation may be associated with the acquisition reference system of the imaging device 16. In implementations, the Z-axis of the acquisition reference system may be horizontal for imaging device 16 and other acquisition systems that may acquire image data of a patient in a horizontal (e.g., laying) position. The Z-axis of the acquisition reference system may be vertical for acquisition systems that may acquire image data of a patient in an upright (e.g., vertical or standing) position. Posture characteristics of the patient may differ between the horizontal and upright positions, such as scapula angle.

At step 382D, the anatomical model(s) and/or bone model(s) may be re-oriented (e.g., registered) from a first reference system to a second, different reference system. In implementations, the anatomical models and/or bone models may be re-oriented based on a posture of the patient and associated posture characteristics. Re-orienting the anatomical models and/or bone models of the patient based on posture may improve implant planning to achieve range of motion and acts of daily living and/or lifestyle goals. The acquisition position of the patient anatomy including the scapular may be determined directly from the digital imagery. The disclosed systems and methods may normalize and/or realign the scapular to a scapular plane in a three dimensional (3D) computer-aided design (CAD) model. One or more measurements and/or other information associated with the patient may be captured preoperatively to manually and/or optically determine the preoperative posture of the patient. In other implementations, re-orienting (e.g., registering) the anatomical model(s) and/or bone model(s) from the first reference system to the second reference system at step 382D may occur without determining the posture of the patient.

The spatial module 50 or another portion of the planning system 10 may be configured to re-orient (e.g., register) at least one or more of the anatomical models and/or bone models from the first reference system to the second reference system. The first reference system may be a local or acquisition reference system. The second reference system may be any of the reference systems disclosed herein, such as a global reference system. The spatial module 50 may be configured to re-orient the bone model 330 in the global reference system based on a selected representative bone model 30, which may be associated with a different patient. The spatial module 50 may be configured to register one or more of the bone models 330 of the patient from the first reference system to the second reference system in response to adjusting one or more coordinate values associated with the respective bone model(s) 330 based on a posture of the patient, including any of the posture parameters disclosed herein. The comparison module 52 may be configured to determine the posture parameter(s) associated with the posture of the patient. The spatial module 50 may be configured to register the bone model 330 of the patient in the global reference system based on the determined posture parameter(s).

The planning system 10 may be configured to normalize one or more data sets in the global reference system, including any of the anatomical models, bone models, implant models and/or databases disclosed herein. Step 382D may include re-orienting the scapula model 330S from its acquisition orientation in the acquisition reference system to the global reference system. The scapula model 330S may be re-oriented utilizing any of the techniques disclosed herein. An orientation of the scapula model 330S in the global reference system may be associated with an anatomical position of the scapula when the patient may be standing, which may be influenced by the posture of the patient.

Various techniques may be utilized to re-orient the anatomical and/or bone models. The spatial module 50 and/or another portion of the system 10 may be configured to register the bone model(s) from the first (e.g., local or acquisition) reference system to the second (e.g., global) reference system based on one or more posture parameters associated with the posture of the patient. The one or more posture parameters may be utilized to establish a transformation between the first reference system and the second reference system. The one or more posture parameters may include a scapular angle associated with a scapula (see, e.g., FIGS. 17A-17C). Various techniques may be utilized to establish the transformation, such as one or more parametric equations and/or matrices.

Figure 30:
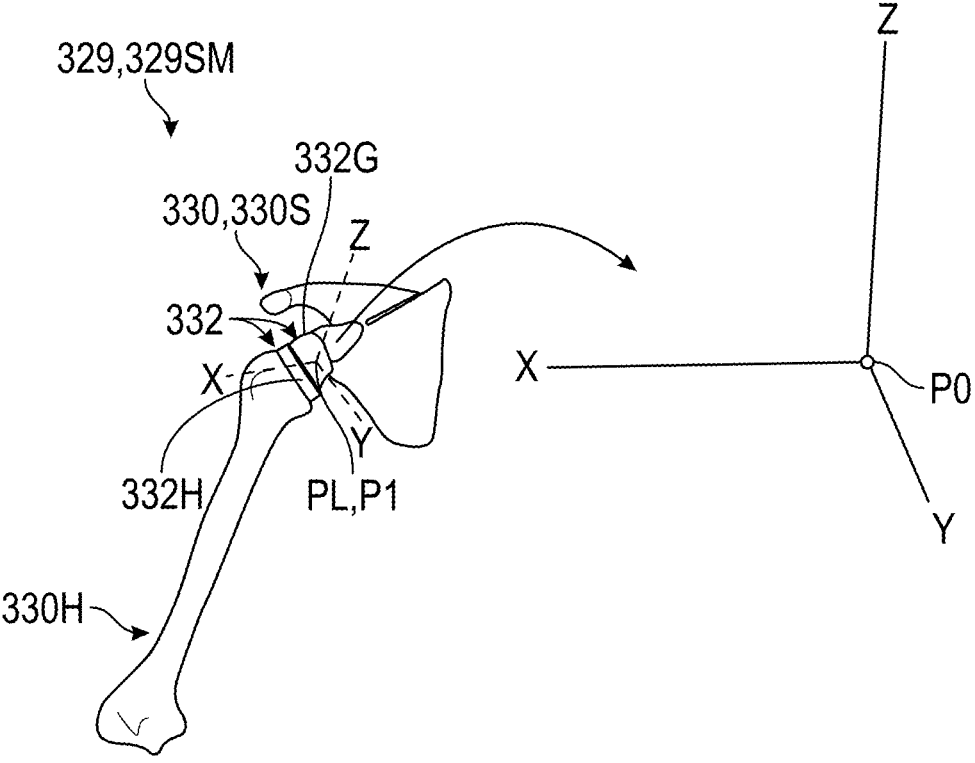

At step 382D-1, the global reference system may be defined (see, e.g., FIG. 30). The planning system 10 may define the global reference system utilizing any of the techniques disclosed herein. The global reference system may be associated with a set of coordinate values. The global reference system may be representative of an anatomical position of the patient, which may differ from an acquisition position associated with the image data acquired by the imaging device 16. The anatomical position may correspond to a posture of the patient in an upright (e.g., standing) position. The global reference system may be established with respect to Z (0, 0, 1), Y (0, 1, 0) and X (1, 0, 0) axes. The Z axis of the global reference system may correspond to a vertical direction. The X and Y axes of the global reference system may extend in respective horizontal directions along a horizontal plane. The global reference system may be associated with an upright position of the patient. In implementations, the global reference system may be established with respect to one or more kinematic planes of a patient, including any of the kinematic planes disclosed herein. The X, Y and Z axes may be established along respective kinematic planes of the patient. Utilizing the techniques disclosed herein, acts of daily living and/or lifestyle goals may be established and/or evaluated based on a posture of the patient. The planning system 10 may be configured to establish and/or evaluate implant position and orientation, range of motion and/or acts of daily living/lifestyle goals of a patient relative to the global reference system. In implementations, the range of motion modeler 101 (FIG. 8) may determine range of motion relative to the global reference system. The various databases disclosed herein may be normalized to the global reference system, including the surgical outcomes database 66, range of motion database 68 and/or anatomical makeup classification database 70 (FIG. 3).

The spatial module 50 may be configured to register the scapula reference system associated with the scapula module 330S to the global reference system, which may include translating and/or rotating the scapula model 330S. The scapula reference system may be established relative to a set of landmarks of the scapula model 330S associated with the scapula, such as three or more landmarks.

Figure 29:
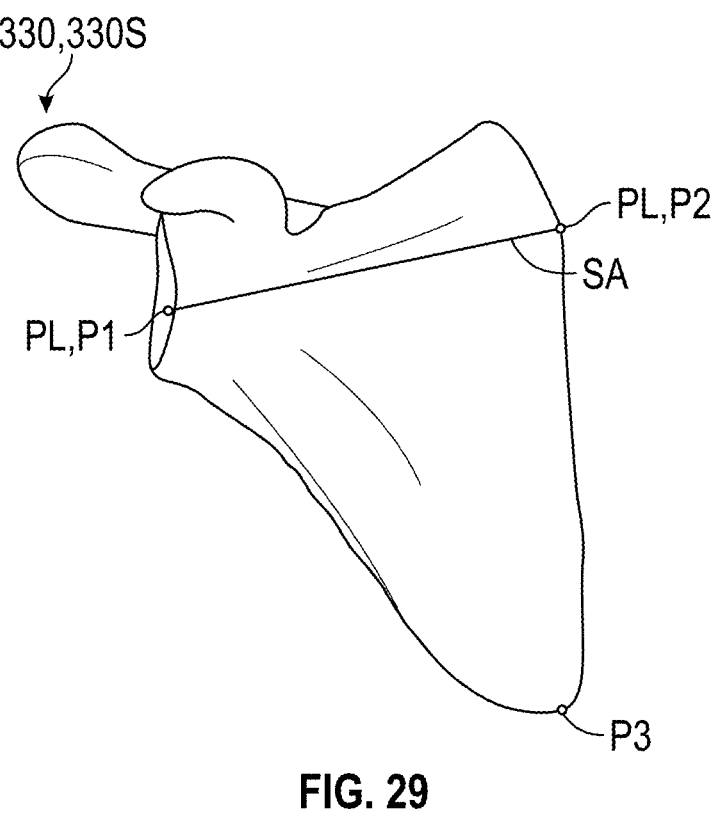

Referring to FIG. 29, with continuing reference to FIGS. 2 and 27-28, a scapula axis SA may be established. The scapula axis SA may extend through a reference point along an articular surface of the scapula model 330S. The articular surface may be associated with a glenoid of the scapula. The scapula axis SA may extend between a first point P1 (e.g., center of the glenoid fossa) and a second point P2 (e.g., trigonum scapulae) of the scapula model 330S.

Figures 31, 32:
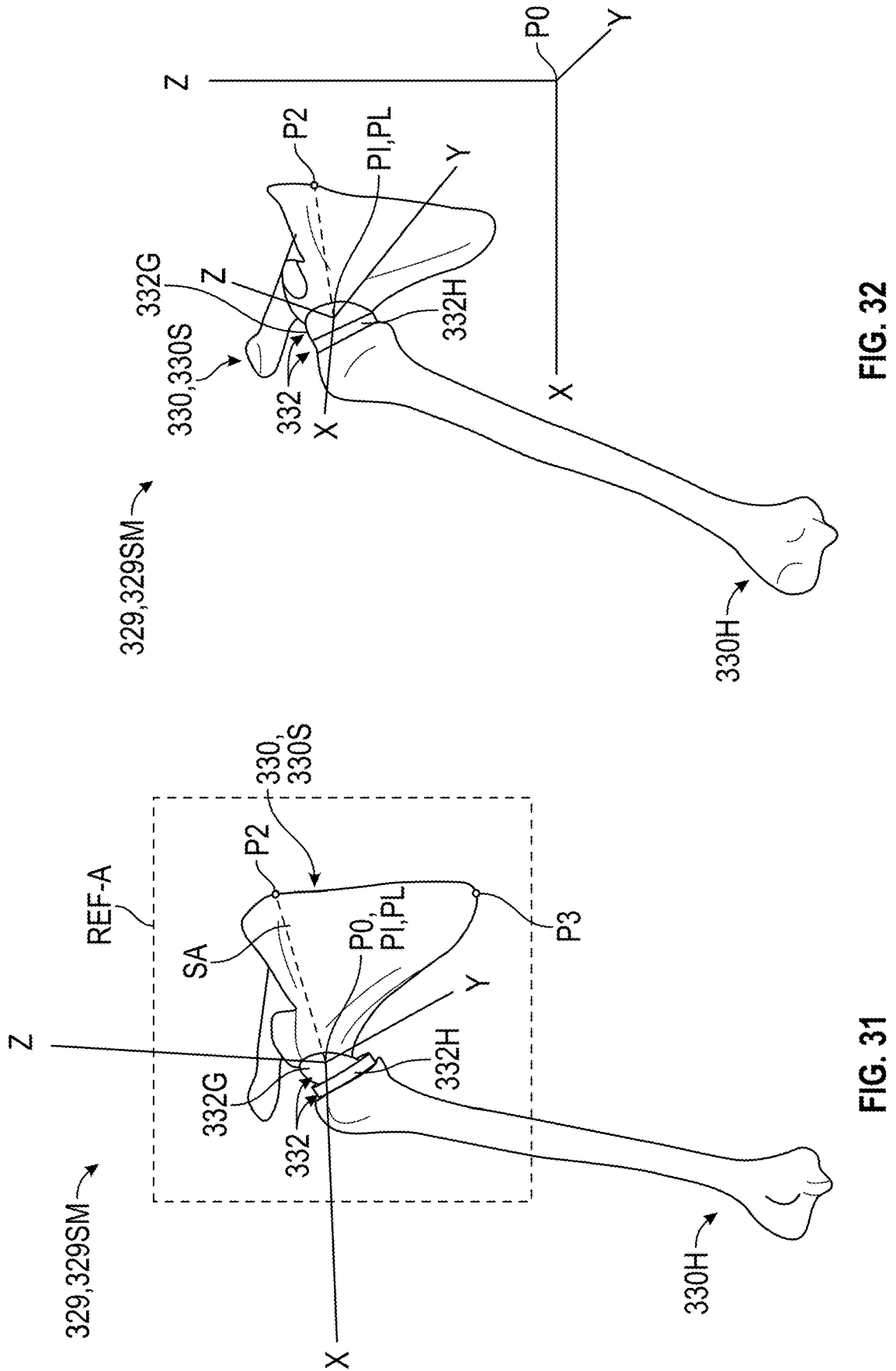

Referring to FIGS. 28 and 31, with continuing reference to FIGS. 2 and 27-28, an anatomical (e.g., scapular) plane REF-A may be established. The scapular plane REF-A may be fit through the scapula model 330S. The scapular plane REF-A may be determined by landmarks or may be a best fit scapular plane. The scapular plane REF-A (FIG. 31) may be established along the scapula axis SA and may extend between the first point P1 at the center of the glenoid fossa and the second point P2 at the trigonum scapulae. The scapular plane REF-A may extend through a third point P3. The third point P3 may be established at an inferior angle of the scapula. The spatial module 50 may be configured to determine the scapula axis SA and/or one or more anatomical landmarks along the scapula model 330S, including the first, second and/or third points P1, P2, P3. The spatial module 50 may be configured to determine the scapular plane REF-A such that the scapular plane REF-A may extend along the scapula axis SA.

Referring to FIG. 30, with continuing reference to FIGS. 2 and 27-29, the scapula model 330S may be associated with a first (e.g., local, scapula or acquisition) reference system. The scapula reference system may have an origin PL. The spatial module 50 may be configured to apply a predefined transformation to the scapula model 330S to re-orient the scapula model 330S from the first reference system to a second, different reference system. The first reference system may be the local reference system. The second reference system may be the global reference system established at step 382D-1. The system 10 may establish a surgical plan 36 associated with the bone model(s) 330 with respect to the global reference system. The surgical plan 36 may include an implant plan associated with an implant. The implant plan may include an implant type, an implant dimension, and/or an implant position and/or orientation associated with an implant model.

Referring to FIG. 31, with continuing reference to FIGS. 2 and 27-30, registering the scapula bone model 330S at step 382D may include adjusting an orientation of the scapula bone model 330S. In implementations, the spatial module 50 may apply the predefined transformation such that the scapula model 330S may be translated and/or rotated, which may cause the scapula reference system of the scapula model 330S to be aligned (e.g., registered) with the global reference system. The origin PL of the scapula reference system may be established at the first point P1 at the center of the glenoid fossa of the scapula model 330S. In the implementation of FIGS. 31, the alignment may occur such that the first point P1 at the center of the glenoid fossa may be positioned at an origin P0 of the global reference system. The system 10 may be configured to execute a predefined transformation of the humeral bone model 330H from a local (e.g., humeral) reference system to the global reference system utilizing any of the techniques disclosed herein regarding the scapula model 330. In implementations, the spatial module 50 may be configured to apply the same predefined transformation associated with the glenoid bone model 330G to the humeral bone model 330H such that a relative position between the glenoid bone model 330G and humeral bone model 330H remains the same between the reference systems. An orientation of the scapula model 330S and the humeral model 330H relative to the global reference system may be representative of a posture of the patient in the anatomical position.

The system 10 may be configured to register one or more implant models 32 in the global reference system according to any of the techniques disclosed herein. In the implementation of FIG. 30, the system 10 may be configured to register the position of one or more implant models 332 in the global reference system. The implant models 332 may be arranged along the glenoid and/or humeral head of the associated bone models 330S, 330H. The implant models 332 may be registered concurrently with the registration of the scapula model 330S and/or humeral model 330H. In other implementations, the implant models 332 may be positioned relative to the glenoid and humeral models 330S, 330H subsequent to registration of the scapula and/or humeral bone models 330S, 330H in the global reference system.

Still other techniques may be utilized to re-orient the anatomical and/or bone model(s) from one reference system to another reference system. The planning system 10 may configured to determine the position of the bone associated with a respective bone model based on a geometry of one or more other bones and associated bone model(s) and/or anatomical model(s), including adjoining bone(s) and/or non-adjoining bones of the patient. In implementations, the planning system 10 may configured to determine the position, alignment and/or angle of the bone associated with a respective bone model based on a geometry of one or more other bones and associated bone model(s) and/or anatomical model(s), including adjoining bone(s) and/or non-adjoining bones of the patient. In implementations, the planning system 10 may configured to determine the position, alignment and/or angle of the bone associated with the respective bone model based on a relationship of the bone to a (e.g., global) reference system and/or one or more kinematic planes and/or axes of the patient. At step 382D-2, the anatomical and/or bone model(s) may be re-oriented from a first reference system to a second reference system based on one or more predetermined correlations with anatomical landmarks and/or the anatomy of one or more other patients. The planning system 10 may be configured to establish the surgical plan in response to comparing the anatomical and/or bone model(s) of the patient and the anatomical and/or bone model(s) of one or more other patient(s) and/or patient population(s). The patient population may exclude the patient.

The system 10 may be adapted to re-orient the bone model(s) 330 and/or anatomical model(s) 329, such as the scapula model 330S, based on a relationship between two or more adjoining and/or non-adjoining bones of the anatomy.

The system 10 may be configured to determine the position of the bone associated with the bone model 330 based on a geometry of another bone relative to the scapula, including adjoining bone(s) such as the humerus and/or non-adjoining bones such as the clavicle and/or one or more ribs (e.g., small rib) of the patient.

Step 382D-2 may include re-orienting (X, Y, Z) the scapular plane REF-A (see, e.g., FIG. 31) of the scapula model 330S based on one or more predetermined correlations. The predetermined correlations may be established with respect to anatomical landmarks and/or SSM/numerical makeup classification. The SSM/numerical makeup classifications may be established utilizing any of the techniques disclosed herein, such as with the statistical shape modeler 72. The planning system 10 may be configured to establish a transformation and associated parameters of the transformation for each anatomical makeup classification 80 based on the predetermined correlations, which may be utilized to register the associated bone model(s) and/or anatomical models(s) from one reference system to another reference system.

In implementations, a global (e.g., common) reference system may be established at step 382D-1 utilizing any of the techniques disclosed herein. The scapula model 330S may be registered to the global reference system utilizing one or more defined landmarks, including any of the anatomical landmarks disclosed herein. The system 10 may be configured to determine a position of one or more landmarks along the scapula and/or other portions of the anatomy. The landmarks may be utilized to define a transformation from the scapula reference system to the global coordinate system (see, e.g., FIG. 30). An orientation of the scapula model 330S and the humeral model 330H relative to the global reference system may be representative of an anatomical position of the patient. Landmarks along the scapula may include the center of the glenoid fossa (e.g., point P1 of FIG. 29), the inferior angle of the scapula (e.g., point P3 of FIGS. 29 and 31), and/or the trigonum scapulae (e.g., point P2 of FIG. 29).

Various techniques may be utilized to determine the landmarks, including any of the techniques disclosed herein. The surgeon or clinical user may interact with the display window 360 and/or another portion of the user interface 356 (e.g., FIGS. 21-23) to specify the landmarks relative to the respective bone model 330, including the scapula model 330S. In implementations, the spatial module 50 may be configured to determine the landmarks along the scapula model 330S and/or other bone models 330 of the anatomical model 329.

Referring to FIGS. 2 and 4, with continuing reference to FIGS. 27-28, the scapula model 330S may be registered in the global reference system based on a statistical shape model (SSM) 75 and assigned numerical makeup classification 80. One or more respective SSMs 75 may be established for the scapula, humerus and/or other bones of the anatomy. In implementations, an anatomical SSM 75 may be established for two or more bones of the anatomy, including non-adjoining and/or adjoining bones such as the scapula and humerus. The statistical shape modeler 72 may be configured to analyze sets of image data 74 for constructing the respective SSM 75. The statistical shape modeler 72 may be configured to determine the position of each landmark within the SSM 75 that may be utilized to transform the bone model(s) 30 from a local reference system to the global reference system. In implementations, the statistical shape modeler 72 may assign an anatomical makeup classification

80 to one or more of the bone models 330, including the scapula model 330S (e.g., FIGS. 27-28).

The statistical shape modeler 72 may query the anatomical makeup classification database 70 to locate bone models 30 stored therein that have similar anatomical makeup classifications 80. The coordinate information of bone models 30 associated with the anatomical makeup classification database 70 may be normalized to the global reference system. In implementations, normalizing the coordinate information may include applying a transformation to the associated bone model(s) 30 from the acquisition reference system to the global reference system utilizing any of the techniques disclosed herein.

The comparison module 52 and/or statistical shape modeler 72 may be configured to select a representative bone model 30 from a set of representative bone models 30 associated with the statistical shape model 75. The statistical shape model 75 and the bone model 330 of the patient may be associated with a common bone of an anatomy, such as the scapula or humerus. The comparison module 52 and/or statistical shape modeler 72 may be configured to assign the anatomical makeup classification 80 of the selected representative bone model 30 to the bone model 330 of the patient. Each representative bone model 30 within a set of representative bone models 30 may be assigned a respective anatomical makeup classification 80 based on the statistical shape model 75. The comparison module 52 and/or statistical shape modeler 72 may be configured to assign the anatomical makeup classification 80 of the selected representative bone model 30 to the bone model 330.

The statistical shape modeler 72 may be configured to assign to the bone model 330 an anatomical makeup classification 80 associated with another patient that is closest to the anatomy encompassed by the bone model 330. The anatomical makeup classification database 70 may include stored information specifying one or more landmarks of the bone model 30 associated with the assigned anatomical makeup classification 80. The bone model(s) 30 associated with the assigned anatomical makeup classification 80 may be registered in the global reference system.

In implementations, establishing a surgical plan 36 for the patient may include selecting a representative bone model 30 from the set of representative bone models 30 associated with the respective statistical shape model 75. The statistical shape model 75 and the representative bone models 30 may be associated with a common bone of an anatomy. Establishing the surgical plan 36 may include comparing the bone model 330 of the patient and the selected representative bone model 30 associated with the SSM 75. The surgical plan 36 may be established based on the bone model 330 in the global reference system.

The landmarks of the bone model 330 may be paired with associated landmarks of the bone model 30 of the assigned anatomical makeup classification 80. The bone model 330 of the patient may be re-oriented such that the pairs of landmarks of the representative and patient bone models 30, 330 may be substantially aligned in the global reference system. A posture of the patient may be determined based on the landmark positions of the representative bone model 30.

In implementations, an instance of the bone model(s) 30 of the assigned anatomical makeup classification 80 in the global reference system may be substantially aligned with the bone model(s) 330 of the patient in the local reference system to determine values for one or more correction angles. The correction angles may include three angles of rotation relative to the axes of the reference system. A transformation may be established based on determined values of the correction angles. The spatial module 50 may be configured to apply the transformation to the respective bone model(s) 330 of the patient to register the bone model(s) 330 in the global reference system. In other implementations, the patient bone model(s) 330 may be registered in the global reference system by substantially aligning the patient bone model(s) 330 with the selected bone model(s) 30 of another patient in the global reference system.

The statistical shape modeler 72 may be configured to utilize the SSM 75 to assign an anatomical makeup classification (AMC) 80 to the anatomical and/or bone model(s) based on one or more bones of the anatomy, such as the scapula. Each AMC 80 may be established for a plurality of bones of the anatomy, including adjoining bones of a joint such as the scapula and humerus and/or non-adjoining bones. In implementations, the statistical shape modeler 72 may be configured to determine the position of the bone associated with bone model 30 based on a geometry of another (e.g., adjoining) bone relative to the scapula, including adjacent bone(s) such as the humerus and/or non-adjoining bones such as the clavicle or one or more ribs (e.g., small rib) of the patient. In implementations, the system 10 may be configured to determine an angle of the rib relative to a reference, such as the Z axis of the reference system. The system 10 may be configured to determine the posture based on the determined rib angle(s). In other implementations, each AMC 80 may be established for a single bone of the patient, such as the scapula or humerus. The statistical shape modeler 72 may be configured to determine a position of the bone relative to the skeletal anatomy based on one or more characteristics of the bone and associated landmarks.

A posture of the patient may be utilized to establish the plurality of AMCs 80N. A posture of the patient may be defined with respect to one or more parameters, including any of the parameters disclosed herein such as the scapular angle (e.g., angle of FIGS. 17A-17C). The statistical shape modeler 72 may be configured to establish the anatomical makeup classifications 80 based on one or more predefined modes (e.g., modes of variation) 76. The parameter(s) associated with posture may establish one or more of the predefined modes 76, including any of the posture parameters disclosed herein such as scapular angle. Predefined modes 76 associated with posture may include a relationship between two or more adjoining and/or non-adjoining bones. The statistical shape modeler 72 may be configured to receive the predefined mode(s) 76 associated with posture as an input. The statistical shape modeler 72 may be configured to assign an AMC 80 to the respective anatomy and associated bone models 30 based on the predefined mode(s) 76 associated with posture. In other implementations, the predefined modes 76 may omit a posture of the patient.

An AMC 80 may be selected based on a (e.g., best) fit between the bone model(s) 30 associated with the AMC 80 and the bone model(s) 330 of the patient. The landmarks of the bone model(s) 30 associated with the selected AMC 80 may be utilized to determine a posture of the patient. In implementations, the landmarks associated with the selected AMC 80 may be utilized to determine various posture characteristics, such as a scapula angle relative to the global reference system. The bone model(s) 330 of the patient may be reoriented from the acquisition orientation to the global reference system by applying a transformation based on the determined posture.

The disclosed systems and methods may be utilized to orient a model of the scapular to substantial match the preoperative posture of the patient, which may be utilized to determine and/or validate range of motion. Various implementations may be utilized in accordance with the teachings disclosed herein, including determining range of motion based on posture information.

Figures 34, 35, 36:
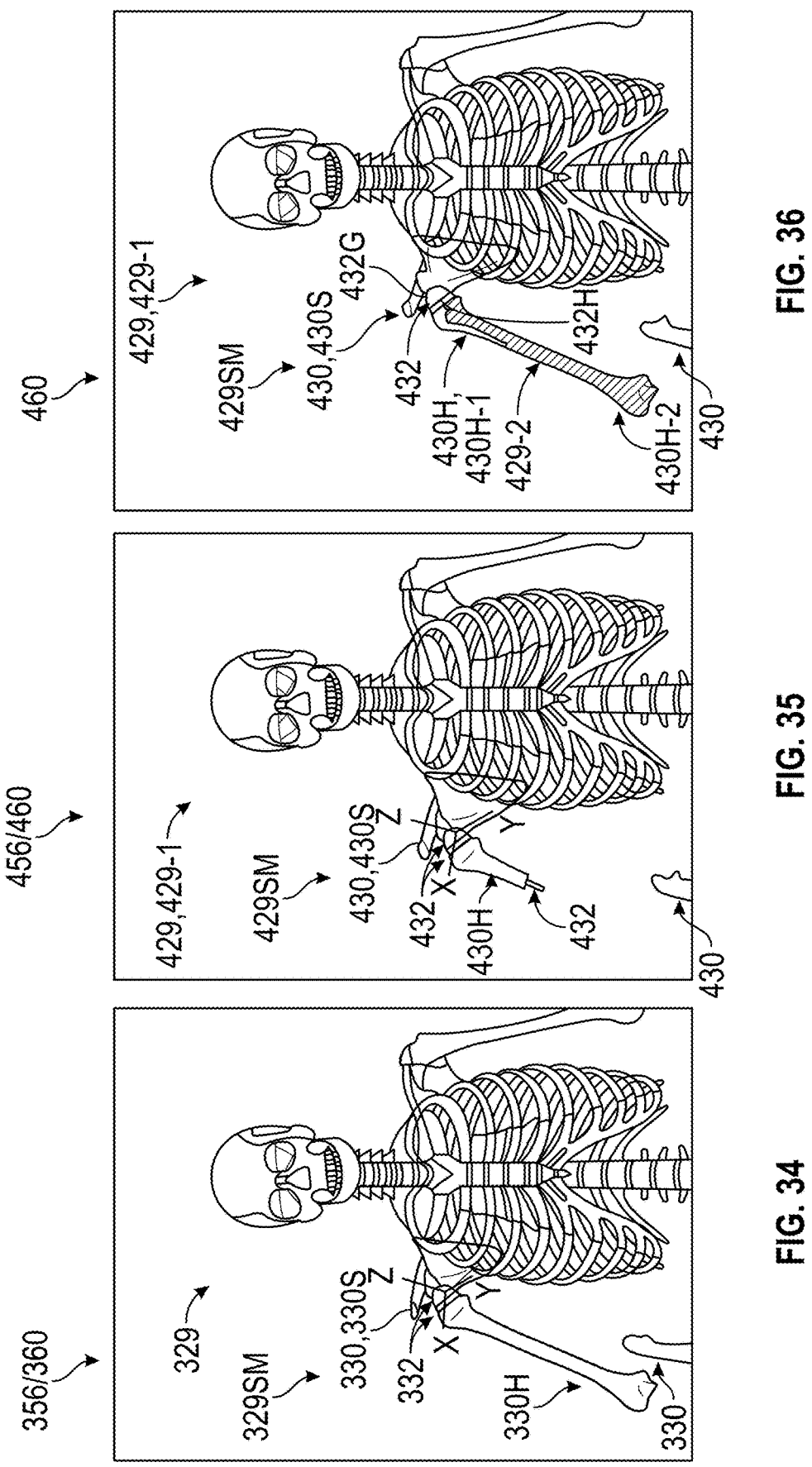
Figures 41, 42, 43:
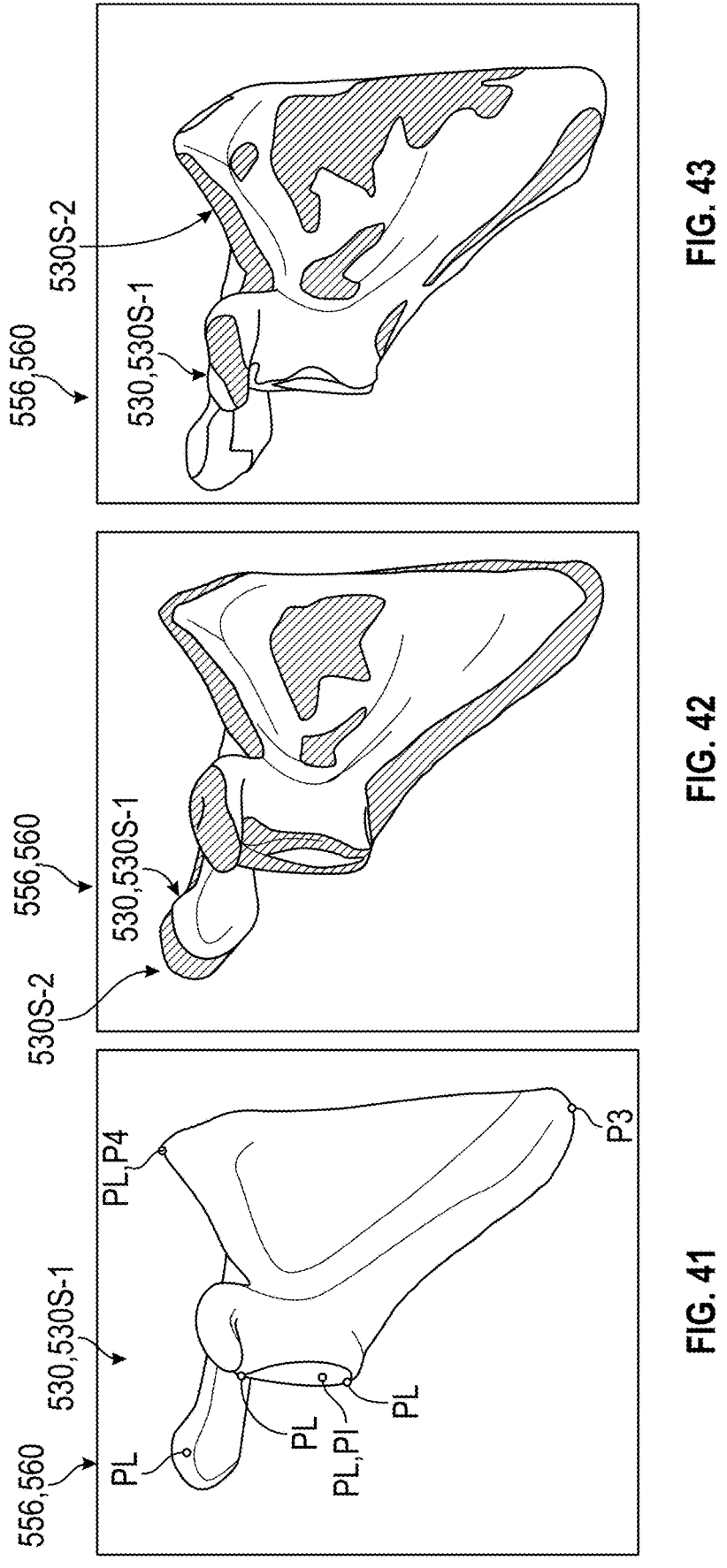
Figures 44, 45:
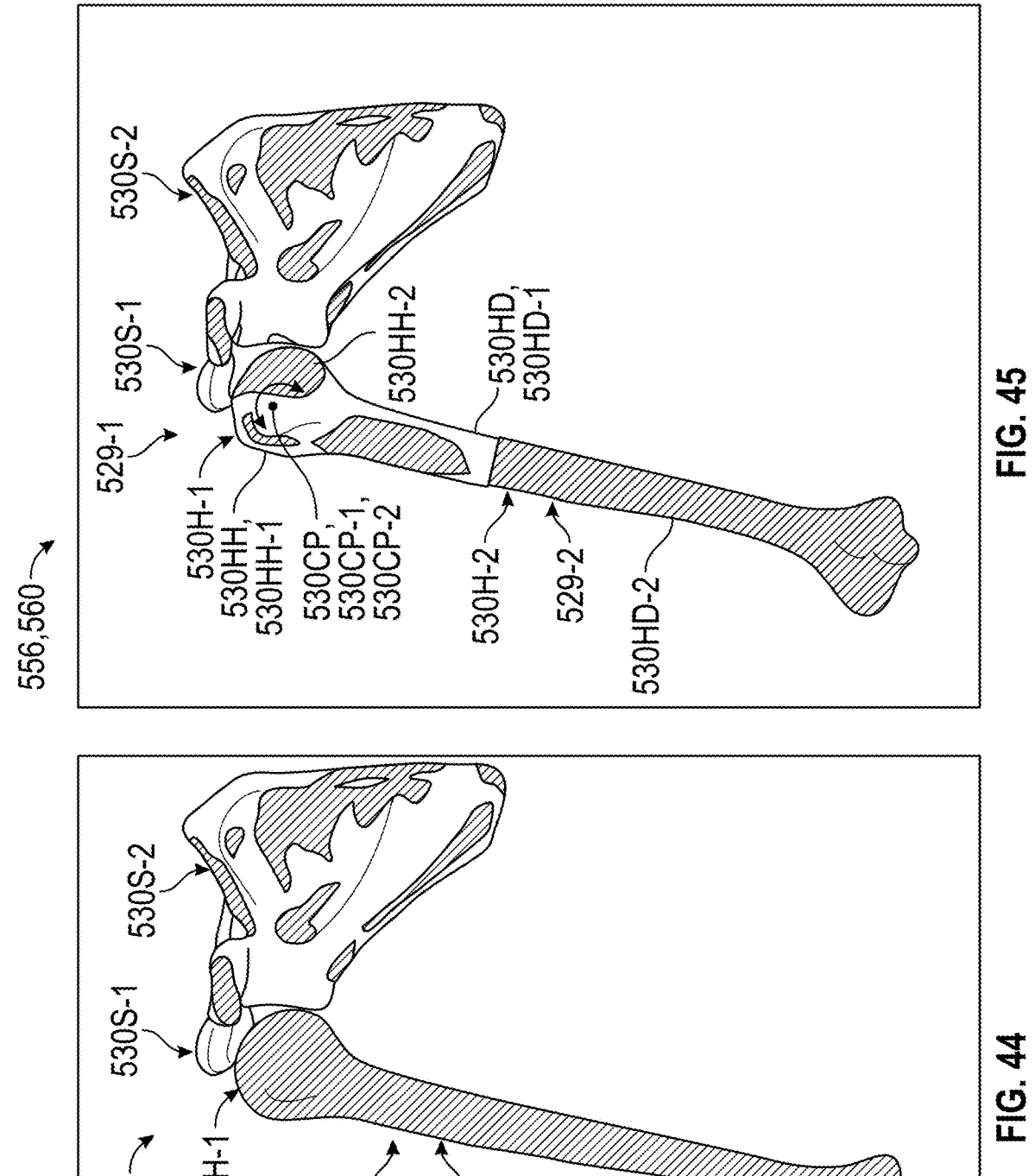

The system 10 may be configured to overlay representative bone model(s) 30 corresponding to the assigned anatomical makeup classification 80 onto the respective bone model(s) 330 of the patient (see, e.g., bone models 430H-1, 430H-2 of FIG. 35, bone models 530S-1, 530S-2 of FIGS. 42-43 and bone models 530H-1, 530H-2 of FIG. 45). The surgeon or clinical user may interact with the user interface 356 to toggle on (and off) visibility of the overlaid bone model(s) 30 associated with the SSM 75. The overlaid bone model(s) 30 associated with the SSM 75 may provide a pre-morbid representation of the patient anatomy, which the surgeon may evaluate to establish, edit and/or approve a surgical plan.

In implementations, step 382D may include substituting the bone model 330 of the patient with the bone model 30 corresponding to the anatomical makeup classification 80 assigned to the bone model 330 of the patient. The anatomical makeup classification database 70 may include coordination information associated with a position of the substitute bone model 30 in the global reference system. The substitute bone model 30 may serve as a pre-morbid representation of the patient anatomy. The pre-morbid representation may omit osteophytes and/or other surface irregularities which may otherwise impede a range of motion of the associated bone. The surgeon may remove the osteophyte and/or otherwise treat the surface irregularities during the surgical procedure. Analyzing range of motion utilizing the substitute bone model 30, including in the global reference system, may provide a relatively more accurate predication of the post-operative range of motion with the surface irregularities removed or otherwise treated.

Referring to FIG. 32, with continuing reference to FIG. 27, at step 382E a position and/or orientation of one or more implants may be determined based on an orientation of the associated bone model, such as the scapula model 330S. The system 10 may be configured to determine a position of one or more implants and associated implant models 332 based on an orientation of the anatomical model 329 and/or bone models 330, including the scapula model 330S, in the respective reference system including any of the reference systems disclosed herein. The implant models 332 may include the glenoid implant model 332G and/or humerus implant model 332H.

The spatial module 50 may be configured to position the implant model(s) 332 and bone model(s) 330 relative to each other in the global reference system based on the implant position specified in the surgical plan 36. The system 10 may be configured to determine an optimal implant position based on a predicted posture of the patient. In implementations, a retrotorsion of the humeral implant model 332H may be adjusted to improve clinical range of motion. The position and orientation of each implant model 332 relative to the respective bone model 330 may be established in the global reference system according to the assigned anatomical makeup classification 80. The surgeon or clinical user may adjust the assigned position and/or orientation of the implant model 332 prior to approving the surgical plan 36. Determining implant position at step 382E may be based on a relationship between two or more adjoining and/or non-adjoining bones that may predicted or otherwise determined utilizing any of the techniques disclosed herein, which may occur additionally or alternatively to determining a posture of the patient.

At step 382F, a range of motion associated with the respective implant model(s) 332 may be determined. Step 382F may include performing a range of motion simulation based on one or more parameters, which may be associated with a posture of the patient. In implementations, the parameters may omit a posture of the patient. The bone model 330 may be associated with a scapula of the patient. The parameters may include a scapular angle associated with the scapula. The system 10 may be configured to perform a range of motion simulation based on the determined posture parameter(s), such as the humerus bone model 330H. The system 10 may be configured to determine range of motion based on the anatomical makeup classification 80 assigned to the bone model(s) 330, including scapula and humeral models 330S, 330H of the scapula and/or humerus, utilizing any of techniques disclosed herein. The range of motion modeler 101 may be configured to perform a range of motion simulation of the bone model 330 in the global reference system based on the posture parameter(s) and/or the assigned anatomical makeup classification 80.

Step 382F may include storing range of motion data derived from the range of motion simulation within a storage system 18 of the system 10. The data module 46 may be configured to store the range of motion data within the storage system 18.

Figure 33:
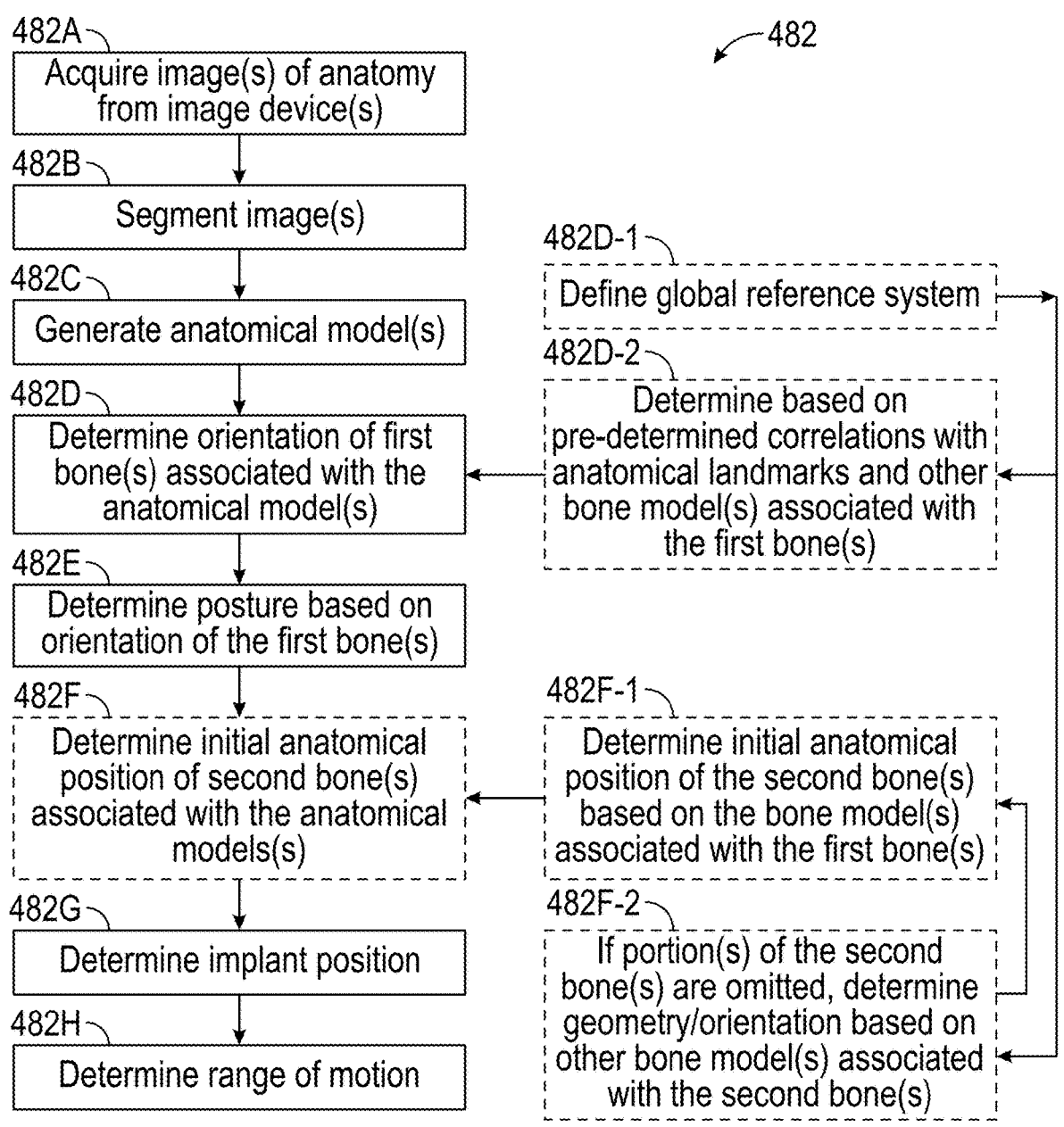
FIG. 33 discloses a method for planning a surgical procedure on a respective patient using a surgical planning system.

FIG. 33 discloses a method in a flowchart 482 for a surgical procedure. The method 482 may be utilized to pre-operatively plan, implement, evaluate and/or validate aspects of various surgical procedures, such as an arthroplasty for restoring functionality to shoulders, ankles, knees, hips and other joints. The method 482 may be utilized with any of the planning systems and methods, virtual anatomical models and/or bone models disclosed herein, such as the planning system 10. The method 482 may be utilized to determine a position and/or orientation of one or more implants based on an orientation the anatomy of a patient, such as a scapula and humerus. The orientation of the anatomy may be associated with a posture of a patient. The method 482 may be utilized to determine a posture of the patient. In implementations, the planning method 482 may be utilized to predict or otherwise determine a position, alignment and/or angle of a bone based on a geometry of one or more other bones, including adjoining bone(s) and/or non-adjoining bones of the patient. The method 482 may configured to predict or otherwise determine the position, alignment and/or angle of the bone based on a relationship of the bone to a (e.g., global) reference system and/or one or more kinematic planes and/or axes of the patient. Fewer or additional steps than are recited below could be performed within the scope of this disclosure, and the recited order of steps is not intended to limit this disclosure. The method 482 may incorporate any of the steps of method 382 disclosed herein, and vice versa. Reference is made to the system 10.

Referring to FIG. 2, with continuing reference to FIG. 33, at step 482A digital imagery of anatomy of a patient may be captured by imaging device(s) 16. The imaging device 16 may include any of the imaging devices disclosed herein. The computing device 40 may be configured to receive image data associated with the patient. In implementations, a shoulder CT scan or MRI may be obtained to establish one or more images 26 of the anatomy, such as with the imaging device 16. The images 26 may be associated with an anatomical model 29. The computing device 40 may be configured to generate anatomical models 29 and/or bone models 30 of the patient and/or one or more other patients based on the image data, including patients associated with a representative patient population. At step 482B, the digital image(s) 26 may be segmented utilizing various techniques, such as by applying automatic or semi-automatic or manual segmentation.

At step 482C, the planning system 10 may be configured to generate one or more anatomical models 29. The anatomical model 29 may include one or more bone models 30. The bone models 30 may be representative of respective bones, including any of the bones disclosed herein such as a scapula and humerus. The anatomical model 29 may include information specifying an arrangement of the bone models 30 relative to each other. Three-dimensional (3D) meshes of the associated bones (e.g., scapula and humerus) may be reconstructed.

At step 482D, an orientation of one or more (e.g., first) bones such as a scapula may be determined. The bone(s) may be associated with an anatomical model(s), such as the anatomical model 329 of FIG. 34. The anatomical model 329 of FIG. 34 may be associated with the anatomical model 329 of FIG. 28. The bone(s) may be associated with a respective bone model, such as the scapula bone model 330S. Various techniques for determining scapular orientation may be utilized, including any of the techniques disclosed herein.

Step 482D may include defining a global reference system at step 482D-1. The global reference system may be defined utilizing any of the techniques disclosed herein.

The orientation of the bone(s) such as the scapula may be measured or otherwise determined utilizing various techniques, including any of the techniques disclosed herein. The planning system 10 may be configured to execute any of the techniques disclosed in the steps of method 382 to measure or otherwise determine the orientation of the bone(s).

Various techniques for determining an orientation of bone(s) associated with the anatomical model at step 482D may be utilized. Referring to FIGS. 35-36, with continuing reference to FIGS. 2, 4 and 33, an anatomical model 429 according to another implementation is disclosed. Step 482D may include determining an orientation of the (e.g., scapula) bone model(s) 430 based on one or more predetermined correlations with anatomical landmarks and/or the anatomy of one or more other patients and/or representative patient populations at step 482D-2. The representative patient population may exclude the patient. The predetermined correlations may be established with respect to anatomical landmarks and/or SSM/numerical makeup classification. The SSM/numerical makeup classifications may be established utilizing any of the techniques disclosed herein. In implementations, a global reference system may be established at step 482D-1 utilizing any of the techniques disclosed herein.

The storage system 18 may be configured to store two-dimensional and/or three-dimensional bone models 30 associated with one or more bones and/or one or more joints of the representative patient population. The bone models 30 may include a first set of bone models 30 and a second set of bone models 30. The first set of bone models 30 may be associated with a first bone of the anatomy. The second set of bone models 30 may be associated with a second bone of the anatomy. Bone models 30 within the first and second sets may be associated with a common anatomical model 29 of a patient.

The bone models 30 and associated bones of the representative patient population may be associated with one or more statistical shape models (SSM) 75. In implementations, two or more adjoining and/or non-adjoining bones associated with the bone models 30 may be associated with the same SSM 75. The planning system 10 may configured to determine the position, alignment and/or angle of the bone associated with a respective bone model based on a geometry of one or more other bones and associated bone model(s) and/or anatomical model(s), including adjoining bone(s) and/or non-adjoining bones of the patient. Step 482D-2 may include analyzing the representative patient population within the SSM 75. The planning environment 28 may be configured to analyze the representative patient population within the associated SSM 75. The SSM 75 may be established based on a statistical significant number of prior cases to characterize variation of the associated bone(s) of the anatomy. In implementations, the SSM 75 may be established based on at least 100 to 1,000 prior cases, or more narrowly at least 10,000 to 20,000 prior cases. The statistical shape modeler 72 may be configured to create a plurality of anatomical makeup classifications 80 based on a plurality of predefined modes (e.g., modes of variation) 76 within the statistical shape model 75. The statistical shape modeler 72 may be configured to receive as an input one or more predefined modes 76. The predefined modes 76 may characterize anatomical differences within the representative patient population and standard deviations 78 of anatomical variances contained within each of the predefined modes 76. The statistical shape modeler 72 may be configured to assign the anatomical makeup classifications 80 to the bone models 30. The storage system 18 may be configured to store the anatomical makeup classifications 80. Step 482D-2 may include identifying the predefined modes 76 within the SSM 75 of the representative patient population.

Predefined modes 76 that may be provided to the statistical shape modeler 72 may include, but are not limited to, any of the predefined modes disclosed herein, including size of the bone(s) and/or portion of the bone(s) (e.g., scapula, glenoid, humerus, humeral head, diaphysis, etc.), amount of inclination, amount of version, amount of retrotorsion (e.g., of humerus), projected amount of glenoid and sagittal neck length, angle of glenoid relative to scapular neck, critical shoulder angle, projection of acromion and/or coracoid, and varus/valgus of humeral head, anatomical landmarks, joint space, pre-operative range of motion, any combinations of the foregoing, etc. In implementations, the predefined modes 76 associated with the scapula and humerus may be the same or may differ. The number of predefined modes 76 may be selected based on an amount of variation associated with individual modes and/or a combination of the modes. An amount of variation of the mode(s) may differ based on the selected anatomy. The predefined modes 76 may include a posture mode associated with a posture of a patient. The posture mode may be established based on two or more adjoining and/or non-adjoining bones of the anatomy. In implementations, the predefined modes 76 may omit a posture of the patient.

FIGS. 36 and 45, with continuing reference to FIGS. 2, 4, 33 and 35, the method 482 may include accessing a first patient three-dimensional model 430S-1/530S-1 of a patient from memory. The first patient model 430S-1/530S-1 may be associated with a first bone of the patient. The method 482 may include accessing a second patient three-dimensional model 430H-1/530H-1 of the patient from the memory. The second patient model 430H-1/530H-1 may be associated with a second, different bone of the patient. The statistical shape modeler 72 may be configured to select a first representative (e.g., scapula) three-dimensional bone model (e.g., 530S-2 of FIG. 45) and/or a second representative (e.g., humerus) three-dimensional bone model 430H-2/530H-2 associated with a representative anatomical model

429-2/529-2 in response to varying one or more of the predefined modes 76 within the SSM 75. Selecting the anatomical model 429-2/529-2 may occur in response to varying one or more of the predefined modes 76 within the SSM 75.

The statistical shape modeler 72 may be configured to assign the anatomical makeup classification 80 associated with the first representative model 530S-2 to the first patient bone model 430S-1/530S-1. The statistical shape modeler 72 may be configured to assign the anatomical makeup classification 80 associated with the second representative model 430H-2/530H-2 to the second patient bone model 430H-1/530H-1. The range of motion modeler 101 may be configured to perform a range of motion simulation for the assigned anatomical makeup classification 80 of the respective bone. The statistical shape modeler 72 may be configured to assign the anatomical makeup classification(s) 80 to the bone models 430S-1/530S-1 and/or 430S-2/530S-2 based on a posture mode. The statistical shape modeler 72 and/or comparison module 52 may be configured to determine one or more posture parameters associated with a posture of the patient based on the anatomical makeup classification 80 associated with the representative model 430S-2/530S-2 of the scapula and/or second representative model 430H-2/530H-2 of the humerus associated with another patient of the representative patient population.

The orientation of a selected bone model 430/530 of the patient may be measured based on the SSM 75. In implementations, the scapula orientation of a scapular model 530S in 3D space may be measured based on a SSM 75 associated with the scapula. In the implementation of FIGS. 36 and 45, the scapula bone model 430S-1/530S-1 and humerus bone model 430H-1/530H-1 may be associated with the anatomical model 429-1/529-1 of the patient. The scapula bone model 430S-2/530S-2 and humerus bone model 430H-2/530H-2 may be representative bone models associated with a representative anatomical model 429-2/529-2 of another patient of the representative patient population.

The anatomical makeup classification database 70 may include coordinate information associated with a position of each bone model 30 in the global reference system and/or respective acquisition reference system. The scapula SSM 75 may be utilized to select a bone model 30 associated with the anatomical makeup classification database 70 that is closest to the anatomy encompassed by the bone model 430/530 of the respective bone. The selected bone model 30 may be associated with a respective AMC 80. One or more posture parameters associated with the selected bone model 30 may be predetermined, such as scapula angle.

The comparison module 52 may be configured to select a first representative model 530S-2 from the first set of the bone models 30 in response to comparing the first representative bone model 530S-2 to the first patient bone model 430S-1/530S-1 associated with a first bone of the patient, such as the scapula. The first representative model 530S-2 may be associated with a second representative model 430H-2/530H-2 of the second set of the bone models 30. The first patient models 430S-1/530S-1 and second patient model 430H-1/530H-1 may establish a first spatial relationship relative to each other. The second patient model 430H-1/530H-1 may be associated with a second bone of the patient, such as the humerus. The first and second representative bone models 530S-2, 430H-2/530H-2 may establish a second spatial relationship. The first bone and the second bone may be adjoining or non-adjoining bones, including any of the bones disclosed herein. The first and second spatial relationships may be based on one or more landmarks associated with the first bone and/or the second bone, including any of the landmarks disclosed herein.

The comparison module 52 may be configured to determine at least one or more patient characteristics associated with the first bone and/or the second bone of the patient in response to comparing the first and second spatial relationships. The patient characteristics may be associated with a posture of the patient. The comparison module 52 may be configured to establish an implant plan based on the patient characteristic(s). The spatial module 50 may be configured to determine a (e.g., spatial) deviation between the first spatial relationship established by the bone models 430S-1/530S-1, 430H-1/530H-1 of the patient and the second spatial relationship established by the representative bone models 530S-2, 430H-2/530H-2 associated with another patient of the representative patient population. The comparison module 52 may be configured to determine the patient characteristic(s) based on the spatial deviation.

The comparison module 52 may be configured to compare the first representative bone model 430S-2/530S-2 to the patient bone model 430S-1/530S-1 in response to causing the spatial module 50 to at least partially or substantially fit a volume of the first representative bone model 530S-2 and a volume of the patient bone model 430S-1/530S-1 to each other. The comparison module 52 may be configured to compare the second representative bone model 430H-2/530H-2 to the patient bone model 430H-1/530H-1 in response to causing the spatial module 50 to at least partially or substantially fit a volume of the representative bone model 430H-2/530H-2 and a volume of the patient bone model 430H-1/530H-1 to each other.

A transformation may be applied to the selected bone model 30. The spatial module 50 may be configured to apply the transformation. The transformation may be established by re-orienting (e.g., adjusting) the selected bone model 30 to substantially align with the scapula bone model 430S-1/530S-1 of the patient (see, e.g., patient and representative bone models 530S-1, 530S-2 of FIG. 42). Once completed, the orientation of patient scapula of the associated scapula bone model 430S-1/530S-1 may be computed based on the applied transformation to the assigned bone model 30. In implementations, the spatial module 50 may be configured to adjust a position of the patient bone model 430S-1 and/or a position of the patient bone model 430H-1 based on the determined patient characteristic(s).

The spatial module 50 may be configured to register the first patient bone model 430S-1/530S-1 and/or the second patient bone model 430H-1/530H-1 from a local reference system to a global reference system based on the determined patient characteristic(s). The planning environment 28 may be configured to establish a surgical plan associated with the patient bone model 430S-1/530S-1 of the scapula and/or the patient bone model 430H-1/530H-1 of the humerus in the global reference system.

Step 482D-2 may include selecting an anatomical three-dimensional model 429-2/529-2 from a plurality of three-dimensional anatomical models 29 based on the first patient model 430S-1/530S-1 and the second patient model 430H-2/530H-2. The anatomical models 29 may be associated with one or more bones and/or one or more joints of a representative patient population. The anatomical models 29 may be associated with the first bone and the second bone of the representative patient population. Selecting the anatomical model 429-2/529-2 may occur in response to at least partially fitting the bone models 530S-2, 430H-2/530H-2 of the anatomical model 429-2/529-2 to the respective patient bone models 430S-1/530S-1, 430H-1/530H-1 of the anatomical model 429-1/529-1 in the same reference system.

At step 482E, a posture of the patient associated with the anatomical model 429 may be determined. The posture may be determined based on an orientation of the scapula model 430S/530S associated with the anatomical model 429/529. Step 482E may include determining one or more characteristics associated with a posture of the patient based on the selected anatomical model 429-2/529-2. In implementations, step 482E may be omitted.

The method 482 may include predicting or otherwise determining the position, alignment and/or angle of a bone (e.g., humerus) associated with a respective bone model based on a geometry of one or more other bones (e.g., scapula) and associated bone model(s) and/or anatomical model(s), including adjoining bone(s) and/or non-adjoining bones of the patient. At step 482F, an initial anatomical position of another (e.g., second) bone of the anatomy associated with the anatomical model 429 may be determined, such as a humerus associated with the humerus bone model 430H/530H. Various techniques may be utilized for determining the anatomical initial humerus position, including any of the techniques disclosed herein such as the techniques disclosed at step 482D. The initial anatomical position of the other bone (e.g., humerus) may be determined based on the determined posture at step 482E. In implementations, the anatomical initial humerus position may be based on a relationship of the bone to a (e.g., global) reference system and/or one or more kinematic planes and/or axes of the patient, and determining a posture of the patient may be omitted. Although the techniques of step 482F primarily refer to the humerus relative to the scapula, it should be understood that the techniques may be utilized for any two adjoining and/or non-adjoining bones of the anatomy. In implementations, step 482D may be utilized to determine an orientation of the humerus, and step 482E may be utilized to determine an orientation of the scapula.

Step 482F may include determining the anatomical initial position of other bone model(s) 430/530, such as the humerus bone model 430H-1/530H-1, based on an anatomical SSM 75 associated with two or more bones of the anatomical (e.g., scapula and humerus). Step 482F-1 may include determining the anatomical initial position of the humerus bone model 430H-1/530-1 relative to a selected bone model 30 associated with an AMC 80 assigned to the scapula bone model 430S-1/530-1. The bone model 430H-2/530H-2 assigned to the humerus bone model 430H-1/530H-1 may be associated with the same patient as the bone model 530S-2 assigned to the scapula bone model 430S-1/530S-1. The initial anatomical position may be determined based on a relative position between the respective bone models.

The humerus bone model 430H-1/530H-1 may be associated with the same patient as the scapula bone model 430S-1/530S-1. The representative humerus bone model 430H-2/530H-2 may be associated with a different patient, including a real patient associated with a prior case or a hypothetical patient. The humerus bone model 430H-2/530H-2 may be assigned based on the SSM 75 utilizing any of the techniques disclosed herein. In implementations, the planning system 10 may determine one or more landmarks associated with the bone based on the assigned bone model 430H-2/530-2 associated with the SSM 75.

Still referring to FIGS. 35-36, with continuing reference to FIGS. 2, 4 and 33, one or more portions of a bone may be omitted from image data associated with the image(s) 26. A distal portion of a long bone such as the humerus may be included in imagery and/or the humerus bone model of the anatomy (see, e.g., humerus model 330H of FIG. 34). Another portion of the bone may be omitted from the image data and/or humerus bone model, such as a distal (or proximal) portion of the humerus model 430H. The planning system 10 may be configured to determine an initial anatomical position of another adjoining and/or non-adjoining bone (e.g., humerus) in the anatomical model 429 based on a completeness of the acquisition information.

Determining an initial anatomical position of other bone(s) such as the humerus at step 482F-1 may include determining a geometry and/or orientation of the omitted portion(s) of the bone at step 482F-2. Step 482F-2 may include determining a geometry and/or orientation of the omitted portion(s) based on a SSM 75 associated with the bone. The system 10 may be configured to predict or compute a distal portion of the humerus based on the humerus SSM 75. In implementations, the SSM 75 may be associated with two or more adjoining and/or non-adjoining bones of the anatomy, such as the scapula and humerus. In implementations, the humerus SSM 75 may be utilized to select a representative bone model 430H-2 associated with the anatomical makeup classification database 70 that is closest to the anatomy associated with the (e.g., partial) bone model 430H-1 of the patient. The planning system 10 may be configured to substitute the humerus bone model 430H-1 of the patient with the bone model 430H-2 corresponding to the assigned AMC 80. A representation of the omitted portion(s) of the bone may be established by a selected bone model 30 associated with the statistical shape model 75, such as the humerus bone model 430H-2.

The planning system 10 may be configured to associate the anatomical model 429-1 of the patient with two or more instances of a bone model 430 associated with the same bone of the anatomy to establish the representation of the omitted portion(s) of the bone, such as the patient and representative bone models 430H-1, 430H-2. The planning system 10 may be configured to determine the geometry of the omitted portions and/or an orientation of the bone utilizing any of the techniques disclosed herein. Step 482F-2 may include determining the geometry and/or orientation of the omitted (e.g., distal) portion of the humerus based on the representative humerus bone model 430H-2.

Referring to FIGS. 36 and 37A-37B, with continuing reference to FIGS. 2 and 33, the spatial module 50 may be configured to orient the humerus bone models 430H-1, 430H-2 relative to each other. The spatial module 50 may be configured to align the bone models 430H-1, 430H-2 with each other utilizing any of the techniques disclosed herein. The spatial module 50 may be configured to re-orient or otherwise move the bone models 430H-1, 430H-2 together relative to other bone model(s) 430 and/or a reference point (e.g., origin) of the reference system to determine the initial anatomical position of the associated bone (see, e.g., FIGS. 38A-38B). The spatial module 50 may be configured to apply a predetermined transformation to re-orient or otherwise move the bone models 430H-1, 430H-2. In implementations, the spatial module 50 may be configured to re-orient or otherwise move the representative bone model 430H-2, but not the patient bone model 430H-1, to determine the initial anatomical position of the humerus. In implementations, the planning system 10 may be configured to determine one or more landmarks associated with the omitted portion(s) of the bone based on the assigned representative bone model 430H-2 associated with the SSM 75.

The system 10 may be configured to compute an anatomical initial position of the adjoining or non-adjoining bone, such as the humerus. In the implementation of FIGS. 37A-37B and 38A-38B, the system 10 may be configured to rotate a diaphysis of the humeral model 430H around a center of the humeral head to align the diaphysis with the Z axis of the global reference system. The system 10 may be configured to apply external or internal rotation to align the humeral epicondyle axis with a coronal plane of the scapula model 430S.

The display module 48 may be configured to display a representation of the omitted portion(s) in the display windows 460 of the user interface 456. The display module 48 may be configured to display the humerus bone models 430H-1, 430H-2 overlaid with each other in the display window 460. In implementations, the surgeon or clinical user may interact with the user interface 456 to selectively view the first and/or second humerus bone models 430H-1, 430H-2 in the display window 460.

The system 10 may be configured to automatically generate a preoperative surgical plan 36 (FIG. 2) based on the anatomical scapula pose and/or anatomical humerus position. The preoperative plan 36 may specify various parameters (e.g., implant type, size and orientation). The surgical plan 36 may include an implant plan associated with one or more implants to treat a patient.

At step 482G, a position and/or orientation of one or more implant models 432 may be determined. The implant models 432 may include a first (e.g., glenoid) implant model 432G and/or a second (e.g., humerus) implant model 432H. The implant models 432G, 432H may be configured to mate with each other. The system 10 may be configured to determine an optimal implant position based on a predicted posture, which may be determined at step 482E. The system 10 may be configured to establish an implant plan based on one or more posture parameters, which may be determined utilizing any of the techniques disclosed herein. Step 482G may include establishing the implant plan associated with the first bone and/or the second bone of the patient in response to determining the characteristic(s) associated with the patient, such as posture. Step 482G may include applying a correction factor to a default implant position and/or orientation based on the determined posture characteristic(s). The correction factor may be established based on a specific posture value (e.g., scapula angle). Determining implant position at step 482G may be based on a relationship between two or more adjoining and/or non-adjoining bones that may be predicted or otherwise determined utilizing any of the techniques disclosed herein, which may occur additionally or alternatively to determining a posture of the patient.

At step 482H, a range of motion associated with one or more bones of the anatomy may be determined. The range of motion may be based on the position and/or orientation of the implant model(s) 432 determined at step 482F. In implementations, humeral implant retrotorsion associated with the humeral implant model 432H may be adjusted to improve clinical range of motion. The range of motion modeler 101 and/or another portion of the planning environment 28 may be configured to performing a range of motion simulation based on one or more patient characteristics that may be determined utilizing any of the techniques disclosed herein. Based on the anatomical scapula pose, anatomical initial humerus position and/or selected implant(s) (e.g., type, size and orientation), the system 10 may be configured to predict or compute range of motion outcomes for the current patient associated with the anatomical model 429-1 of the patient.

Other techniques may be utilized to determine a geometry and/or orientation of omitted portion(s) of the bone and/or an initial anatomical position of the bone. The planning system 10 may be configured to predict or otherwise determine a geometry and/or orientation of omitted portion(s) of a bone, including a distal or proximal portion of a long bone such as a humerus. In implementations, the system 10 may be configured to determine a geometry and/or orientation of the bone associated with the omitted or incomplete bone information based on a relationship to another adjoining and/or non-adjoining bone, such as the scapula. The predicted geometry and/or orientation of the omitted portion(s) of the bone may be utilized to determine a pre-morbid anatomy of the patient. The predicted geometry and/or orientation of the omitted portion(s) of the bone may be utilized to determine a posture of the patient, including a pre-morbid length of a long bone such as the humerus and position and/or orientation of an associated joint such as the elbow of the patient. The predicted geometry and/or orientation information may be utilized to establish an implant plan associated with the patient bone, including adjusting a default starting position and/or orientation of an implant.

Figure 39:
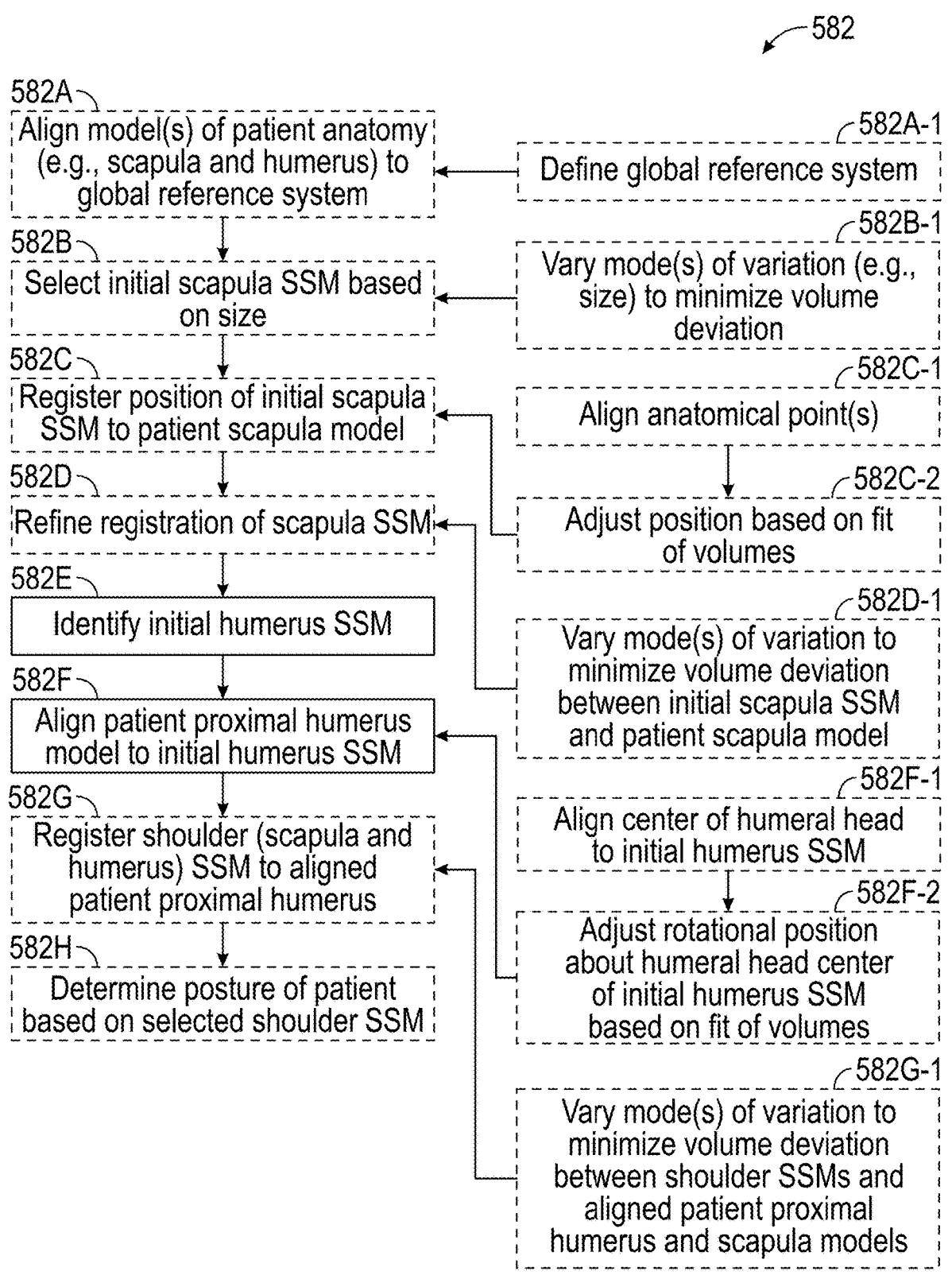
FIG. 39 discloses another method for planning a surgical procedure on a respective patient using a surgical planning system, in which a portion of a bone may be omitted from image data.

FIG. 39 discloses a method for a surgical procedure in a flowchart 582. The method 582 may be utilized to pre-operatively plan, implement, evaluate and/or validate aspects of various surgical procedures, such as an arthroplasty for restoring functionality to shoulders, ankles, knees, hips and other joints. The method 582 may be utilized with any of the planning systems and methods, virtual anatomical models and/or bone models disclosed herein, such as the planning system 10. The method 582 may be utilized to predict or otherwise determine a geometry and/or orientation of omitted portion(s) of a bone, including a distal or proximal portion of a long bone such as a humerus. The orientation of the bone may be associated with a posture of a patient. In implementations, the method 582 may be utilized to predict or otherwise determine a position, alignment and/or angle of a bone associated with the omitted portion(s) based on a geometry of one or more other bones, including adjoining bone(s) and/or non-adjoining bones of the patient, which may occur additionally or alternatively to determining a posture of the patient. Fewer or additional steps than are recited below could be performed within the scope of this disclosure, and the recited order of steps is not intended to limit this disclosure. The method 582 may incorporate any of the steps of method 382 and/or method 482 disclosed herein, and vice versa. In implementations, the step(s) of method 582 may be incorporated into step 482F of method 482 (FIG. 33). Reference is made to the system 10.

Figure 40:
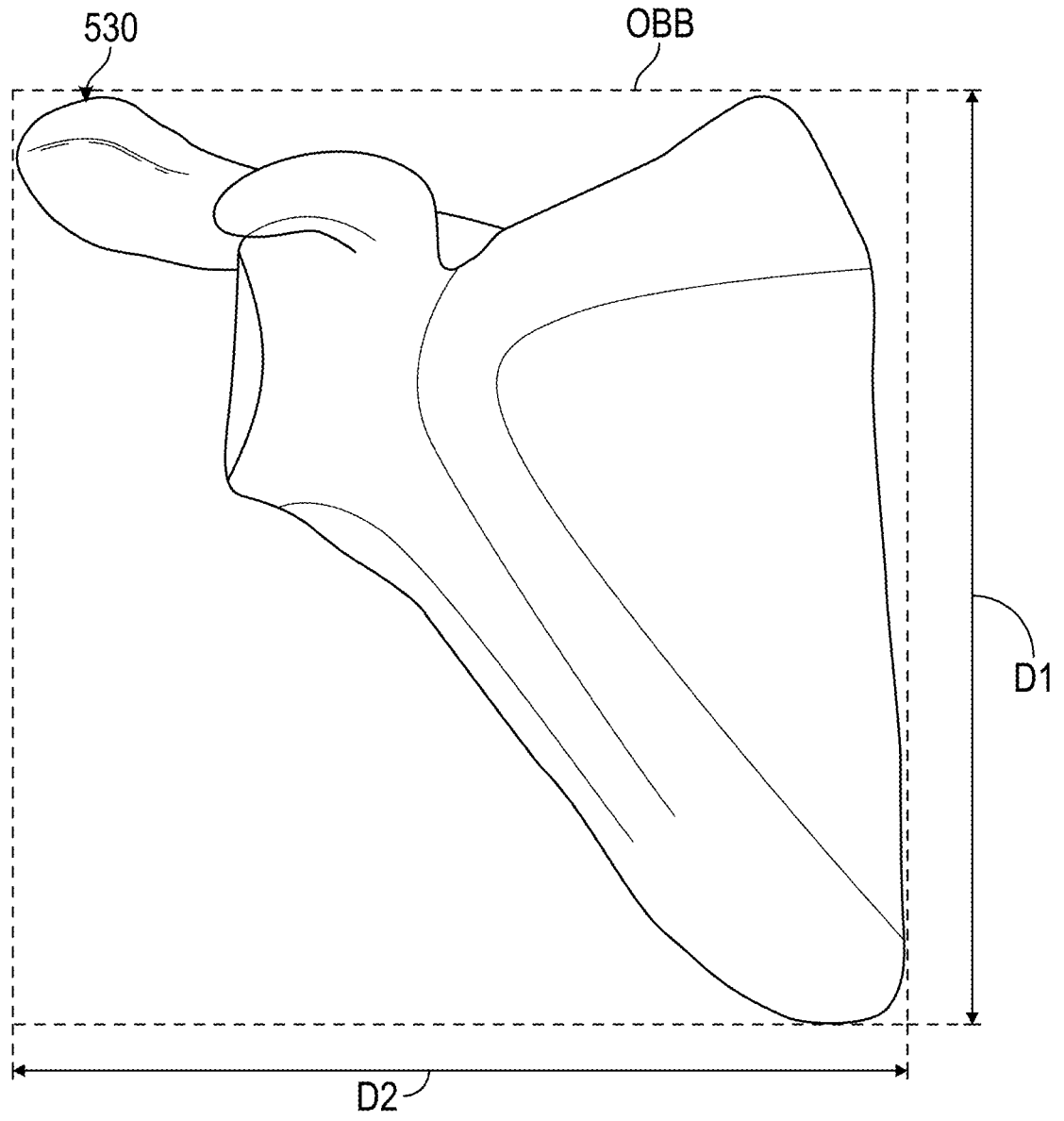
FIGS. 40-45 disclose a shoulder model of a patient.

Referring to FIG. 40, with continuing reference to FIGS. 2 and 39, method 582 may include accessing one or more three-dimensional bone models 530 from memory, such as the database 38 and/or storage device 18. The bone model 530 may be associated with a real or hypothetical patient, including a patient of a representative patient population.

Method 582 may include receiving image data associated with a patient that may omit portion(s) of bone(s) of the patient. The planning environment 28 may be configured to receive image data associated with the patient that may omit the portion(s) of the bone(s). Portions may be omitted due to an acquisition field of view of the associated imaging device 16, trauma to the bone, etc.

Referring to FIGS. 41 and 45, with continuing reference to FIGS. 2 and 39, the bone models 530 may include a first bone model 530S-1 associated with a first bone of the patient. The bone models 530 may include a second bone model 530H-1 associated with a second bone of the patient (see, e.g., FIG. 45). The first and second bones may be adjoining or non-adjoining bones, including any of the bones disclosed herein, such as the scapula and humerus. In the implementation of FIG. 41, the bone model 530 may be a first (e.g., scapula) bone model 530S-1 associated with a scapula of the patient. In other implementations, the bone model 530 may be a second (e.g., humerus) bone model 530H-1 associated with a humerus of the patient (e.g., FIG. 45). The humerus bone model 530H-1 may be a partial three-dimensional bone model associated with a portion of a humerus of the patient, such as a proximal (or distal) humerus.

Method 582 may include generating the partial humerus bone model 530H-1 based on image data that may omit portion(s) of the respective bone of the patient. The spatial module 50 may be configured to generate the partial bone model 530H-1 based on the image data. The comparison module 52 may be configured to select the scapula bone model 530S-1 and/or the partial humerus bone model 530H-1 associated with the first and second bones of the patient.

Referring to FIGS. 41 and 44-45, with continuing reference to FIGS. 2 and 39, the planning environment 28 may be configured to compare the bone models 530S-1, 530H-1 to one or more bone models 30 associated with other patient(s), including patients of a representative patient population. The bone models 530 may include a first representative three-dimensional bone model 530S-2 and/or a second representative three-dimensional bone model 530H-2 associated with another patient. The bone model 530S-2 may be associated with the scapula. The bone model 530H-2 may be associated with the humerus. The partial bone model 530H-1 of the patient may be representative of a lesser portion of the second bone than the representative bone model 530H-2 of the other patient.

At step 582A, one or more bone models 530 of the patient anatomy may be registered or otherwise aligned to a global reference system, including the bone models 530S-1, 530H-1 of the patient and/or the representative bone models 530S-2, 530H-2. The global reference system may be defined at step 582A-1. The global reference system may be defined and the bone model(s) 530 may be aligned to the global reference system utilizing any of the techniques disclosed herein.

Referring to FIG. 42, with continuing reference to FIGS. 2, 4, 39 and 41, at step 582B a representative bone model 530S-2 may be selected from a set of bone models 30 associated with a first bone of the anatomy. The set of bone models 30 may be associated with the first bone of the representative patient population, such as a scapula. The comparison module 52 may be configured to select the representative bone model 530S-2 from a set of bone models 30 associated with the first bone of the anatomy. Various techniques may be utilized to make one or more (e.g., initial or refined) selections of the representative bone model(s) 530S-2 from the set of the bone models 30. Method 582 may include analyzing the representative patient population within a statistical shape model 75. In implementations, the statistical shape modeler 72 may be configured to analyze the representative patient population within the statistical shape model 75 associated with the respective bone(s) utilizing any of the techniques disclosed herein.

In implementations, step 582B may include selecting the (e.g., initial) representative bone model 530S-2 associated with the SSM 75. The SSM 75 may be associated with the scapula and/or humerus. Step 582B may include selecting the representative bone model 530S-2 from a set of the bone models 30 associated with a respective bone of the representative patient population, such as the scapula. The representative scapula model 530S-2 may be associated with another patient or may be representative of a hypothetical anatomy. The representative scapula model 530S-2 may be selected based on various parameters, such as a relative size between the patient and representative scapula models 530S-1, 530S-2.

Referring to FIGS. 42-43, with continuing reference to FIGS. 2, 4 and 39, the statistical shape modeler 72 and/or another portion of the planning system 10 may be configured to vary one or more predefined modes of variation 76 to minimize or otherwise reduce a volume deviation between the patient scapula model 530S-1 and the selected representative scapula model 530S-2. The statistical shape modeler 72 may be configured to select the representative scapula model 530S-2 in response to varying one or more of the predefined modes 76. The predefined modes 76 may include a first mode of variation 76 (e.g., mode $76_1$ of FIG. 5). The first mode of variation 76 may be associated with a size of the respective bone(s). In implementations, the statistical shape modeler 72 may be configured to vary the first mode of variation 76 to a select a representative scapula model 530S-2 that may be substantially equal to or may otherwise approach a geometry (e.g., size) of the scapula model 530S-1 of the patient. In implementations, step 582B may include varying one or more of the modes 76, such as the first mode, to minimize or otherwise reduce the volume deviation between the patient scapula model 530S-1 and a representative scapula model 530S-2 selected from the set of bone models 30 associated with the SSM 75 at step 582B-1. The statistical shape modeler 72 may be configured to iteratively select bone models 30/530S-2 from the set of bone models 30 and determine the respective volume deviations.

The statistical shape modeler 72 and/or spatial module 50 may be configured to determine the volume deviation between the patient scapula model 530S-1 and each selected representative scapula model 530S-2 within a set of bone models 30 associated with the scapula SSM 75. The statistical shape modeler 72 and/or comparison module 52 may be configured to select the representative scapula model 530S-2 from the set of bone models 30 based on the determined volume deviations.

Various techniques may be utilized to determine a minimum volume deviation between the bone model 530 of the patient and a set of the bone models 30 associated with the SSM 75 of the respective bone. In implementations, the statistical shape modeler 72 may be configured to evaluate one or more of the bone models 30 relative to the patient bone model 530S-1 in response to changing the first mode of variation 76 across a range of predefined standard deviations 78 associated with the first mode 76 (e.g., −3.0 to 3.0 standard deviations). For each value of the first mode 76, the spatial module 50 may be configured to determine a deviation between one or more dimensions of respective oriented bounding boxes (OBB) (shown in dashed lines in FIG. 40) of the patient bone model 530S-1 and a selected one of the representative bone models 530S-2 (e.g., FIG. 42). The OBB may have a two-dimensional or three-dimensional geometry. The comparison module 52 may be configured to select the representative bone model 530S-2 from the set of bone models 30 associated with a standard deviation 78 value that may minimize or otherwise reduce a difference between the OBB dimension(s), including a first dimension D1 (e.g., maximum length) and/or a second dimension D2 (e.g., maximum width), of the bone model 530S-1, 530S-2. In implementations, the maximum length may be established in a superior/inferior direction of the anatomy. In implementations, the comparison module 52 may be configured to identify a subset of the bone models 30 having a deviation below a predefined threshold, which may be utilized for subsequent selection(s) and/or adjustment(s) based on one or more predefined modes 76 (see, e.g., step 582D-1).

Referring to FIG. 42, with continuing reference to 2 and 39, at step 582C the representative (e.g., second) bone model 530S-2 may be registered to, or otherwise substantially aligned with or fit to, the patient (e.g., first) bone model 530S-1 to establish a registered state of the representative bone model 530S-2. The spatial module 50 may be configured to at least partially register the representative bone model 530S-2 to the patient bone model 530S-1 to establish the registered state (e.g., position) of the representative bone model 530S-2. The spatial module 50 may be configured to register the selected representative bone model 530S-2 to the patient bone model 530S-1 utilizing any of the techniques disclosed herein.

Various techniques may be utilized to register or otherwise adjust a position of the representative bone model 530S-2 relative to the patient bone model 530S-1. Referring to FIG. 41, with continuing reference to FIGS. 2 and 39, step 582C may include aligning one or anatomical points (e.g., landmarks) PL common between the patient and representative bone models 530S-1, 530S-2 at step 582C-1. The anatomical points PL may include any of the anatomical points disclosed herein (see, e.g., points P1-P3 of FIG. 29). The anatomical points PL may include a set of points, such as points P1, P2 and P4. The first point P1 may be established at a center of the glenoid fossa. The second point P2 may be established at a trigonum scapulae. The point P4 may be established at a superior angle of the scapula.

Referring to FIG. 42, with continuing reference to FIGS. 2, 39 and 41, at step 582C-2 a position and/or orientation of the representative bone model 530S-1 may be adjusted based on a fit between the volumes of the patient and representative bone models 530S-1, 530S-2 to establish the registered state (e.g. position) of the representative bone model 530S-2. The spatial module 50 may be configured to fit the volumes of the scapula bone model 530S-1 of the patient and the selected representative bone model 530S-2 to each other. The spatial module 50 may be configured to determine a transformation that establishes a best fit mapping between the defined anatomical points PL (FIG. 41). The best fit mapping may be established utilizing a least squares techniques. The spatial module 50 may be configured to apply an iterative closest point (ICP) technique to approach the shapes and/or fit the volumes of the bone models 530S-1, 530S-2 relative to each other.

Referring to FIG. 43, with continuing reference to FIGS. 2, 39 and 41-42, a registered state (e.g., position) of the representative bone model 530S-2 may be refined (e.g., minimized) to improve a fit between the patient bone model 530S-1 and representative bone model 530S-2. A step 582D, a subsequent (e.g., refined) selection and/or positional adjustment of a representative bone model 530S-2 from a set of the bone models 30 may be performed. The representative bone model 530S-2 selected and/or positionally adjusted at step 582D may be the same or may differ from the representative bone model 530S-2 previously selected from the set of bone models 30 at step 582B.

Various techniques may be utilized to make subsequent selection(s) and/or positional adjustments. Step 582D may include varying one or more other modes of variation 76 associated with the SSM 75 at step 582D-1, including any of the modes 76 disclosed herein. In implementations, the first mode 76 of the SSM 75 may be associated with a position of the anatomy. The remaining modes 76 of the SSM 75 may be associated with a shape of the shape of the anatomy and may be constrained to a (e.g., registered) position of the anatomy associated with the first mode 76. In implementations, the statistical shape modeler 72 may be configured to vary the first (e.g., eight) modes of variation 76 of the SSM 75. It should be understood that fewer or more than eight modes of variation 76 may be utilized. Varying fewer of the modes of variation 76 of the SSM 75 may decrease computation time, whereas varying more of the modes of variation 76 may improve accuracy. In implementations, the first eight modes of variation 76 may be associated with approximately 85 percent of variation of the SSM 75. An order of the modes 76 may be associated with a relative amount of variation of the SSM 75 (e.g., first mode being the greatest amount of variation, and last mode being the least amount of variation). The modes of variation 76 associated with the first bone (e.g., scapula) may be the same modes of variation 76 associated with the second bone (e.g., humerus). The statistical shape modeler 72 may be configured to vary the same number or a different number of modes 76 for the associated bones of the anatomy. The statistical shape modeler 72 may be configured to limit the subsequent selection to a subset of the bone models 30 based on a limited range of standard deviations 78 (e.g., within ±1 SD) from the respective mode value(s) of the previously selected representative bone model 530S-2. The statistical shape modeler 72 may utilize various techniques to evaluate the modes 76, such as a Simplex Nelder-Mead Optimization (e.g., Amoeba Search) technique. In implementations, step 582D-1 may include varying only mode(s) of variation 76 associated with a position and/or orientation of the representative bone model 530S-2 previously selected at step 582B, including any of the modes of variation disclosed herein.

The comparison module 52 may be configured to select a representative bone model 530S-2 from the set (or subset) of bone models 30 in response to determining a (e.g., minimum) volume deviation within a set of volume deviations. The set of volume deviations may be established between the scapula bone model 530S-1 of the patient and each respective representative bone model 530S-2 selected from the set of the bone models 30 in response to the statistical shape modeler 72 varying one or more of the predefined modes 76 of the SSM 75.

Referring to FIG. 44, with continuing reference to FIGS. 2, 39 and 41-43, at step 582E a second (e.g., initial) representative bone model 530H-2 associated with the second bone may be selected or otherwise identified. The selected representative bone models 530S-2, 530H-2 may be associated with the same anatomical model 529-2 and/or the same patient. Step 582E may include accessing a plurality of three-dimensional bone models 30 associated with one or more bones and/or one or more joints of a representative patient population. Step 582E may include selecting the representative bone model 530H-2 from a set of representative bone models 30 associated with a respective bone of the representative patient population, such as the humerus. The comparison module 52 may be configured to select the representative bone model 530H-2 from the set of representative bone models 30.

The comparison module 52 may be configured to select the representative bone model 530H-2 based on the selected representative model 530S-2 associated with the first bone. The selected representative bone model 530H-2 may include the omitted portion(s) of the second bone. The partial bone model 530H-1 of the patient may omit a distal portion of the humerus. The representative bone model 539H-2 may include the distal portion of the humerus.

The comparison module 52 may be configured to select or otherwise identify the representative bone model 530H-2 from a set of representative bone models 30 associated with the representative patient population based on the selected representative bone model 530S-2 (e.g., at step 582B and/or 582D), or vice versa. The comparison module 52 may be configured to select the representative bone model 530H-2 from the set of bone models 30 in response to establishing the registered state (e.g., position) of the selected representative bone model 530S-2.

Step 582E may include selecting the representative bone model 530H-2 from the set of representative bone models 30 in response to making an (e.g., initial) selection of the representative bone model 530S-2 at step 582B, establishing the registered state of the selected representative bone model 530S-2 at step 582C and/or refining a position and/or selection of the representative bone model 530S-2 from the set of representative bone models 30 at step 582D.

Referring to FIG. 45, with continuing reference to FIGS. 2, 39 and 41-44, at step 582F the partial bone model 530H-1 of the patient may be at least partially aligned (e.g., registered) to the selected representative bone model 530H-2 to establish a registered state (e.g., position) of the patient bone model 530H-1. The partial bone model 530H-1 may be associated with a long bone, such as the humerus. The bone models 530H-1, 530H-2 may include a respective diaphysis portion 530HD associated with a diaphysis of the long bone and/or a head portion 530HH associated with a head of the long bone. The spatial module 50 may be configured to at least partially register or otherwise align the diaphysis portion 530HD-1 of the partial bone model 530H-1 to the diaphysis portion 530HD-2 of the representative bone model 530H-2 to establish the registered state of the partial bone model 530H-1.

Various techniques may be utilized to register the partial bone model 530H-1 of the patient. Step 582F may include aligning one or more landmarks or other points of the partial bone model 530H-1 to the representative bone model 530H-2 at step 582F-1. The landmarks may include a center point 530CP of the head portion 530HH. Step 582F-1 may include substantially aligning the center point 530CP-1 of the head portion 530HH-1 of the partial bone model 530H-1 with the center point 530CP-2 of the head portion 530HH-2 of the representative bone model 530H-2. Step 582F may include rotating the partial bone model 530H-1 of the patient relative to the representative bone model 530H-2 at step 582F-2, which may occur subsequent to step 582F-1. Step 582F-2 may include rotating the head portion 530HH-1 of the partial bone model 530H-1 about the respective center point 530CP to at least partially register the partial bone model 530H-1 to the representative bone model 530H-2. In implementations, the spatial module 50 may be configured to apply an iterative closest point (ICP) technique to approach the shapes and/or fit the volumes of the bone models 530H-1, 530H-2 relative to each other.

A relationship between two or more bones of the anatomy may be utilized to improve an overall fit between the patient and representative bone models 530S-1, 530S-2 and 530H-1, 530H-2. The selected representative bone models 530S-2, 530H-2 may be associated with a respective representative anatomical (e.g., shoulder) model 529-2 of a patient. Registering the selected representative bone models 530S-2, 530H-2 relative to the patient bone models 530S-1, 530H-1 may establish a registered state (e.g. position) of the representative anatomical model 529-2 relative to the patient (e.g., shoulder) anatomical model 529-1. In implementations, the planning environment 28 may be configured to register or otherwise substantially align a representative anatomical model 529-2 with the patient anatomical model 529-1 to improve an overall fit between the patient bone models 530S-1, 530-2 and the respective representative bone models 530S-2, 530H-2.

At step 582G, a subsequent (e.g., refined) selection and/or positional adjustment of the representative anatomical model 529-2 and associated representative bone models 530S-2, 530H-2 may be performed to improve an overall fit between the patient and representative anatomical models 529-1, 529-2. The representative anatomical model 529-2 selected at step 582G may be the same or may differ from the representative anatomical model 529-2 associated with the representative bone models 530S-2, 530H-2 previously selected at steps 582B, 582D and/or 582E.

Various techniques may be utilized to select and/or adjust a position of the representative anatomical model 529-2. An anatomical SSM 75 may be established for an anatomical group of two or more adjoining and/or non-adjoining bones of the anatomy. In implementations, an anatomical SSM 75 may be established for a shoulder including a scapula and humerus. One or more modes of variation 76 and associated standard deviations 78 may be established for the anatomical SSM 75. The modes of variation 76 and/or standard deviations 78 may be the same or may differ from the modes of variation 76 and/or standard deviations 78 of the individual bones associated with the anatomical group of bones. The statistical shape modeler 72 may be configured to assign an AMC 80 to one or more anatomical models 29 according to the anatomical SSM 75.

At step 582G-1, the representative anatomical model 529-2 may be selected and/or positionally adjusted in response to varying one or more of the predefined modes 76 within the statistical shape model 72 associated with the anatomical SSM 75. The statistical shape modeler 72 may be configured to fit the bone models 530S-2, 530H-2 of the representative anatomical model 529-2 together (e.g., simultaneously) with the bone models 530S-1, 530H-1 of the patient anatomical model 529-1. The statistical shape modeler 72 may be configured to positionally adjust and/or select the representative anatomical model 529-2 from a set of the anatomical models 29 in response to varying one or more of the predefined modes 76 associated with the anatomical SSM 75. The comparison module 52 may be configured to select the anatomical model 529-2 from a set of the anatomical models 29 in response to determining a (e.g., minimum) volume deviation within a set of volume deviations between the aligned patient bone models 530S-1, 530H-1 of the associated anatomical model 529-1 and one or more respective anatomical models 529-2 within the set of anatomical models 29. The set of volume deviations may be established between the patient anatomical model 529-1 and each respective representative anatomical model 529-2 of the set of the anatomical models 29 in response to the statistical shape modeler 72 varying one or more of the predefined modes 76 of the anatomical SSM 75.

In implementations, the statistical shape modeler 72 may be configured to vary the modes of variation 76 and associated standard deviations 78 to make iterative positional adjustments of a previously selected anatomical model 529-2 and/or selections of the representative anatomical models 529-2 within the set of anatomical models 29. The statistical shape modeler 72 may be configured to compute respective distances between surfaces of the patient anatomical model 529-1 and surfaces of the representative anatomical model 529-2. The comparison module 52 and/or statistical shape modeler 72 may determine values (e.g., standard deviations) of the modes 76 that may minimize or otherwise reduce the distances between the surfaces of the bone models 530S-2, 530H-2 of the selected representative anatomical model 529-2 and the surfaces of the bone models 530S-1, 530H-1 of the patient anatomical model 529-1.

The bone associated with the partial bone model 530H-1 of the patient may be analyzed based on the registered state (e.g., position) of the representative bone model 530H-2. At step 582H, one or more posture parameters associated with a posture of the patient may be determined based on the registered state of the representative bone model 530H-2. The planning environment 28 may be configured to establish an implant plan in response to establishing the registered state of the representative bone model 530H-2 in relation to the partial bone model 530H-1 of the patient. The implant plan may be established utilizing any of the techniques disclosed herein. The implant plan may be established based on the determined posture parameter(s). Method 582 may include establishing an implant plan based on the registered state of the partial bone model 530H-2.

Figures 46A, 46B, 47A, 47B:
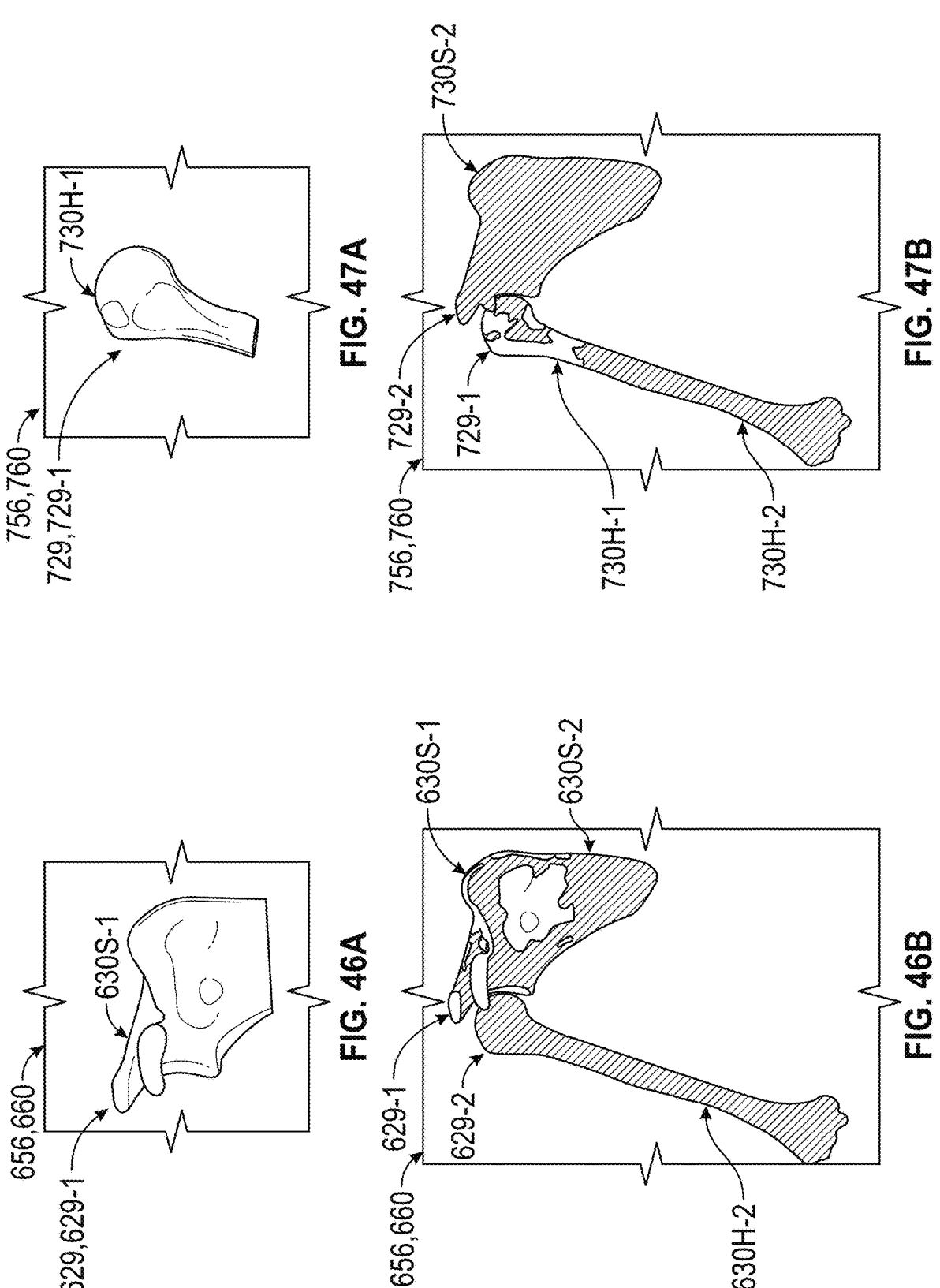
FIGS. 46A-46B disclose an anatomical model associated with a scapula of a patient.
FIGS. 47A-47B disclose an anatomical model associated with a humerus of a patient.

A geometry and/or orientation of other omitted portions of the anatomy may be predicted or otherwise determined. In the implementation of FIGS. 46A-46B, the planning system 10 may acquire localized image data associated with one or more bones of the anatomy, such as a portion of a scapula associated with a scapula bone model 630S-1. The scapula bone model 630S-1 may be associated with a patient anatomical model 629-1. A portion of the scapula may be omitted from the image data, such as a distal portion of the scapula including the inferior angle. A humerus of the patient may also be omitted from the image data. Utilizing the techniques disclosed herein, including method 582, a representative anatomical model 629-2 including an associated scapula bone model 630S-2 and humerus bone model 630H-2 may be selected to predict or otherwise determine the omitted portion of the scapula and the associated humerus.

In the implantation of FIGS. 47A-47B, the planning system 10 may acquire localized image data associated with a portion of a humerus associated with a humerus bone model 730H-1. The humerus bone model 730S-1 may be associated with a patient anatomical model 729-1. A portion of the humerus may be omitted from the image data, such as a distal portion of the humerus. A scapula of the patient may also be omitted from the image data. Utilizing the techniques disclosed herein, including method 582, a representative anatomical model 729-2 including an associated scapula bone model 730S-2 and humerus bone model 730H-2 may be selected to predict or otherwise determine the omitted portion of the humerus and the associated scapula.

Figure 48A:
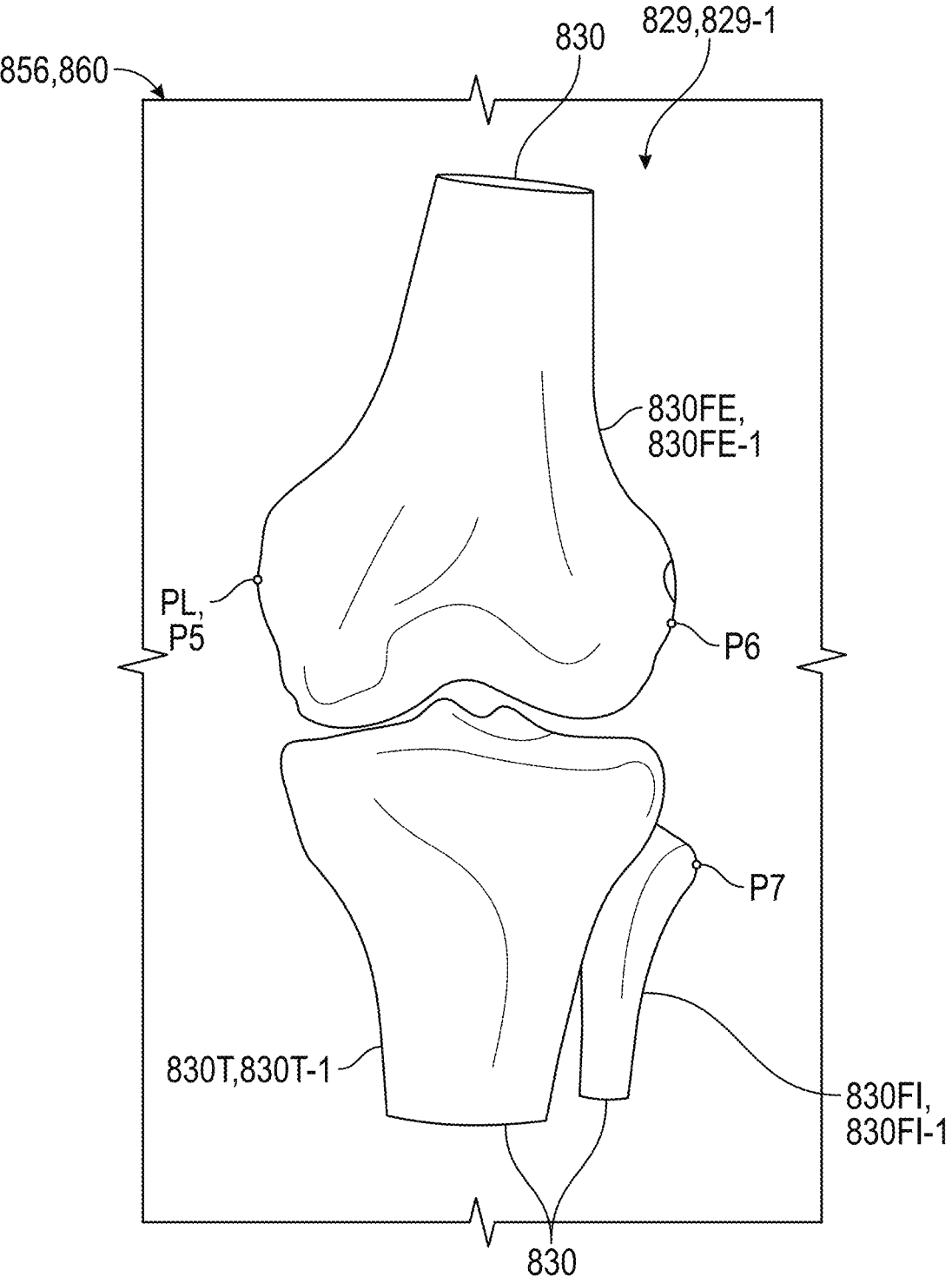

Referring to FIGS. 48A-48C, with continuing reference to FIG. 2, the techniques disclosed herein, including any of the steps of method 582, may be utilized to determine one or more axes and/or other aspects associated with the anatomy of a patient. The axes may be associated with a respective bone, joint and/or limb of the anatomy, including any disclosed herein such as shoulder, ankle, hip, knee and elbow joints and/or associated bones. In the implementation of FIG. 48A, the planning system 10 may acquire localized image data associated with one or more bones of the anatomy. The localized image data may omit portions of the anatomy, which may reduce acquisition cost and radiation exposure to the patient.

The planning system 10 may establish an anatomical model 829 including one or more bone models 830. In the implementation of FIG. 48A, the anatomical model 829 may be associated with a knee joint. The bone models 830 may include a first (e.g., femur) bone model 830FE, a second (e.g., tibia) bone model 830T and/or a third (e.g., fibula) bone model 830FI. The image data may include a localized portion of the anatomy, such as portions of the limb adjacent to the knee joint. One or more portions of the anatomy omitted from the image data, such as a proximal portion of the femur associated with the femur bone model 830FE, a distal portion of the tibia associated with the tibia bone model 830T and/or a distal portion of the fibula associated with the fibula bone model 830FI.

Referring to FIG. 48B, with continuing reference to FIGS. 2, 4 and 48A, the anatomical model 829 may be a first anatomical model 829-1 associated with the patient. A representative anatomical model 829-2 associated with the anatomy may be selected or otherwise identified. The representative anatomical model 829-2 and associated bone models 830 may include the portion(s) of the bones omitted from the first anatomical model 829-1. The representative anatomical model 829-2 may be selected or otherwise identified from a set of representative anatomical models 29 (FIG. 2) utilizing any of the techniques disclosed herein. The planning system 10 may be configured to select the representative anatomical model 829-2 from the set of representative anatomical models 29 associated with respective bone(s) of the representative patient population, such as the femur, tibia and/or fibula. In implementations, the planning system 10 may be configured to select the representative anatomical model 829-2 utilizing any of the techniques disclosed herein including the statistical shape modeler 72. The representative anatomical models 29 may be associated with a statistical shape model (SSM) 75 (FIG. 4).

The planning system 10 may be configured to register or otherwise substantially align the anatomical models 829-1, 829-2 and/or associated bone models 830 with each other utilizing any of the techniques disclosed herein. In the implementation of FIG. 48A, one or more anatomical points (e.g., landmarks) PL may be identified. The anatomical points PL may include a set of points, such as points P5-P7. The anatomical points PL may be identified utilizing any of the techniques disclosed herein, including manually in response to user interaction with the user interface 856 and/or automatically by the planning system 10. The planning system 10 may be configured to substantially align the anatomical points PL that may be common between the bone models 830 of the patient and representative anatomical models 829-1, 829-2 with each other to establish a registered state (e.g. position) of the representative anatomical model 829-2. The planning system 10 may be configured to minimize a distance between the respective pairs of anatomical points PL. One or more predefined modes of variation 76 of the statistical shape model 75 associated with the anatomy may be varied to fit or otherwise approach a shape of the anatomy.

The representative anatomical model 829-2 in the registered state may be utilized to determine one or more aspects of the patient anatomy. The bone models 830 associated with the representative anatomical model 829-2 may be utilized to predict or otherwise determine a geometry and/or orientation of the portions of the bones omitted from the patient anatomical model 829-1 in the registered state. Relative positions and/or distance(s) between landmarks associated with the omitted portions of the anatomy may be determined. In implementations associated with a knee joint, the representative anatomical model 829-2 may be utilized to determine extension and/or rotation. In implementations associated with an ankle joint, the representative anatomical model including the omitted portion(s) of the respective bone(s) may be utilized to determine internal/external rotation and/or varus/valgus of the bone(s).

Referring to FIG. 48C, with continuing reference to FIGS. 2 and 48A-48B, the planning system 10 may be configured to determine one or more axes associated with the respective bone(s) of the anatomy associated with the anatomical model 829, such as an anatomical and/or mechanical axis of the respective bone or limb, based on the registered position of the bone model(s) 330 of the representative anatomical model 829-2. The axes may include a mechanical axis A1, an anatomical axis A2 and/or an anatomical axis A3. The anatomical axis A2 may be associated with an anatomical axis of the femur. The anatomical axis A3 may be associated with an anatomical axis of the tibia. The mechanical axis A1 may be a mechanical axis of the limb (e.g., leg), which may be established between the proximal femur and distal tibia. The mechanical axis A1 may be utilized to determine one or more corrections to restore the mechanical axis of the bone and/or limb and/or a position and/or orientation of implant(s), including in a knee arthroplasty or a high tibial osteotomy (HTO) procedure.

Figures 49A, 49B:
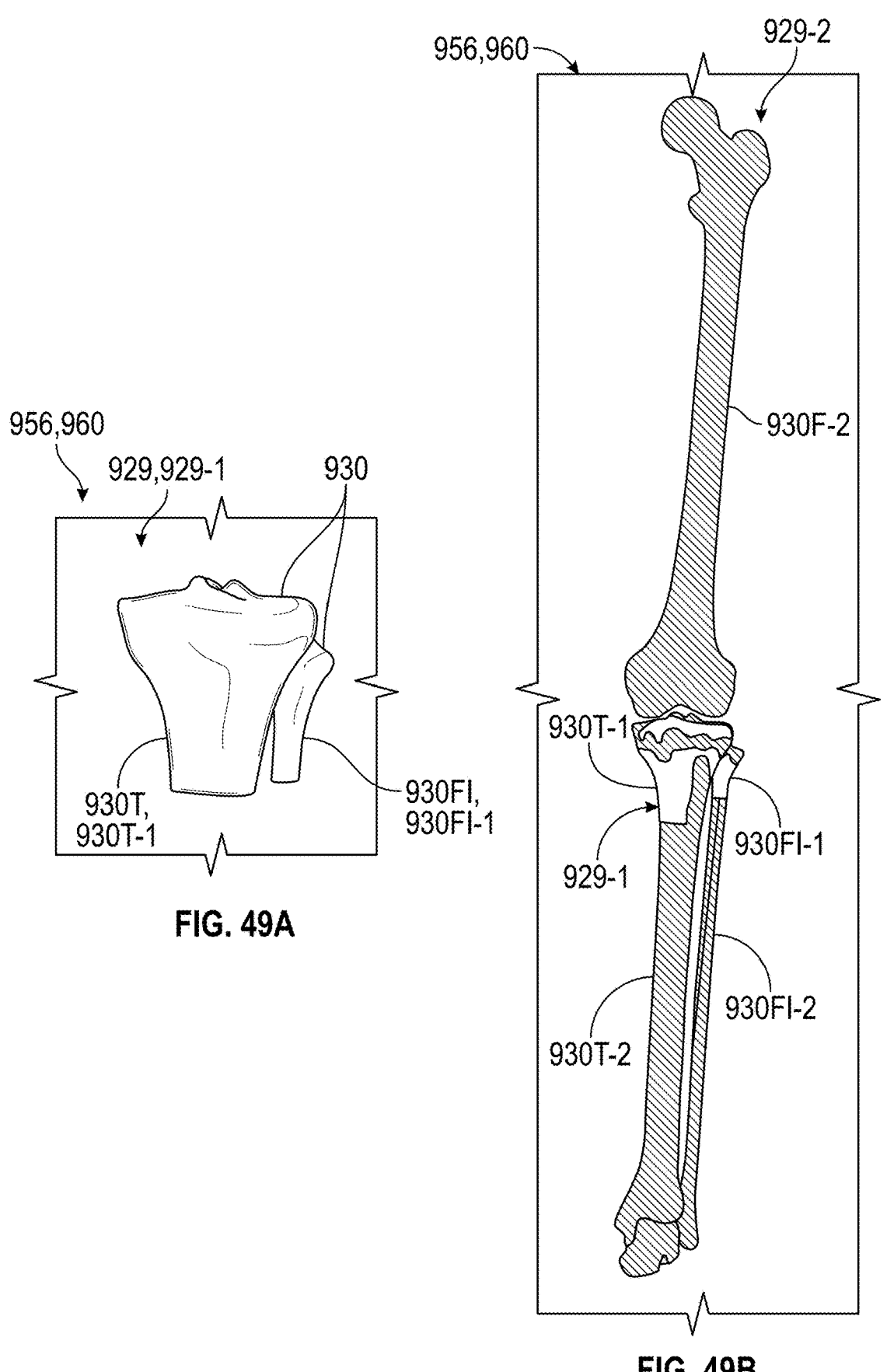
FIGS. 49A-49B disclose another anatomical model associated with a knee joint of a patient.
Figures 50A, 50B:
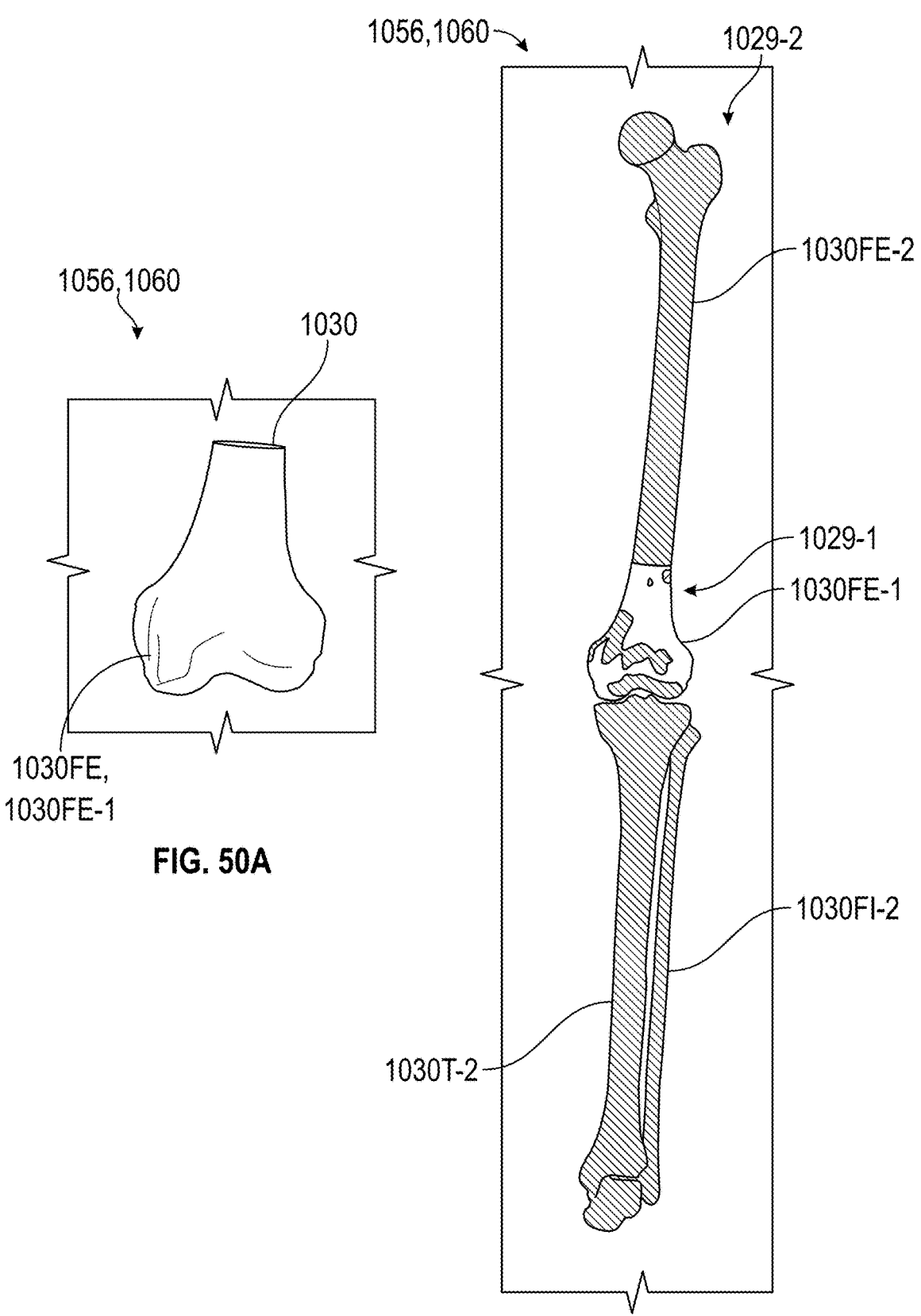
FIGS. 50A-50B disclose yet another anatomical model associated with a knee joint of a patient.

In the implementation of FIGS. 49A-49B, the image data may omit the femur and portions of the tibia and fibula. The representative anatomical model 929-2 may include a femur bone model 930F-2 associated with a femur, a tibia bone model 930T-2 associated with a tibia, and a fibula bone model 930FI-2 associated with a fibula. The representative anatomical model 929-2 may include the omitted portions of the bone(s) of the patient anatomical model 929-1. In the implementation of FIGS. 50A-50B, the image data may omit the tibia and fibula and portions of the femur. The representative anatomical model 1029-2 may include a femur bone model 1030FE-2 associated with a femur, a tibia bone model 1030T-2 associated with a tibia, and a fibula bone model 1030FI-2 associated with a fibula. The representative anatomical model 1029-2 may include the omitted portions of the bone(s) of the patient anatomical model 1029-1. Aspects of the bone(s) of the patient anatomical models 929-1, 1029-1, including landmarks and axes, may be predicted or otherwise determined utilizing the representative anatomical models 929-2, 1029-2 according to any of the techniques disclosed herein.

Figure 51A:
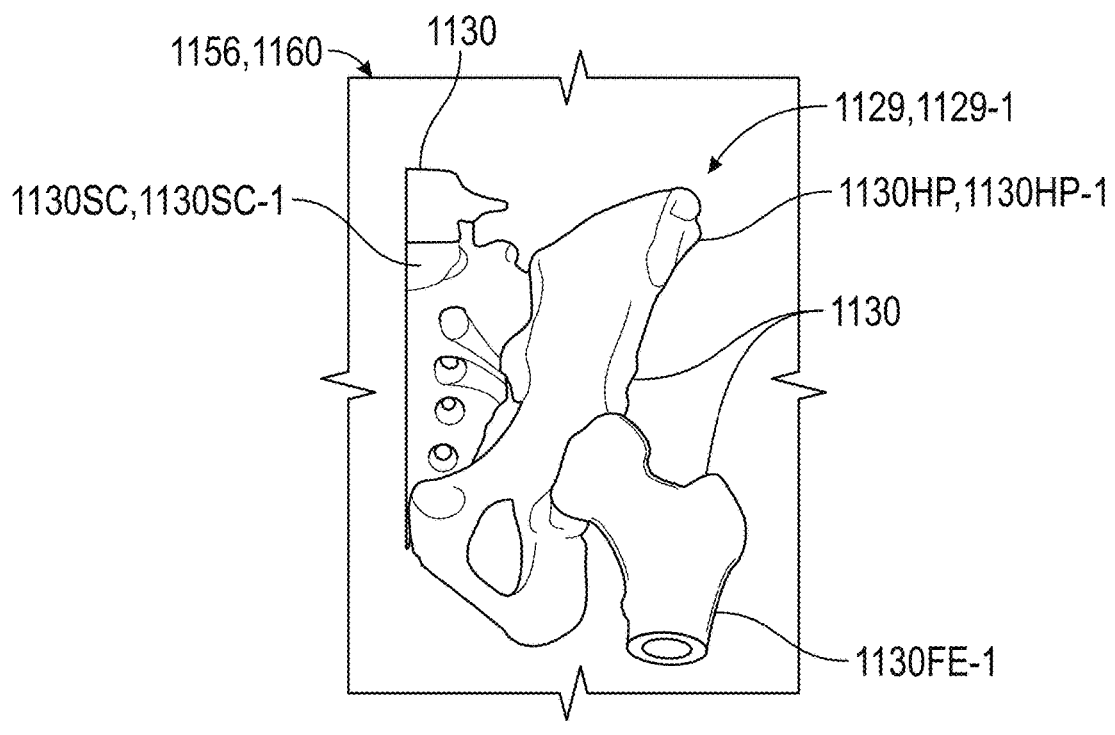
FIGS. 51A-51B disclose an anatomical model associated with a hip joint of a patient.
Figure 51B:
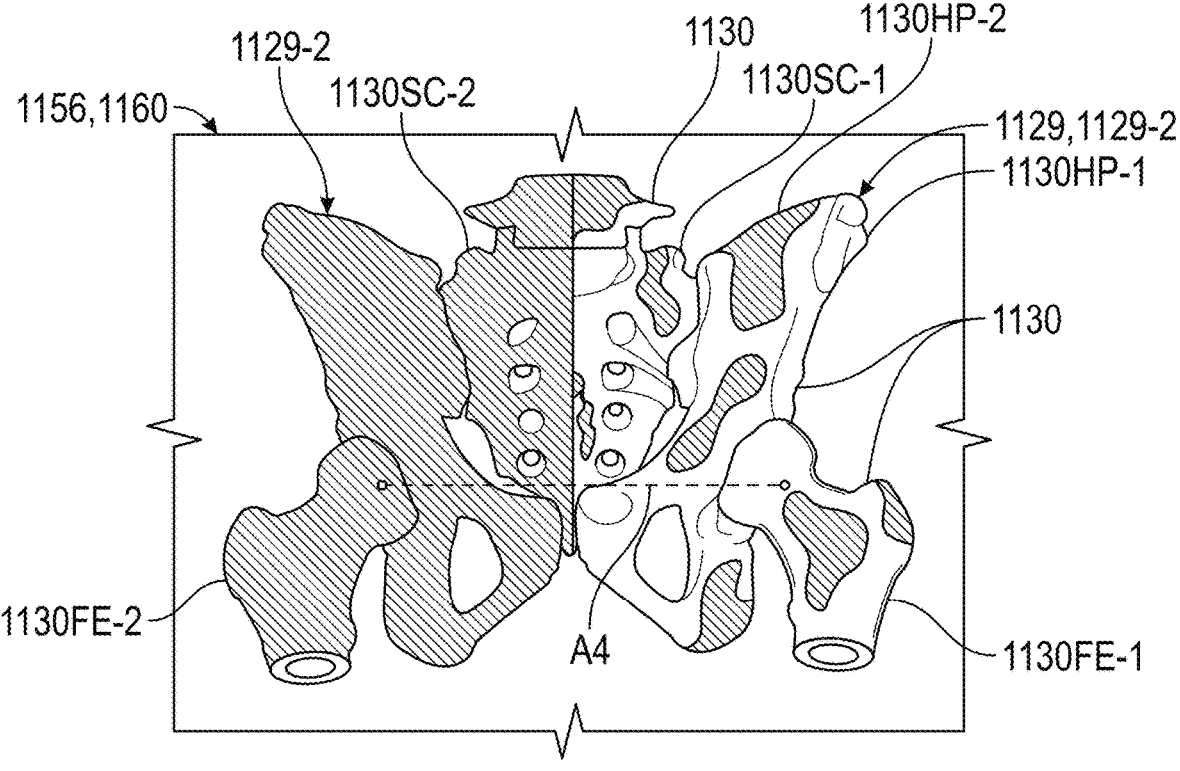

Other joints may benefit from the teachings disclosed herein. FIGS. 51A-51B disclose an anatomical model 1129 associated with a hip joint. The anatomical model 1129 may be associated with one or more bones of the pelvis. In implementations, the anatomical model 1129 may include at least one hipbone model 1130HP associated with a respective hipbone, a sacrum bone model 1130SC associated with a sacrum, and femur bone model 1130FE associated with a femur. The representative anatomical model 1129-2 may include the omitted portions of the bone(s) of the patient anatomical model 1129-1.

The representative anatomical model 1129-2 may be utilized to predict or otherwise determine one or more landmarks and/or axes associated with aspects of the anatomy omitted from the image data of the patient. In implementations, an (e.g., horizontal) axis A4 may be determined based on the predicted geometry and position of the omitted femur bone of the patient.

Other techniques may be utilized to determine an acquisition orientation of various bones of the patient. In implementations, the imaging device(s) 16 (FIG. 2) may obtain one or more two-dimensional images 26 of the patient anatomy. The images 26 may be at different (e.g., perpendicular) orientations relative to each other. The system 10 may be configured to determine the acquisition orientation based on comparing a three-dimensional anatomical model 29 to a profile of the patient anatomy in the two-dimensional images 26. The anatomical model 29 may be associated with another patient than the patient associated with the two-dimensional images 26.

Figure 52:
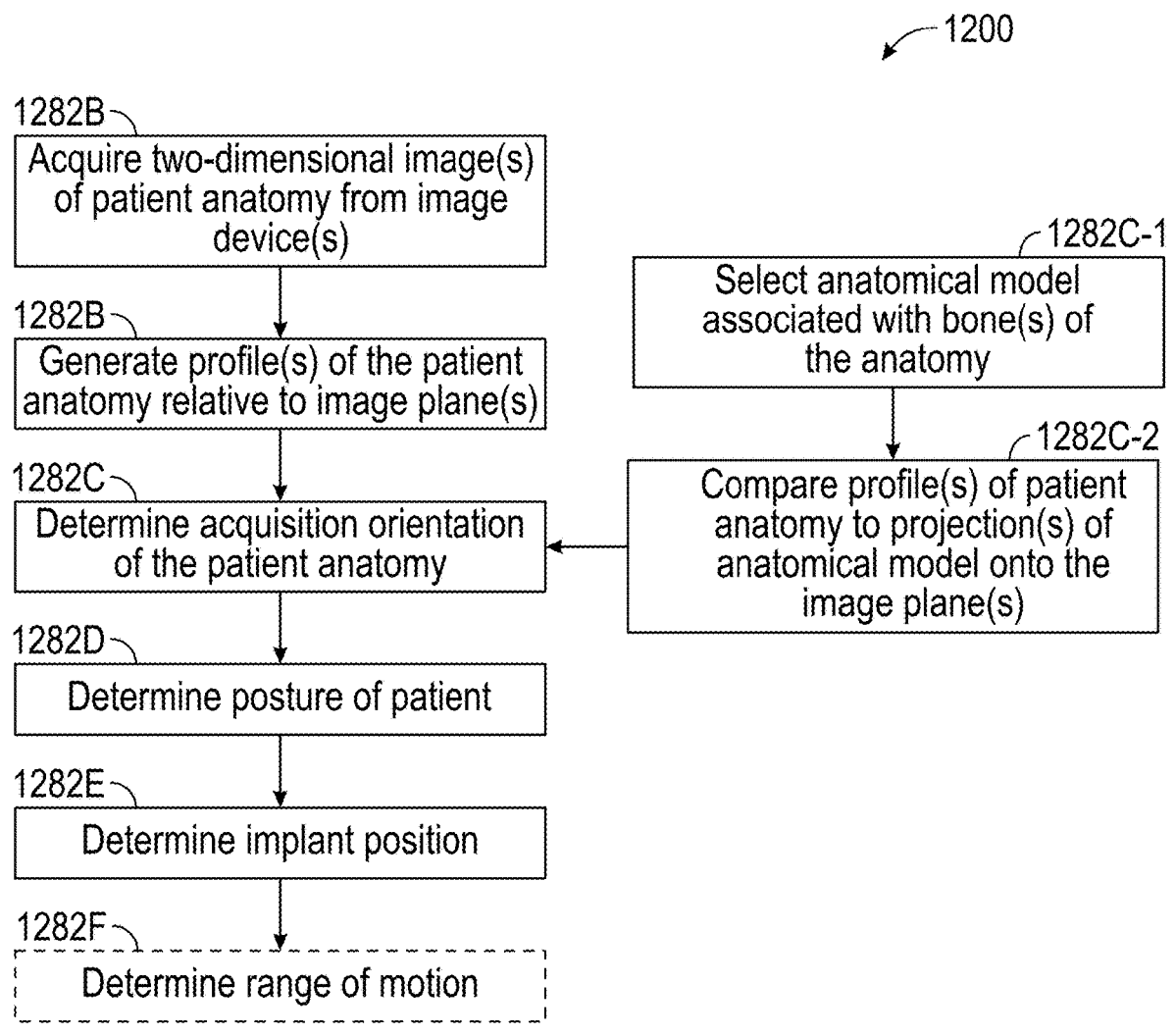
FIG. 52 discloses yet another method for planning a surgical procedure on a respective patient using a surgical planning system.

FIG. 52 discloses a method in a flowchart 1282 for a surgical procedure. The method 1282 may be utilized to pre-operatively plan, implement, evaluate and/or validate aspects of various surgical procedures, such as an arthroplasty for restoring functionality to shoulders, ankles, knees, hips and other joints. The method 1282 may be utilized with any of the planning systems and methods, virtual anatomical models and/or bone models disclosed herein, such as the planning system 10. The method 1282 may be utilized to determine a position and/or orientation of one or more implants based on an acquisition orientation of the anatomy of a patient, such as a scapula and humerus. The orientation of the anatomy may be associated with a posture of a patient. Fewer or additional steps than are recited below could be performed within the scope of this disclosure, and the recited order of steps is not intended to limit this disclosure. The method 682 may incorporate any of the steps of method 382, 482 and/or 582 disclosed herein, and vice versa. Reference is made to the system 10.

Referring to FIGS. 2 and 4, with continuing reference to FIG. 52, various techniques may be utilized to determine one or more characteristics of the patient, such as posture, based on a shoulder SSM 75. A 2D profile of the patient anatomy may be captured in each of the X-ray images. The scapula SSM 75 may be utilized to select a bone model 30 associated with the anatomical makeup classification database 70 that may be the closest to the anatomy captured in the X-ray images. Bone models 30 of the scapula and humerus may be selected by projecting a silhouette of the 3D model onto the 2D plane associated with each of the X-ray images. The scapula SSM 75 may select each bone model 30 having a silhouette that may best fit the 2D profile of the patient anatomy in each of the 2D planes. The scapula SSM 75 may be configured to adjust a camera angle to adjust a projection of the silhouette. The adjusted camera angle associated with the best fit silhouette may be representative of, or may otherwise be associated with, the posture of the patient in an acquisition and/or anatomical position. The adjusted camera angle may be utilized to predict or otherwise determine a relative anatomical position, alignment and/or orientation of adjoining and/or non-adjoining bones of the patient, additionally and/or alternatively to determining a posture of the patient.

Figure 53:
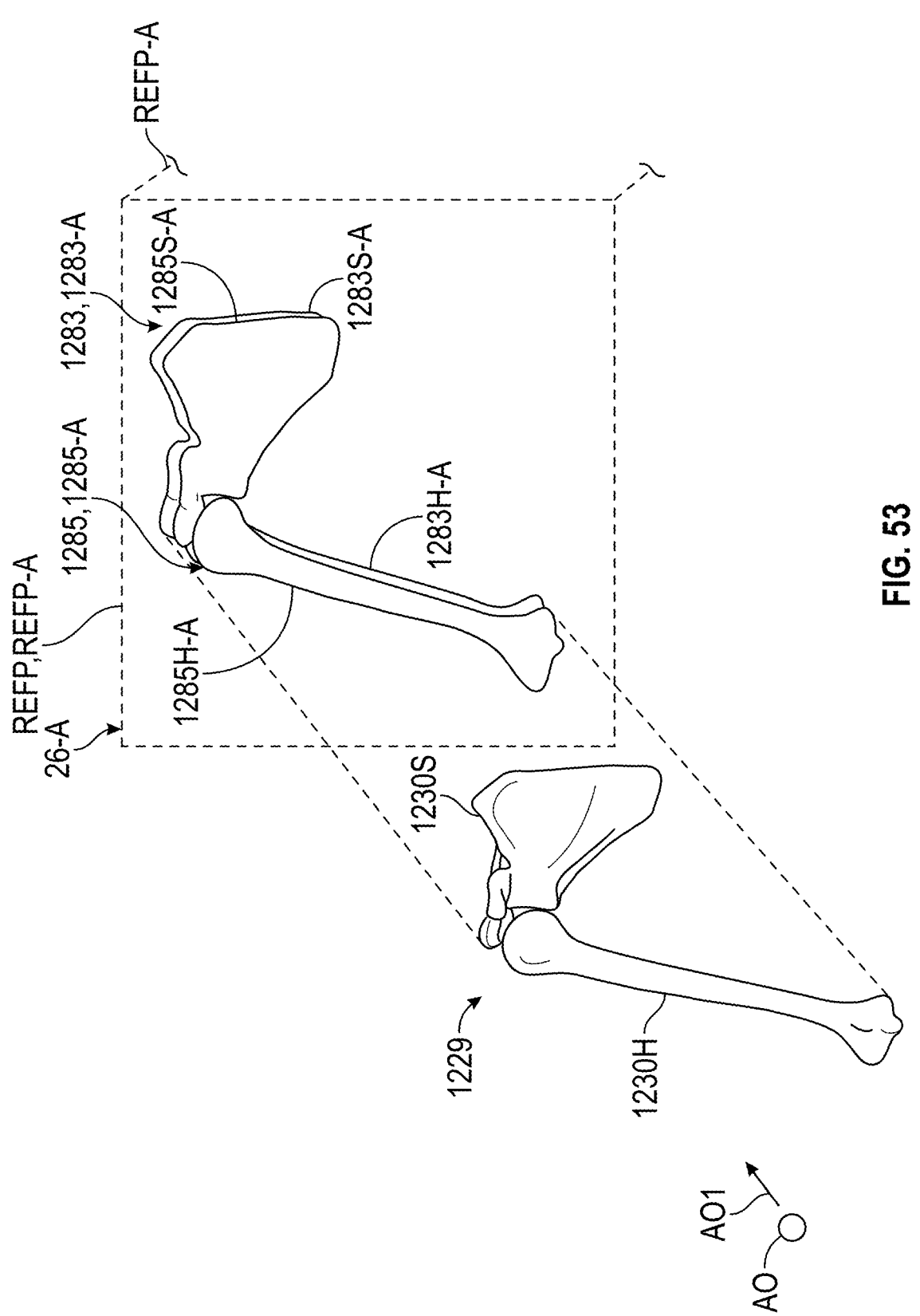
FIGS. 53-54 disclose a shoulder model projected on a profile associated with patient anatomy.
Figure 54:
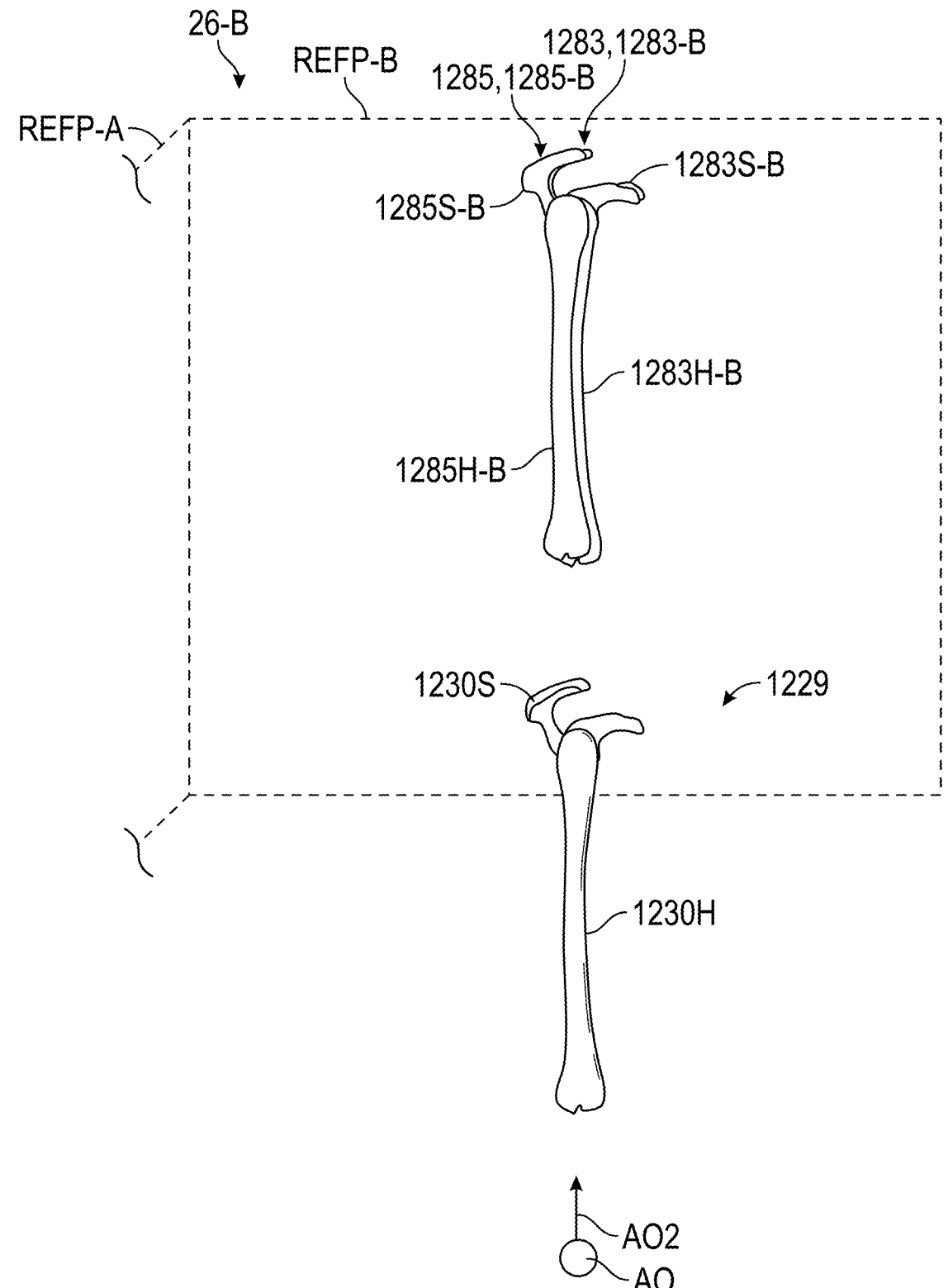

Referring to FIG. 53-54, with continuing reference to FIGS. 2 and 52, at step 1282A digital imagery of anatomy of a patient may be captured by imaging device(s) 16. The imaging device 16 may include any of the imaging devices disclosed herein. The data module 46 may be configured to receive image data associated with the patient. In implementations, one or more two-dimensional (e.g., X-ray) images 26 of the patient anatomy may be obtained by the imaging device 16. The data module 46 may be configured to receive image data including first and second two-dimensional images 26 of one or more bones of a patient. The two-dimensional images 26 may be substantially perpendicular or otherwise transverse to each other relative to an acquisition reference system of the imaging device 16.

In the implementation of FIGS. 53-54, the two-dimensional images 26 may include first and second images 26-A, 26-B associated with respective reference (e.g., image)

planes REFP-A, REFP-B. The image planes REFP-A, REFP-B may be substantially perpendicular to each other relative to the acquisition reference system of the imaging device(s) 16. One or more of the bones of the patient may be non-perpendicular to the image planes REFP-A, REFP-B and/or acquisition orientation of the imaging device 16.

At step 1282B, one or more profiles 1283 associated with the patient anatomy may be generated relative to the image plane(s) REFP-A, REFP-B. Each profile 1283 may be associated with a respective anatomical model 29 and/or one or more bone models 30 of the database 38. The spatial module 50 may be configured to establish one or more profiles 1283 associated with one or more bones of the anatomy.

In the implementation of FIG. 53, the spatial module 50 may be configured to determine a first (e.g., bone) profile 1283S-A associated with a first bone of the patient, such as a scapula. The spatial module 50 may be configured to determine a second (e.g., bone) profile 1283H-A associated with a second bone of the patient, such as a humerus. The spatial module 50 may be configured to establish a third (e.g., anatomical) profile 1283-A that may be associated with two or more bones of the anatomy. The anatomical profile 1283-A may include the bone profiles 1283S-A, 1283H-A. The bone profiles 1283S-A, 1283H-A and/or anatomical profile 1283-A may be associated with respective bone models 30 and/or an anatomical model 29. The spatial module 50 may be configured to establish the profiles 1283S-A, 1283H-A and 1283-A along the first image plane REFP-A associated with the first image 26-A.

In the implementation of FIG. 54, the spatial module 50 may be configured to determine a fourth (e.g., bone) profile 1283S-B associated with the first bone of the patient, such as the scapula. The spatial module 50 may be configured to determine a fifth (e.g., bone) profile 1283H-B associated with the second bone of the patient, such as the humerus. The spatial module 50 may be configured to establish a sixth (e.g., anatomical) profile 1283-B that may be associated with two or more bones of the anatomy. The anatomical profile 1283-B may include the bone profiles 1283S-B, 1283H-B. The bone profiles 1283S-B, 1283H-B and/or anatomical profile 1283-B may be associated with the respective bone models 30 and/or anatomical model 29. The spatial module 50 may be configured to establish the profiles 1283S-B, 1283H-B and 1283-B along the second image plane REFP-B associated with the second image 26-B. The bone profiles 1283S-A, 1283S-B may be associated with a common bone, such as the scapula, but may differ in geometry. The bone profiles 1283H-A, 1283H-B may be associated with a common bone, such as the humerus, but may differ in geometry. The anatomical profiles 1283-A, 1283-B may be associated with a common set of bones, such as the scapula and humerus, but may differ in geometry. The sets of bone profiles 1283S-A/1283S-B, 1283H-A/1283H-B and/or anatomical profiles 1283-A/1283-B may differ in geometry due to different acquisition positions of the imaging device(s) 16 relative to an acquisition reference system.

The planning environment 28 may be configured to select an anatomical model 29 from the database 38. The anatomical model 29 may be associated with one or more bones of the anatomy. In implementations, the planning environment 28 may be configured to select an anatomical model 29 associated with the bones encompassed in the images 26 of the patient.

At step 1282C, an acquisition orientation of the patient anatomy may be determined. Step 1282C may include selecting a (e.g., representative) anatomical model 1229 from a set of the anatomical models 29 in the database 38. The anatomical model 1229 may be associated with one or more bones of the anatomy, such as the scapula and humerus. In implementations, the anatomical model 1229 may include a first (e.g., scapula) bone model 1230S and a second (e.g., humerus) bone model 1230H. The representative anatomical model 1229 may be associated with another patient, such as a patient of a representative patient population.

The system 10 may be configured to select the representative anatomical model 1229 utilizing any of the techniques disclosed herein. In implementations, an anatomical (e.g., shoulder) SSM 75 may be established. The anatomical SSM 75 may be associated with a shoulder of the anatomy, including the scapula and humerus. The representative anatomical model 1229 may be associated with the anatomical SSM 75. Based on the shoulder SSM 75, the system 10 may be configured to predict or determine a shape, position and/or orientation of scapula and humerus.

The system 10 may be configured to determine an orientation of the first and second bones of the patient associated with the images 26-A, 26-B based on the representative anatomical model 1229. At step 1282C-2, one or more profile(s) 1283 of the patient anatomy may be compared to projection(s) of the representative anatomical model 1229 and associated bone models 1230S, 1230H onto the image plane(s) REFP-A, REFP-B. The spatial module 50 may be configured to establish one or more silhouettes 1285 associated with the anatomical model 1229 and/or bone models 1230H, 1230S.

Various techniques may be utilized to establish the silhouettes 1285. The spatial module 50 may be configured to project a first silhouette 1285-A of the representative anatomical model 1229 onto the first profile 1283-A of the patient anatomy along the first image plane REFP-A (FIG. 53). The spatial module 50 may be configured to project a second silhouette 1285-B of the representative anatomical model 1229 onto the second profile 1283-B of the patient anatomy along the second image plane REFP-B (FIG. 54). The spatial module 50 may be configured to set an acquisition orientation (e.g., camera angle or source) AO to establish the projection.

The comparison module 52 may be configured to compare the profiles 1283-A, 1283-B of the patient anatomy to the projection of the respective silhouettes 1285-A, 1285-B. The comparison module 52 may be configured to compare the profiles 1283-A, 1283-B of the patient anatomy to the projection of the respective silhouettes 1285-A, 1285-B.

The spatial module 50 may be configured to adjust the acquisition orientation AO to adjust (e.g., X, Y, Z) the projection of the silhouette 1285-A onto the first image plane REFP-A and/or the projection of the silhouette 1285-B onto the second image plane REFP-B. The comparison module 52 may be configured to determine a first fit between the first profile 1283-A and first silhouette 1285-A. The comparison module 52 may be configured to determine a second fit between the second profile 1283-A and second silhouette 1285-A. The comparison module 52 may be configured to determine an overall area deviation between the first fit and/or second fit. The spatial module 50 may be configured to adjust the acquisition orientation AO to minimize or otherwise reduce the overall area deviation below a predetermined threshold. The comparison module 52 may be configured to determine the minimum overall area deviation. The comparison module 52 may be configured to determine an acquisition orientation of the imaging device 16 based on the acquisition orientation AO associated with the minimum overall area deviation.

The spatial module 50 may be configured to determine a first acquisition orientation AO1 (FIG. 53) of the imaging device 16 associated with the first image 26-A based on comparing an overall fit between the first silhouette 1285-A and the first profile 1283-A. The spatial module 50 may be configured to determine the first acquisition orientation AO1 in response to iteratively adjusting a projection of the first silhouette 1283-A onto the first profile 1283-A along the first image plane REFP-A. The spatial module 50 may be configured to determine a second acquisition orientation AO2 (FIG. 54) of the imaging device 16 associated with the second image 26-B based on comparing an overall fit between the second silhouette 1285-B and the second profile 1283-B. The spatial module 50 may be configured to determine the second acquisition orientation AO2 in response to iteratively adjusting a projection of the second silhouette 1285-B onto the second profile 1283-B of the patient anatomy along the second image plane REFP-B. The system 10 may be configured to determine a shape, position and orientation of the bones of the anatomy associated with the images 26-A, 26-B based on the determined acquisition orientations AO1, AO2 and overall fit between the profiles 1283-A, 1283-B of the patient anatomy and the respective silhouettes 1285-A, 1285-B of the anatomical model 1229.

At step 1282D, a posture of the patient may be determined. The system 10 may be configured to determine one or more posture characteristics of the patient based on the determined acquisition orientation, including any of the posture characteristics disclosed herein. The system 10 may be configured to determine one or more of the posture characteristics based on the first acquisition orientation AO1 associated with the first image 26-A and/or the second acquisition orientation AO2 associated with the second image 26-B.

The system 10 may be configured to communicate one or more planning parameters to the surgeon or clinical user based on the determined posture characteristics. A surgical plan 36 may be established based on the determined posture. The system 10 may be configured to automatically generate a preoperative plan 36 based on the determined posture. The system 10 may be configured to establish a surgical plan 36 associated with the first bone and/or the second bone of the patient anatomy based on one or more of the determined posture characteristics. At step 1282E, an implant position may be determined based on the determined posture characteristic(s). The implant position may be associated with an implant model 32. The implant position may be determined utilizing any of the techniques disclosed herein. The system 10 may be configured to generate one or more indicators (e.g., suggestions) based on the detected posture, which may be communicated to the surgeon or clinical user. In implementations, the surgeon or clinical user may establish a preoperative surgical plan 36, which may include selection of various parameters including implant type, size, position and/or orientation based on the indicators. The surgeon may establish, modify, revise and/or approve the surgical plan 36, including selection of implant type, size, position and/or orientation, based on the determined posture characteristics.

At step 1282F, a range of motion may be determined based on the position and/or orientation of the implant model 32 associated with the implant position determined at step 1282E. The range of motion may be determined utilizing any of the techniques disclosed herein. The system 10 may be configured to compute or determine the shoulder range of motion for the preoperative plan based on parameters specified by the surgeon and/or system 10. The selected bone model 1230 may be associated with a respective AMC 80. The selected bone model 1230 and/or associated AMC 80 may be utilized to determine range of motion.

One or more bones of the patient anatomy may be fractured due to trauma. The fracture may generate one or more bone fragments. In scenarios, some fragments may be relatively small and may not utilized for reconstruction of the bone. Utilizing the techniques disclosed herein, a pre-fracture state of the bone may be determined for reducing or otherwise arranging the bone fragments and reconstructing the bone in a bone fracture repair technique. The bone fragments may be arranged relative to a volume of a three-dimensional model of the bone, which may serve as a template. The disclosed techniques may be utilized to assist in predicting a type of fracture and selection of a treatment option. The disclosed techniques may be utilized to treat various bones and joints of the anatomy, including any of the bones and joints disclosed herein, including long bones such as a humerus, tibia, femur, etc.

Figure 55:
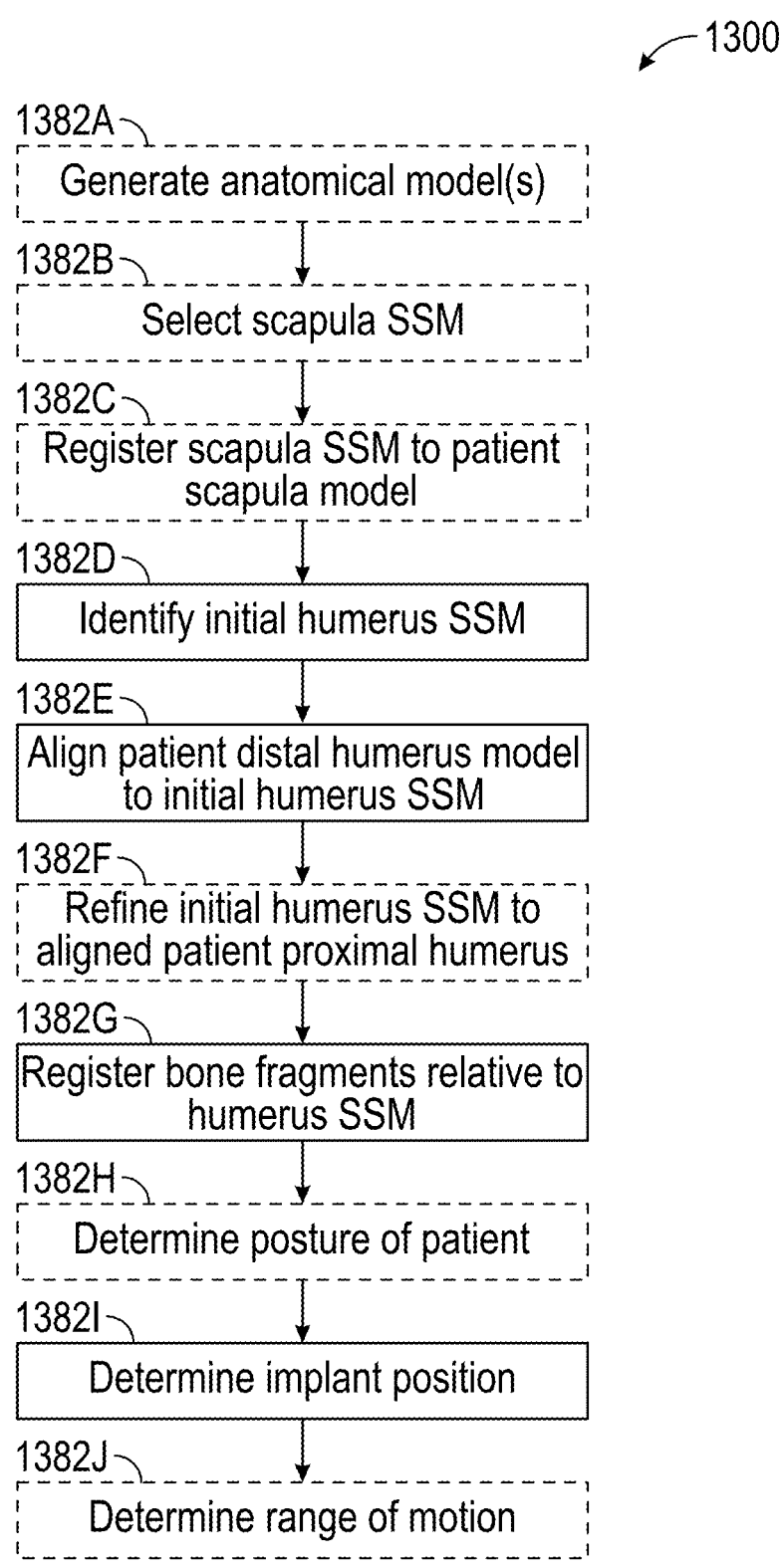
FIG. 55 discloses a method for planning a surgical procedure on a respective patient using a surgical planning system, including arranging bone fragments.

FIG. 55 discloses a method in a flowchart 1382 for a surgical procedure. The method 1382 may be utilized to pre-operatively plan, implement, evaluate and/or validate aspects of various surgical procedures, such as an arthroplasty for restoring functionality to shoulders, ankles, knees, hips and other joints. The method 1382 may be utilized with any of the planning systems and methods, virtual anatomical models and/or bone models disclosed herein, such as the planning system 10. The method 1382 may be utilized to register one or more bone fragments of a bone for reconstructing the bone in a bone fracture repair technique. The method 1382 may be utilized to determine a position and/or orientation of one or more implants to secure the bone fragments. Fewer or additional steps than are recited below could be performed within the scope of this disclosure, and the recited order of steps is not intended to limit this disclosure. The method 1382 may incorporate any of the steps of method 382, 482, 582 and/or 1282 disclosed herein, and vice versa. Reference is made to the system 10.

Referring to FIG. 2, with continuing reference to FIG. 55, at step 1382A one or more anatomical models 29 and/or bone models 30 may be generated. The system 10 may be configured to generate the anatomical models 29 and/or bone models 30 utilizing any of the techniques disclosed herein.

Figures 56A, 56B, 56C:
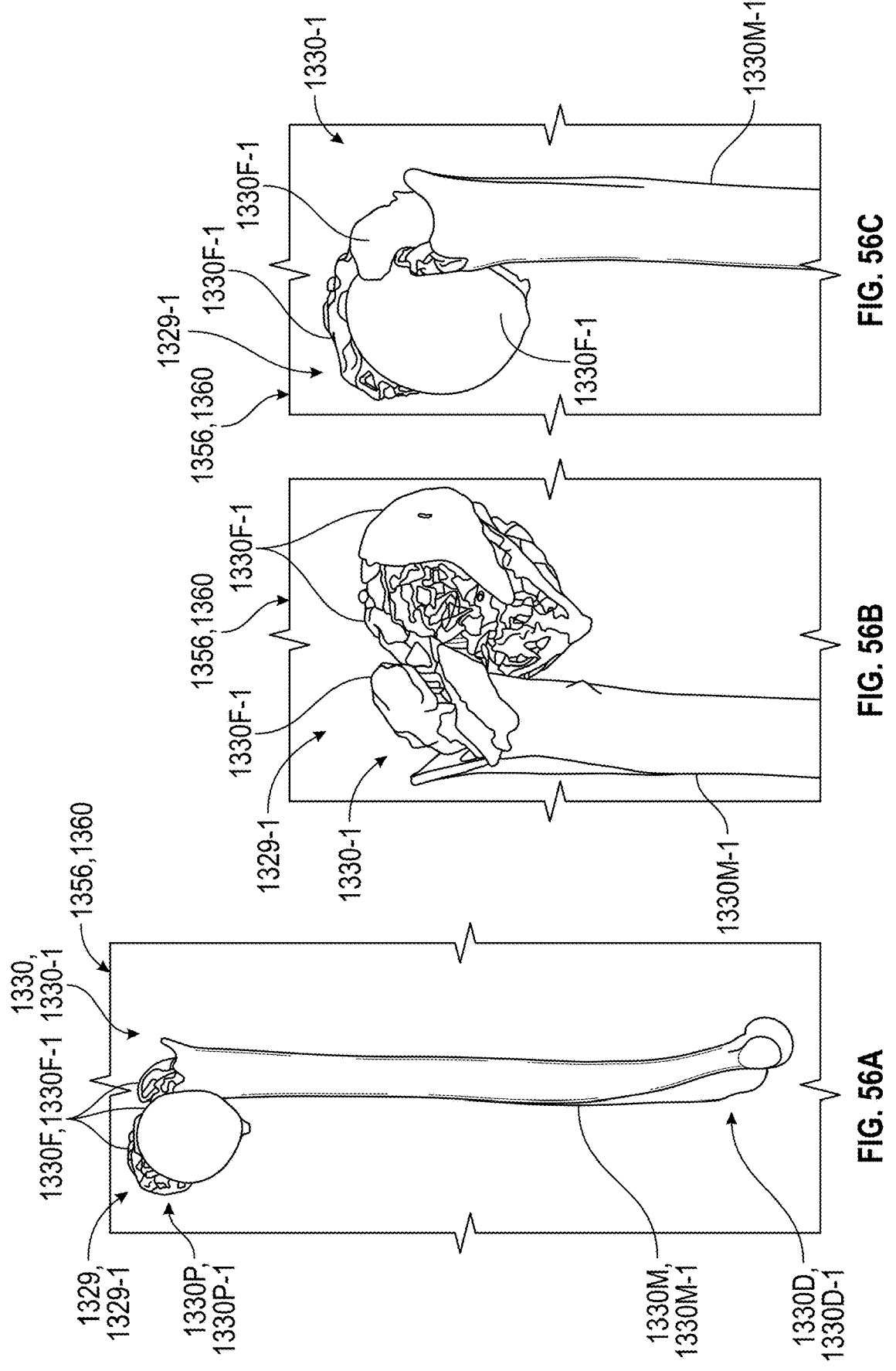
FIGS. 56A-56C, 57A-57B, 58A-58C, 59A-59C and 60 disclose various arrangements of bone fragments.

Referring to FIGS. 56A-56C, with continuing reference to FIGS. 2 and 55, in implementations the anatomical models 29 may include a three-dimensional anatomical model 1329 associated with a patient (indicated at 1329-1). The anatomical model 1329-1 may include at least one (e.g., fragmentary) three-dimensional bone model 1330-1 associated with a bone of the patient. The fragmentary bone model 1330-1 may be associated with any of the bones and joints disclosed herein, including a long bone such as a humerus. The data module 46 may be configured to access the fragmentary bone model 1330-1. The anatomical model 1329-1 may include other bone models, such as the scapula bone model 530S-1 (see, e.g., FIGS. 41-43). Each bone model 1330 may include a main body (e.g., diaphysis) portion 1330M that may extend between a proximal portion 1330P and a distal portion 1330D. The main body portion 1330M may be associated with a diaphysis of a long bone such as the humerus.

The patient bone model 1330-1 may include one or more three-dimensional bone fragment portions 1330F-1. The fragment portions 1330F-1 may be associated with one or more respective fragments of the bone. The main body portion 1330M-1 of the patient may be associated with a non-fragmentary portion (e.g., remainder) of the bone. The fragment portions 1330F-1 may be associated with a proximal portion 1330P-1 of the humerus, including portions of a humeral head. The main body portion 1330M-1 may be associated with a distal portion of the humerus, including a diaphysis of the humerus. The system 10 may be configured to receive image data associated with the patient. The system 10 may be configured to generate the fragmentary bone model 1330-1 based on the image data.

Various techniques may be utilized to re-position the fragment portions 1330F-1 relative to the main body portion 1330M-1 of the fragmentary bone model 1330-1 of the patient. At step 1382B, a second bone model 30 (FIG. 2) associated with another bone of the anatomy may be selected. The second bone model 30 may be associated with an non-adjoining or adjoining bone of the anatomy, such as a scapula. The bone model 30 may be associated with another patient, such as a patient of a representative patient population. The bone model 30 may be selected utilizing any of the techniques disclosed herein, including step 582B of the method 582 (FIG. 39). In implementations, the selected bone model 30 may be the scapula bone model 530S-2 (see, e.g., FIGS. 42-43). The scapula bone model 530S-2 may be associated with a SSM 75. The statistical shape modeler 72 may be configured analyze the representative patient population within the SSM 75, which may be associated with one or more bones of the anatomical model 1329-1 of the patient such as the scapula and/or humerus.

At step 1382C, the representative scapula bone model 530S-2 may be registered relative to the scapula bone model 530S-1 associated with the patient to establish a registered state of the scapula bone model 530S-2 (see, e.g., FIGS. 42-43). The scapula bone model 530S-2 may be registered utilizing any of the techniques disclosed herein, such as step 582C and/or 582D of method 582 (FIG. 39). Step 1392C may include at least partially registering the representative scapula bone model 530S-2 to the scapula bone model 530S-1 of the patient to establish a registered state (e.g., position) of the scapula bone model 530S-2.

Figures 57A, 57B:
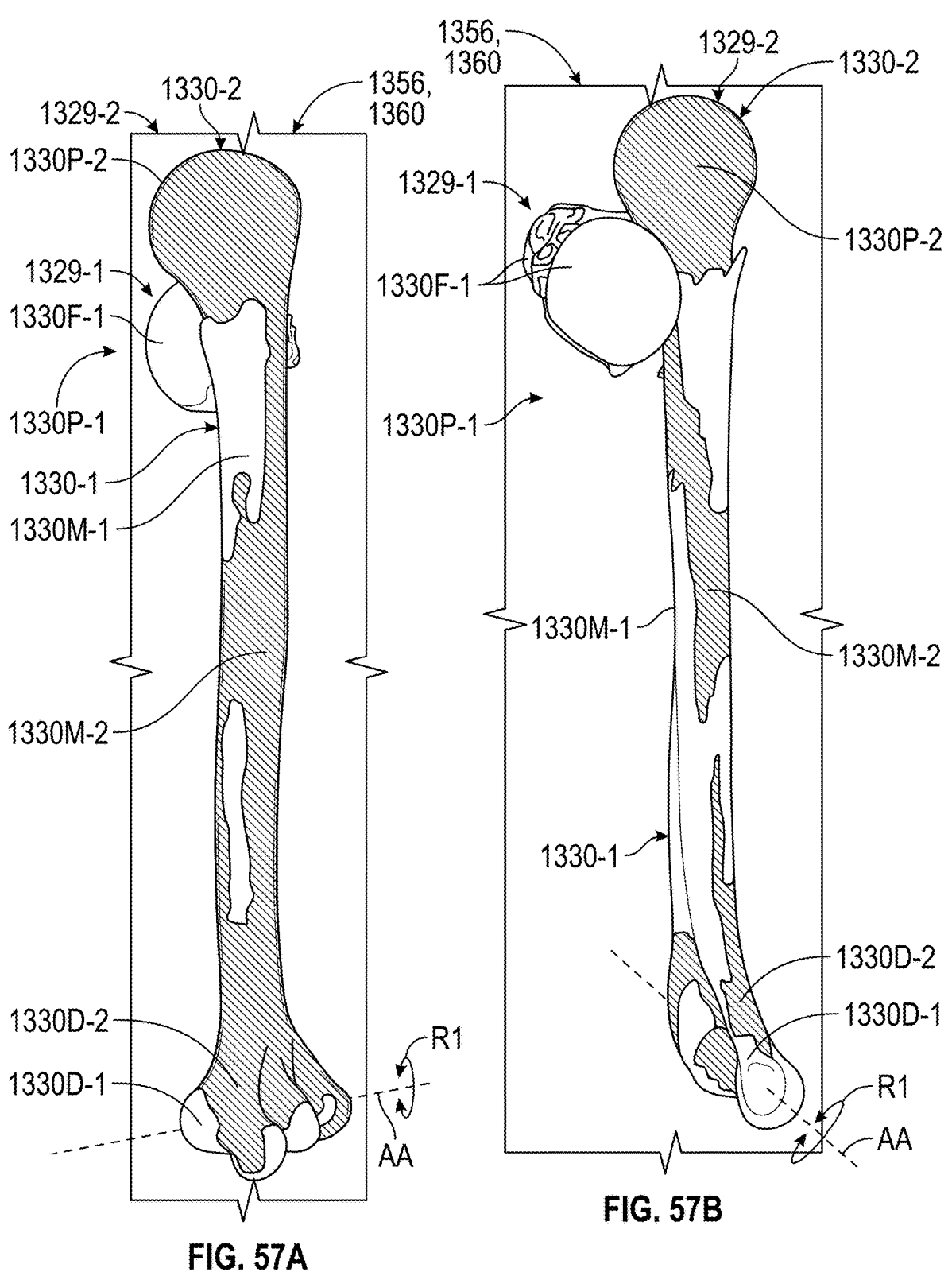

Referring to FIGS. 57A-57B, with continuing reference to FIGS. 2 and 55, at step 1382D a representative (e.g., initial or humerus) three-dimensional bone model 1330-2 associated with another bone of the anatomy may be selected or otherwise identified. The data module 46 may be configured to access the representative bone model 1330-2 from memory. The bone associated with the representative bone model 1330-2 may be the same bone as the fragmented bone of the patient. The representative bone model 1330-2 may be associated with the humerus. The data module 46 may be configured to access the representative bone model 1330-2 from memory. The system 10 may select or otherwise identify the representative bone model 1330-2 utilizing any of the techniques disclosed herein, including any of the techniques associated with step 582E of method 582 (FIG. 39). The system 10 may be configured to select the representative bone mode 1330-2 from a set of three-dimensional bone models 30 associated with the bone of the patient and a representative patient population, such as the humerus.

Step 1382D may include selecting the representative bone model 1330-2 from the set of the bone models 30 associated with the same bone as the fragmentary bone of the patient in response to establishing the registered state of the representative bone model 530S-2 (see, e.g., FIG. 44). The selected representative bone model 1330-2 may be associated with the same anatomical model 1329-2 as the representative bone model 530S-2, which may be associated with another patient of the representative patient population.

At step 1382E the main body portion 1330M-1 and/or distal portion 1330D-1 of the fragmentary bone model 1330-1 may be at least partially registered or otherwise substantially aligned with the representative bone model 1330-2 to establish a registered state (e.g., position) of the fragmentary bone model 1330-1. The spatial module 50 may be configured to register or otherwise substantially align the fragmentary bone model 1330-1 to the representative bone model 1330-2 utilizing any of the techniques disclosed herein, including any of the techniques associated with step 582F of method 582 (FIG. 39). Step 1382E may include at least partially registering the main body portion 1330M-1 of the fragmentary bone model 1330-1 to the main body portion 1330M-2 of the representative bone model 1330-2 to establish the registered state of the fragmentary bone model 1330-1. The spatial module 50 may be configured to at least partially register the main body portion 1330M-1 of the fragmentary model 1330-1 to the main body portion 1330M-2 of the representative bone model 1330M-2 to establish the registered state of the fragmentary bone model 1330-1. In implementations, the spatial module 50 may be configured to substantially align a first (e.g., epicondylar) axes AA of the distal portions 1330D-1, 1330D-2 of the bone models 1330-1, 1330-2. The spatial module 50 may be configured to rotate the main body portion 1330M-1 of the fragmentary bone model 1330-1 in a rotational direction R1 about the respective axis AA to substantially align the main body portion 1330M-1 with the main body portion 1330M-2 of the representative bone model 1330-2.

At step 1382F, registration of the initially selected representative bone model 1330-2 to the registered position of the fragmentary bone model 1330-1 of the patient may be refined. The system 10 may be configured to refine registration of the representative bone model 1330-2 to the registered position of the fragmentary bone model 1330-1 utilizing any of the techniques disclose herein. In implementations, the representative bone model 1330-2 may be positionally adjusted and/or another representative bone model 1330-2 may be selected from a set of representative bone models 30 utilizing any of the techniques disclosed herein. The set of representative bone models 30 may be associated with the SSM 75. In implementations, a representative anatomical model 1329-2 associated with the bones of the anatomy (e.g., scapula and humerus) may be positionally adjusted and/or selected utilizing any of the techniques disclosed herein. The representative anatomical model 29 may be the same or may differ from the previously selected anatomical bone model 1329-2. The system 10 may be configured to refine a selection of the representative bone model 1330-2 based on a fit between the patient anatomical model 1329-1 and another anatomical model 1329-2 selected from a set of anatomical models 29, which may be associated with an anatomical SSM 75. In implementations, one more steps of the method 1382 may include analyzing the representative patient population within the SSM 75, including step 1382C and/or step 1382F. The representative patient population may be analyzed within the SSM 75 utilizing any of the techniques disclosed herein.

In implementations, one or more modes of variation 76 of the SSM 75 may be varied to minimize or otherwise reduce a volume deviation between the selected representative anatomical model 1329-2 from a set of the anatomical models 29 and the registered (e.g., aligned) position of the patient anatomical model 1329-1 including the scapula bone model 530S-1 (FIG. 44) and the registered (e.g., aligned)

position of the fragmentary bone model 1330-1. The system 10 may be configured to vary the modes of variation 76 to refine or otherwise positionally adjust and/or select the anatomical model 1329-2 and associated humerus bone model 1330-2 utilizing any of the techniques disclosed herein, such as step 482G of method 482 (FIG. 33). Step 1382B, 1382C, 1382D and/or 1382F may include positionally adjusting and/or selecting the representative bone model 530S-2 (e.g., FIG. 42) and/or the representative bone model 1330-2 in response to varying one or more of the predefined modes of variation 76 within the associated SSM 75.

Figures 58A, 58B, 58C:
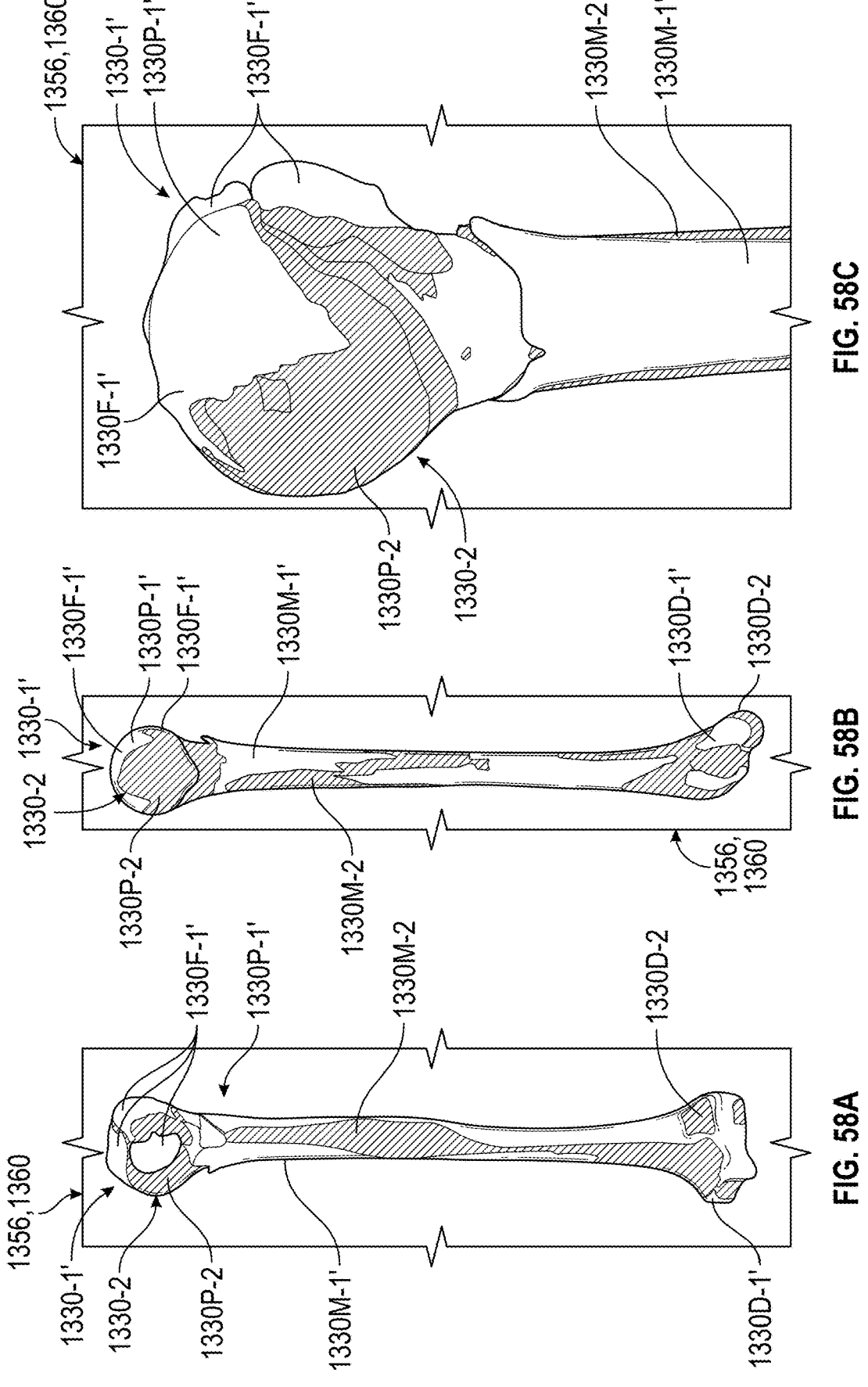
Figures 59A, 59B, 59C:
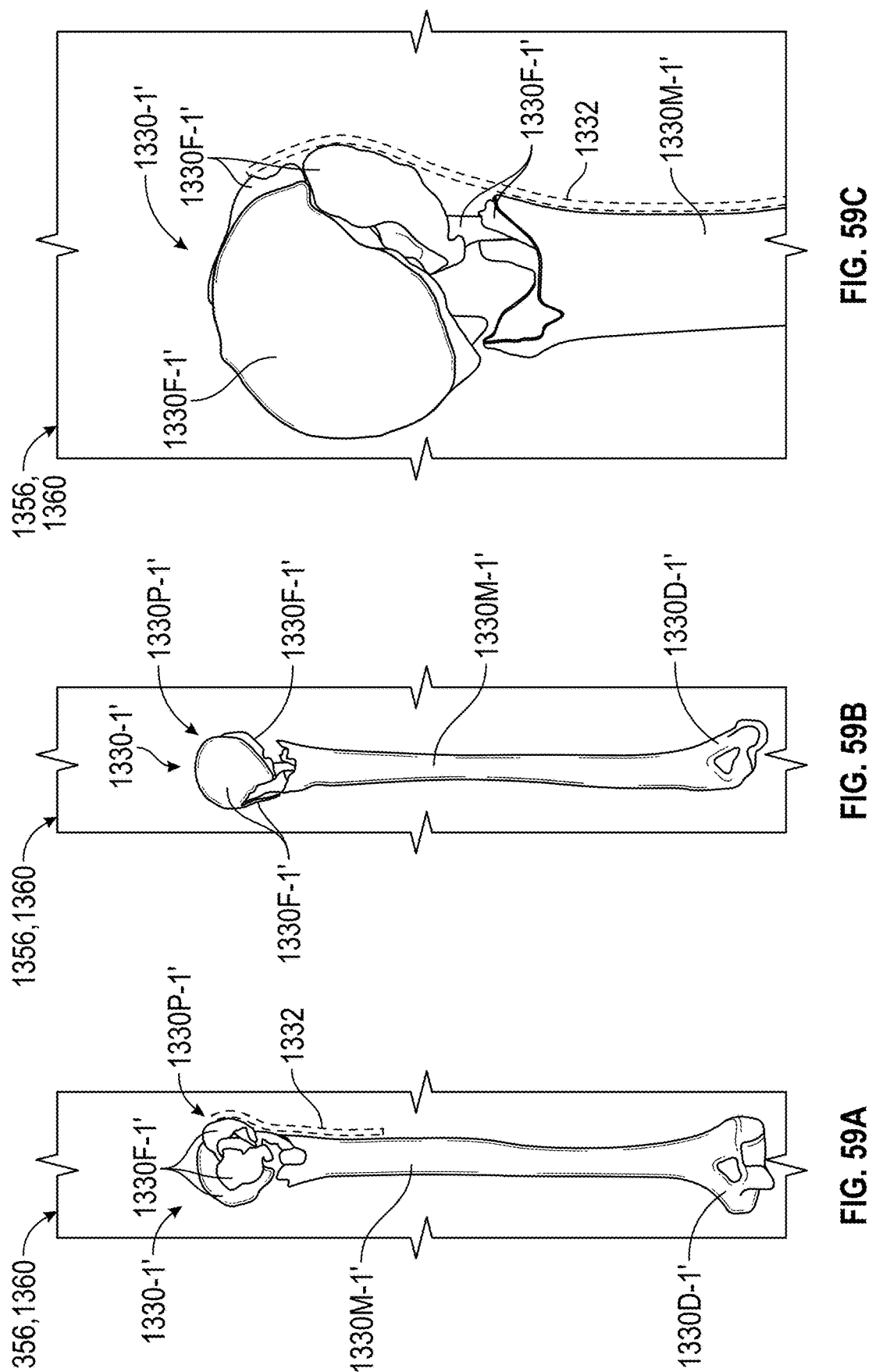

Referring to FIGS. 58A-58C, with continuing reference to FIGS. 2, 4 and 55, various techniques may be utilized to position the bone fragments. At step 1382G, one or more of the fragment portions 1330F-1 of the fragmentary bone model 1330-1 may be at least partially registered or otherwise substantially aligned to a volume of the representative bone model 1330-2 to establish a registered state (e.g., position) of the fragmentary bone model 1330-1'. FIGS. 58A-58C disclose a registered state of the fragmentary bone model 1330-1' of the patient positioned relative to the representative bone model 1330-2. FIGS. 59A-59C disclose the registered state of the fragmentary bone model 1330-1' of the patient with the representative bone model 1330-2 omitted.

Various techniques may be utilized to fit or otherwise position the fragment portions 1330F-1 of the patient bone model 1330-1 relative to a volume of the representative bone model 1330-2. The fragment portions 1330F-1 may be fit automatically by the system 10 and/or manually in response to user interaction with the user interface 56. The spatial module 50 may be configured to at least partially register a volume of one or more of the fragment portions 1330F-1 of the fragmentary bone model 1330-1 to the volume of the representative bone model 1330-2 to establish the registered state of the fragmentary bone model 1330-1'.

The spatial module 50 may be configured to determine an overall volume of the fragment portions 1330F-1 of the fragmentary bone model 1330-1' that may be outside of the volume of the representative bone model 1330-2. The comparison module 52 may be configured to select an arrangement of the fragment portions 1330F-1 that may minimize or otherwise reduce the overall volume of the fragment portions 1330F-1 of the fragmentary bone model 1330-1' that may be outside of the volume of the representative bone model 1330-2.

Figure 60:
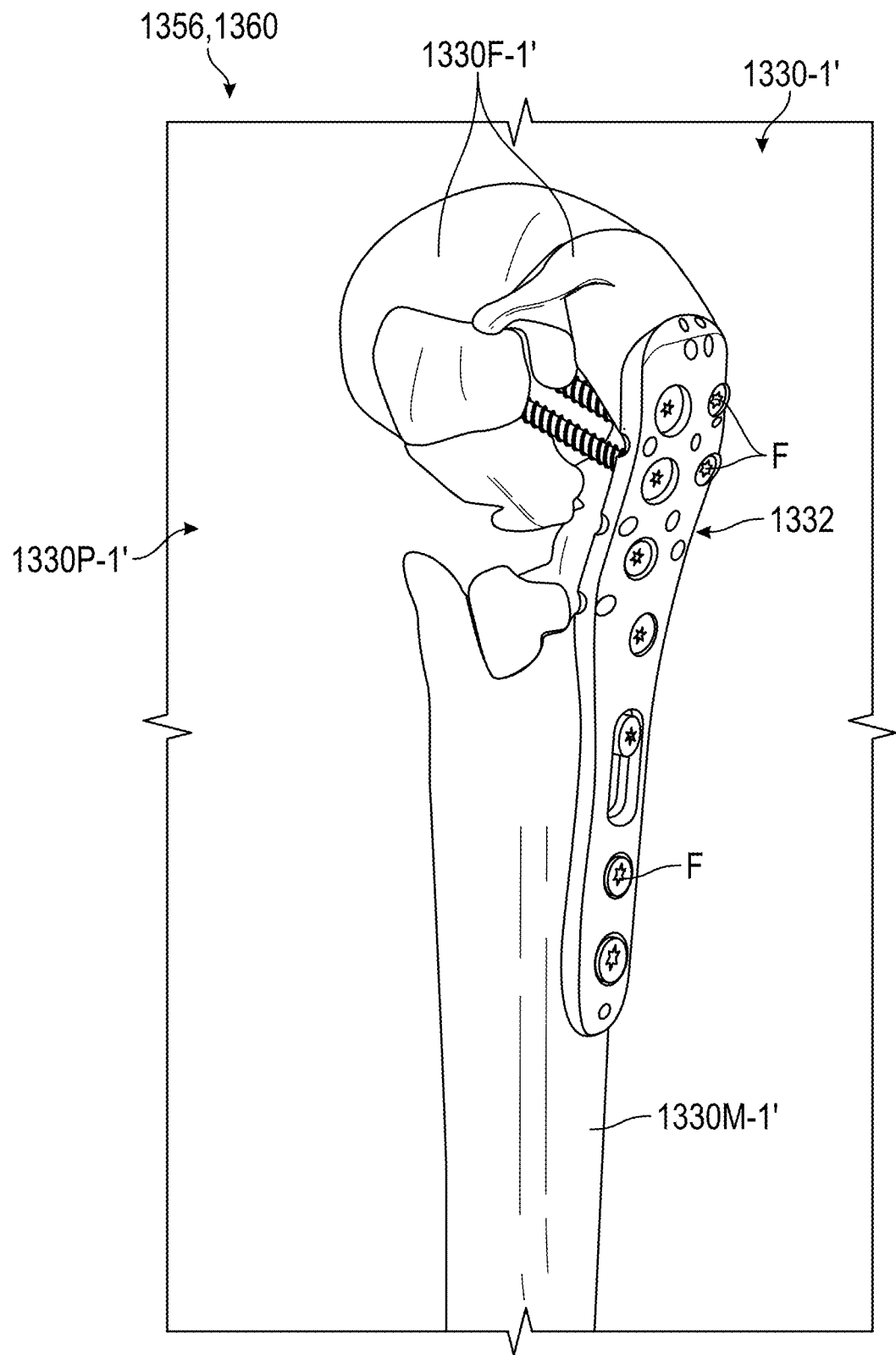

Method 1382 may include analyzing the fragmented bone of the patient based on the registered state of the fragmentary bone model 1330-1'. At step 1382H, a posture of the patient may be determined utilizing any of the techniques disclosed herein. At step 1382I, a position and/or orientation of one or more implant models 1332 may be determined utilizing any of the techniques disclosed herein (model 1332 shown in dashed lines in FIGS. 59A and 59C). Step 1382I may incorporate any of the techniques associated with step 482G (FIG. 33). The system 10 may be configured to establish an implant plan associated with the implant model(s) 1332 based on the registered state of the fragmentary bone model 1330-1'. The implant plan may be associated with at least one implant configured to secure one or more bone fragments. Step 1382I may include establishing the implant plan based on the registered state of the fragmentary bone model 1330-1'. Step 1382I may include positioning at least one implant model 1332 adjacent to one or more of the fragment portions 1330F-1 of the fragmentary bone model 1330-1' in the registered state. FIG. 60 discloses the implant model 1332 secured to the fragmentary bone model 1330-1' utilizing one or more fastener models F associated with respective fasteners, such as compression screws.

At step 1382J, a range of motion may be determined utilizing any of the techniques disclosed herein. The range of motion may be associated with the registered state of the fragmentary bone model 1330-1'. Step 1382J may incorporate any of the techniques associated with step 482H (FIG. 33).

Although the techniques disclosed herein relating to posture refer to a scapula of a patient, it should be understood that the teachings herein may be utilized to determine range of motion and/or establish or adjust a preoperative plan for other bones and joints.

The proposed surgical planning systems and methods of this disclosure may be utilized to create and implement surgical plans that are tailored to the individual patient, which may improve healing. The disclosed systems and methods may reduce complexity in implementing the surgical plans, including reduced packaging and instrumentation. In certain implementations, the system and methods may utilize feedback loops for continuously improving the recommendations provided when developing surgical plans. The proposed systems and methods therefore provide improved functionality compared to prior planning systems.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical planning system, comprising:

one or more processors operably connected to memory and configured to execute a planning environment; and wherein the planning environment is configured to:

access a first three-dimensional bone model from the memory, the first bone model associated with a first bone;

access a fragmentary three-dimensional bone model of the first bone of a patient, the fragmentary bone model including a first portion and including one or more fragment portions associated with one or more respective fragments of a fracture of the first bone;

at least partially register the first portion and the one or more fragment portions of the fragmentary bone model to a volume of the first bone model to establish a registered state of the fragmentary bone model; and re-position the one or more fragment portions relative to the first portion to establish the registered state of the fragmentary bone model.

2. The surgical planning system as recited in claim 1, wherein the planning environment is configured to:

establish an implant plan based on the registered state of the fragmentary bone model, the implant plan associated with at least one implant configured to secure one or more bone fragments.

3. The surgical planning system as recited in claim 1, wherein the planning environment is configured to:

receive image data associated with the patient; and generate the fragmentary bone model based on the image data.

4. The surgical planning system as recited in claim 1, wherein the first bone is a long bone, the first portion of the fragmentary bone model includes a diaphysis portion associated with a diaphysis of the long bone, and the planning environment is configured to:

at least partially register the diaphysis portion of the fragmentary bone model to a diaphysis portion of the first bone model to establish the registered state of the fragmentary bone model.

5. A surgical planning system, comprising:

one or more processors operably connected to a storage system and configured to execute a planning environment;

wherein the storage system is configured to store a plurality of three-dimensional bone models associated with one or more bones and/or one or more joints of a representative patient population; and wherein the planning environment is configured to:

select a first three-dimensional bone model from a first set of the bone models associated with a first bone of the representative patient population;

at least partially register a non-fragmentary portion and one or more fragment portions of a fragmentary three-dimensional bone model of the first bone of a patient to the first bone model to establish a registered state of the fragmentary bone model, wherein the one or more fragment portions are associated with one or more respective fragments of a fracture of the first bone, and the non-fragmentary portion is associated with a remainder of the first bone of the patient; and re-position the one or more fragment portions relative to the non-fragmentary portion to establish the registered state of the fragmentary bone model.

6. The surgical planning system as recited in claim 5, wherein the planning environment is configured to:

establish an implant plan based on the registered state of the fragmentary bone model.

7. The surgical planning system as recited in claim 5, wherein the planning environment is configured to:

select a second three-dimensional bone model from a second set of the bone models associated with a second bone of the representative patient population;

at least partially register the second bone model to a three-dimensional bone model of the second bone of the patient to establish a registered position of the second bone model; and select the first bone model from the first set of the bone models in response to establishing the registered position of the second bone model.

8. The surgical planning system as recited in claim 7, wherein:

the second bone cooperates with the first bone to establish a joint;

a volume of the fragmentary bone model in the registered state excludes an omitted portion of the first bone, but a volume of the first bone model includes the omitted portion of the first bone; and the planning environment is configured to:

select the second bone model from the second set of the bone models by analyzing the representative patient population within a statistical shape model, wherein the statistical shape model includes a plurality of predefined modes that characterize anatomical differences within the representative patient population and a plurality of standard deviations of anatomical variances contained within each of the plurality of predefined modes; and establish an implant plan based on the registered state of the fragmentary bone model, the implant plan associated with at least one implant configured to secure one or more bone fragments.

9. The surgical planning system as recited in claim 5, wherein the planning environment is configured to:

analyze the representative patient population within a statistical shape model.

10. The surgical planning system as recited in claim 9, wherein:

the planning environment is configured to:

create a plurality of anatomical makeup classifications based on a plurality of predefined modes within the statistical shape model that characterize anatomical differences within the representative patient population and a plurality of standard deviations of anatomical variances contained within each of the plurality of predefined modes; and assign the anatomical makeup classifications to the bone models; and the storage system is configured to store the anatomical makeup classifications.

11. The surgical planning system as recited in claim 10, wherein the planning environment is configured to:

establish an implant plan based on the registered state of the fragmentary bone model, the implant plan associated with at least one implant configured to secure one or more bone fragments.

12. The surgical planning system as recited in claim 10, wherein the planning environment is configured to:

select a second three-dimensional bone model from a second set of the bone models associated with a second bone of the representative patient population;

at least partially register the second bone model to a three-dimensional bone model of the second bone of the patient to establish a registered position of the second bone model; and select the first bone model from the first set of the bone models based on the registered position of the second bone model.

13. The surgical planning system as recited in claim 5, wherein the first bone is a humerus.

14. The surgical planning system as recited in claim 13, wherein the one or more fragments are associated with a proximal portion of the humerus.

15. A computer implemented surgical planning method comprising the steps of:

selecting a first three-dimensional bone model associated with a first bone;

selecting a fragmentary three-dimensional bone model of the first bone of a patient, the fragmentary bone model including a first portion and including one or more fragment portions associated with one or more respective fragments of a fracture of the first bone;

at least partially registering the first portion and the one or more fragment portions of the fragmentary bone model to a volume of the first bone model to establish a registered state of the fragmentary bone model;

re-positioning, using one or more processors, the one or more fragment portions relative to the first portion to establish the registered state of the fragmentary bone model; and analyzing the first bone based on the registered state of the fragmentary bone model.

16. The method as recited in claim 15, further comprising:

establishing an implant plan based on the registered state of the fragmentary bone model, including positioning at least one implant model adjacent to the one or more fragment portions of the fragmentary bone model in the registered state.

17. The method as recited in claim 16, wherein the first bone is a long bone, the first portion of the fragmentary bone model includes a diaphysis portion associated with a diaphysis of the long bone, and further comprising:

at least partially registering the diaphysis portion of the fragmentary bone model to a diaphysis portion of the first bone model to establish the registered state of the fragmentary bone model.

18. The method as recited in claim 16, further comprising:

accessing a plurality of three-dimensional bone models associated with one or more bones and/or one or more joints of a representative patient population; and selecting the first bone model from a first set of the bone models associated with the first bone of the representative patient population.

19. The method as recited in claim 18, further comprising:

selecting a second three-dimensional bone model from a second set of the bone models associated with a second bone of the representative patient population;

at least partially registering the second bone model to a bone model of the second bone of the patient to establish a registered position of the second bone model; and selecting the first bone model from the first set of the bone models in response to establishing the registered position of the second bone model.

20. The method as recited in claim 18, further comprising:

analyzing the representative patient population within a statistical shape model.

21. The method as recited in claim 20, further comprising:

identifying a plurality of predefined modes within the statistical shape model of the representative patient population;

establishing a plurality of standard deviations of anatomical variances contained within each of the plurality of predefined modes; and wherein the step of selecting the first bone model occurs in response to varying one or more of the predefined modes within the statistical shape model.

22. The surgical planning system as recited in claim 1, wherein the one or more fragment portions include a plurality of fragment portions.

23. The surgical planning system as recited in claim 5, wherein the one or more fragment portions include a plurality of fragment portions.

* * * * *